(12) United States Patent
Xie et al.

(10) Patent No.: US 10,066,204 B2
(45) Date of Patent: Sep. 4, 2018

(54) CHEMICALLY LABILE PEPTIDE-PRESENTING SURFACES FOR CELLULAR SELF-ASSEMBLY

(71) Applicant: Wisconsin Alumni Research Foundation, Madison, WI (US)

(72) Inventors: Angela W. Xie, Middleton, WI (US); William L. Murphy, Waunakee, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 84 days.

(21) Appl. No.: 14/486,600

(22) Filed: Sep. 15, 2014

(65) Prior Publication Data

US 2015/0024490 A1   Jan. 22, 2015

Related U.S. Application Data

(63) Continuation-in-part of application No. 13/835,102, filed on Mar. 15, 2013.

(51) Int. Cl.
| | | |
|---|---|---|
| *C12N 5/0735* | (2010.01) | |
| *C12N 5/07* | (2010.01) | |
| *C12N 5/00* | (2006.01) | |
| *C07K 7/00* | (2006.01) | |
| *C07K 5/12* | (2006.01) | |

(52) U.S. Cl.
CPC .............. *C12N 5/0606* (2013.01); *C07K 5/12* (2013.01); *C07K 7/00* (2013.01); *C12N 5/0068* (2013.01); *C12N 5/06* (2013.01); *C12N 2531/00* (2013.01); *C12N 2533/50* (2013.01); *C12N 2539/10* (2013.01)

(58) Field of Classification Search
None
See application file for complete search history.

(56) References Cited

U.S. PATENT DOCUMENTS

| | | |
|---|---|---|
| 6,767,928 B1 | 7/2004 | Murphy et al. |
| 7,132,506 B2 | 11/2006 | Nishimura et al. |
| 8,420,774 B2 | 4/2013 | Murphy et al. |
| 2002/0151617 A1 | 10/2002 | Mao et al. |
| 2004/0162580 A1 | 8/2004 | Hain |
| 2005/0063941 A1 | 3/2005 | Bezemer et al. |
| 2008/0095817 A1 | 4/2008 | Murphy |
| 2010/0197013 A1 | 8/2010 | Kamp et al. |

FOREIGN PATENT DOCUMENTS

WO     WO-2011145077 A2 *  11/2011  ............. A61K 47/42

OTHER PUBLICATIONS

Inaba et al. Electrochemical desorption of self-assembled monolayers for engineering cellular tissues. Biomaterials, v30 (2009), p. 3573-3579.*

(Continued)

*Primary Examiner* — Sean C. Barron
(74) *Attorney, Agent, or Firm* — Stinson Leonard Street LLP

(57) ABSTRACT

Methods of cell culture using patterned SAM arrays are disclosed. Advantageously, the disclosed methods use SAM arrays presenting adhesion peptides to grow confluent monolayers that can invaginate to form an embryoid body.

8 Claims, 47 Drawing Sheets
(28 of 47 Drawing Sheet(s) Filed in Color)
Specification includes a Sequence Listing.

(56) References Cited

OTHER PUBLICATIONS

Sandstrom et al. Nonspecific and Thiol-Specific Binding of DNA to Gold Nanoparticles. Langmuir, v19 (2003), p. 7537-7543.*
Shabbir et al. An Inhibitor of a Cell Adhesion Receptor Stimulates Cell Migration. Angew. Chem. Int. Ed. 2010, 49, 7706-7709. (Year: 2010).*
Huth et al. Neural Stem Cell Spreading on Lipid Based Artificial Cell Surfaces, Characterized by Combined X-ray and Neutron Reflectometry. Materials 2010, 3, 4994-5006. (Year: 2010).*
Kilian et al. Directing Stem Cell Fate by Controlling the Affinity and Density of Ligand—Receptor Interactions at the Biomaterials Interface. Angew. Chem. Int. Ed. 2012, 51, 4891-4895. (Year: 2012).*
Marko et al. A Novel Synthetic Peptide Polymer with Cyclic RGD Motifs Supports Serum-Free Attachment of Anchorage-Dependent Cells. Bioconjugate Chem. (2008), 19:1757-1766. (Year: 2008).*
Bracher et al. The Relative Rates of Thiol-Thioester Exchange and Hydrolysis for Alkyl and Aryl Thioalkanoates in Water. Orig Life Evol Biosph (2011), 41:399-412. (Year: 2011).*
Prime and Whitesides, J. Am. Chem. Soc. 115(23):10714-10721 (1993).
Gill and von Hippel, Analytical Biochemistry 182(2):319-326 (1989).
Koepsel and Murphy, Langmuir 25(21):12825-34 (2009).
Aro, H. T.; Markel, M. D.; Chao, E. Y., Cortical bone reactions at the interface of external fixation half-pins under different loading conditions. J Trauma 1993, 35, (5), 776-85.
Lee et al., "Modular Peptide Growth Factors for Substrate-Mediated Stem Cell Differentiation," Angew. Chem. Int. Ed., 48(34): 6266-6269 (2009).
Lee et al., "Modular Peptides Promote Human Mesenchymal Stem Cell Differentiation on Biomaterial Surfaces," Acta Biomaterialia, 2009, doi: 10.1016/j.act.bio.2009.08.003.
Blom, E.J., et al., "Transforming growth factor-β1 incorporation in a calcium phosphate bone cement: Material properties and release characteristics," J Biomed Mater Res 59: 265-272, 2002.
Murphy, W. L.; Hsiong, S.; Richardson, T. P.; Simmons, C. A.; Mooney, D. J., Effects of a bone-like mineral film on phenotype of adult human mesenchymal stem cells in vitro. Biomaterials 2005, 26, (3), 303-10.
Murphy, W. L.; Kohn, D. H.; Mooney, D. J., Growth of continuous bonelike mineral within porous poly(lactide-co-glycolide) scaffolds in vitro. J Biomed Mater Res 2000, 50, (1), 50-8.
Murphy, W. L.; Mercurius, K. O.; Koide, S.; Mrksich, M., Substrates for cell adhesion prepared via active site-directed immobilization of a protein domain. Langmuir 2004, 20, (4), 1026-1030.
Murphy, W. L.; Mooney, D. J., Molecular-scale biomimicry. Nat Biotechnol 2002, 20, (1), 30-1.
Lu, Y.; Markel, M. D.; Nemke, B.; Lee, J. S.; Graf, B. K.; Murphy, W. L., Influence of hydroxyapatite-coated growth factor-releasing interference screws on tendon-bone healing in an ovine model. Arthroscopy 2009, 25, (12), 1427-1435.
Murphy, W. L.; Dillmore, W. S.; Modica, J.; Mrksich, M., Dynamic hydrogels: translating a protein conformational change into macroscopic motion. Angew Chem Int Ed Engl 2007, 46, (17), 3066-9.
Murphy, W. L.; Mooney, D. J., Controlled delivery of inductive proteins, plasmid DNA and cells from tissue engineering matrices. J Periodontal Res 1999, 34, (7), 413-419.
Richardson, T. P.; Murphy, W. L.; Mooney, D. J., Polymeric delivery of proteins and plasmid DNA for tissue engineering and gene therapy. Crit Rev Eukaryot Gene Expr 2001, 11, (1-3), 47-58.
Richardson, T. P.; Murphy, W. L.; Mooney, D. J., Selective adipose tissue ablation by localized, sustained drug delivery. Plast Reconstr Surg 2003, 112, (1), 162-70.
Fazan, F.; Marquis, P., Dissolution behavior of plasma-sprayed hydroxyapatite coatings. Journal of Materials Science-Materials in Medicine 2000, 11, (12), 787-792.
Lin, J.; Kuo, K.; Ding, S.; Ju, C., Surface reaction of stoichiometric and calcium-deficient hydroxyapatite in simulated body fluid. Journal of Materials Science-Materials in Medicine 2001, 12, (8), 731-741.
Driessens, F. C.; van Dijk, J. W.; Borggreven, J. M., Biological calcium phosphates and their role in the physiology of bone and dental tissues I. Composition and solubility of calcium phosphates. Calcif Tissue Res 1978, 26, (2), 127-37.
Bunker, B. C., Rieke, P.C., Tarasevich, B.J., Campbell, A.A., Fryxell, G.E., Graff, G.L., Song, L., Liu, J., Virden, W., McVay, G.L., Ceramic thin film formation on functionalized interfaces through biomimetic processing. Science 1994, 264, 48-55.
Hjerten, S.; Levin, O.; Tiselius, A., Protein chromatography on calcium phosphate columns. Arch Biochem Biophys 1956, 65, (1), 132-55.
Schroder, E.; Jonsson, T.; Poole, L., Hydroxyapatite chromatography: altering the phosphate-dependent elution profile of protein as a function of pH. Anal Biochem 2003, 313, (1), 176-8.
Matsumoto, T.; Okazaki, M.; Inoue, M.; Yamaguchi, S.; Kusunose, T.; Toyonaga, T.; Hamada, Y.; Takahashi, J., Hydroxyapatite particles as a controlled release carrier of protein. Biomaterials 2004, 25, (17), 3807-12.
Centrella, M.; McCarthy, T. L.; Canalis, E., Skeletal tissue and transforming growth factor beta. Faseb J 1988, 2, (15), 3066-73.
Gorski, J. P., Is all bone the same? Distinctive distributions and properties of non-collagenous matrix proteins in lamellar vs. woven bone imply the existence of different underlying osteogenic mechanisms. Crit Rev Oral Biol Med 1998, 9, (2), 201-23.
Gorski, J. P.; Griffin, D.; Dudley, G.; Stanford, C.; Thomas, R.; Huang, C.; Lai, E.; Karr, B.; Solursh, M., Bone acidic glycoprotein-75 is a major synthetic product of osteoblastic cells and localized as 75- and/or 50-kDa forms in mineralized phases of bone and growth plate and in serum. J Biol Chem 1990, 265, (25), 14956-63.
Peret, B. J.; Murphy, W. L., Controllable soluble protein concentration gradients in hydrogel networks. Advanced Functional Materials 2008, 18, 3410-3417.
Murphy, W.; Mooney, D., Biomineralization via bioinspired variation in polymer surface chemistry. Abstracts of Papers of the American Chemical Society 2001, 222, U344.
Ngankam, P. A., Lavalle, P., Voegel, J.C., et al., Influence of polyelectrolyte multilayer films on calcium phosphate nucleation. Journal of the American Chemical Society 2000, 122, 8998-9005.
Yoshikawa, et al., "Effects of local administration of vascular endothelial growth factor on mechanical characteristics of the semitendinosus tendon graft after anterior cruciate ligament reconstruction in sheep," Am. J. Sports Med., 2006, vol. 34(12), p. 1918-25.
Rodeo, et al., "Use of recombinant human bone morphogenetic protein-2 to enhance tendon healing in a bone tunnel," Am. J. Sports Med., 1999, vol. 27 (4), p. 476-88.
Taguchi, T.; Kishida, A.; Akashi, M., Apatite formation on/in hydrogel matrices using an alternate soaking process: II. Effect of swelling ratios of poly(vinyl alcohol) hydrogel matrices on apatite formation. J Biomater Sci Polym Ed 1999, 10, (3), 331-9.
Taguchi, T.; Shiraogawa, M.; Kishida, A.; Akashi, M., A study on hydroxyapatite formation on/in the hydroxyl groups-bearing nonionic hydrogels. J Biomater Sci Polym Ed 1999, 10, (1), 19-32.
ASTM Standard C633-79: Standard test method for adhesion or cohesive strength of flame-sprayed coatings. In; ASTM: 1993; pp. 652-656.
Sun, L.; Berndt, C. C.; Gross, K. A.; Kucuk, A., Material fundamentals and clinical performance of plasma-sprayed hydroxyapatite coatings: a review. J Biomed Mater Res 2001, 58, (5), 570-92.
Murphy, W.; Messersmith, P., Compartmental control of mineral formation: adaptation of a biomineralization strategy for biomedical use. Polyhedron 2000, 19, (3), 357-363.
Elliott, J., Structure and Chemistry of Apatites and other Calcium Orthophosphates. Elsevier: Amsterdam, 1994.
Leung, D. W.; Cachianes, G.; Kuang, W. J.; Goeddel, D. V.; Ferrara, N., Vascular endothelial growth factor is a secreted angiogenic mitogen. Science 1989, 246, (4935), 1306-9.
Petryk, A.; Shimmi, O.; Jia, X.; Carlson, A. E.; Tervonen, L.; Jarcho, M. P.; O'Connor M, B.; Gopalakrishnan, R., Twisted gastrulation

(56) References Cited

OTHER PUBLICATIONS and chordin inhibit differentiation and mineralization in MC3T3-E1 osteoblast-like cells. Bone 2005, 36, (4), 617-26.
Lee, Y. C.; Yang, D., Determination of lysozyme activities in a microplate format. Anal Biochem 2002, 310, (2), 223-4.
Raiche, A. T.; Puleo, D. A., Modulated release of bioactive protein from multilayered blended PLGA coatings. Int J Pharm 2006, 311, (1-2), 40-9.
Lu, Y.; Markel, M. D.; Nemke, B.; Wynn, S.; Graf, B. K., Comparison of Single vs. Double-Tunnel Tendon-to-Bone Healing in an Ovine Model: A Biomechanical and Histological Analysis. Am J Sports Med 2009, 37, (3), 512-517.
Barber, F. A.; Herbert, M. A.; Coons, D. A.; Boothby, M. H., Sutures and suture anchors—update 2006. Arthroscopy 2006, 22, (10), 1063-69.
Wright, P. B.; Budoff, J. E.; Yeh, M. L.; Kelm, Z. S.; Luo, Z. P., Strength of damaged suture: an in vitro study. Arthroscopy 2006, 22, (12), 1270-1275 e3.
Wust, D. M.; Meyer, D. C.; Favre, P.; Gerber, C., Mechanical and handling properties of braided polyblend polyethylene sutures in comparison to braided polyester and monofilament polydioxanone sutures. Arthroscopy 2006, 22, (11), 1146-53.
Bodde, E. W.; Wolke, J. G.; Kowalski, R. S.; Jansen, J. A., Bone regeneration of porous beta-tricalcium phosphate (Conduit TCP) and of biphasic calcium phosphate ceramic (Biosel) in trabecular defects in sheep. J Biomed Mater Res A 2007, 82, (3), 711-22.
Rodeo, S.; Kawamura, S.; Ma, C.; Deng, X.; Sussman, P.; Hays, P.; Ying, L., The effect of osteoclastic activity on tendon-to-bone healing: An experimental study in rabbits. Journal of Bone and Joint Surgery-American vol. 2007, 89A, (10), 2250-2259.
Frisch, T.; Sorensen, M. S.; Overgaard, S.; Lind, M.; Bretlau, P., Volume-referent bone turnover estimated from the interlabel area fraction after sequential labeling. Bone 1998, 22, (6), 677-82.
Miller, S. C.; Pan, H.; Wang, D.; Bowman, B. M.; Kopeckova, P.; Kopecek, J., Feasibility of using a bone-targeted, macromolecular delivery system coupled with prostaglandin E(1) to promote bone formation in aged, estrogen-deficient rats. Pharm Res 2008, 25, (12), 2889-95.
Markel, M. D.; Wikenheiser, M. A.; Chao, E. Y., A study of fracture callus material properties: relationship to the torsional strength of bone. J Orthop Res 1990, 8, (6), 843-50.
Min Lu, et al., "Partitioning of proteins and thylakoid membrane vesicles in aqueous two-phase systems with hydrophobically modified dextran," Journal of Chromatography A, 1994, vol. 668, pp. 215-228.
Helal, R., et al., "Determination of lysozyme activity by a fluorescence technique in comparison with the classical turbidity assay," Pharmazie, 2008, vol. 63, pp. 415-419.
Jongpaiboonkit et al., "Mineral-Coated Polymer Microspheres for Controlled Protein Binding and Release", Advanced Materials, 2009, 21, pp. 1-4.
Liu, Y.; de Groot, K.; Hunziker, E. B., Osteoinductive implants: the mise-en-scene for drug-bearing biomimetic coatings. Ann Biomed Eng 2004, 32, (3), 398-406.
Sogo, Y.; Ito, A.; Onoguchi, M.; Oyane, A.; Tsurushima, H.; Ichinose, N., Formation of a FGF-2 and calcium phosphate composite layer on a hydroxyapatite ceramic for promoting bone formation. Biomed Mater 2007, 2, (3), S175-80.
Lowenstam, H. A, Weiner, S., On Biomineralization. Oxford University Press: Oxford, 1989.
Murphy, et al., "Healing of Bone and Connective Tissues," in Encyclopedia of Biomaterials and Biomedical Engineering, Wnek, G.B., ed., Informa Healthcare, 2006.
Kohno, et al., "Immunohistochemical demonstration of growth factors at the tendon-bone interface in anterior cruciate ligament reconstruction using a rabbit model," J. Orthop. Sci., 2007, vol. 12(1) p. 67-73.
Yang et al. (1981). Growth of Human Mammary Epithelial Cells on Collagen Gel Surfaces. Cancer Research, v41, p. 4093-4100.
Amit et al. (2000). Clonally Derived Human Embryonic Stem Cell Lines Maintain Pluripotency and Proliferative Potential for Prolonged Periods of Culture. Developmental Biology, v227, p. 271-278.
Michalopoulos et al. (1975). Primary culture of parenchymal liver cells on collagen membranes: Morphological and biochemical observations Experimental Cell Research, v94(1), p. 70-78—Abstract only.
Ponticos et al. (2004). Regulation of Collagen Type I in Vascular Smooth Muscle Cells by Competition between Nkx2.5 and deltaEF1/ZEB1. Molecular and Cellular Biology, v24(14), p. 6151-6161.
Keller et al. (2011). The bending of cell sheets—from folding to rolling. BMC Biology, v9(90), 4 pages.
Markel, M. D.; Wikenheiser, M. A.; Chao, E. Y., Formation of bone in tibial defects in a canine model. Histomorphometric and biomechanical studies. J Bone Joint Surg Am 1991, 73, (6), 914-23.
Zabka, A.; Pluhar, G.; Edwards, R.; Manley, P.; Hayashi, K.; Heiner, J.; Kalscheur, V.; Seeherman, H.; Markel, M., Histomorphometric description of allograft bone remodeling and union in a canine segmental femoral defect model: a comparison of rhBMP-2, cancellous bone graft, and absorbable collagen sponge. Journal of Orthopaedic Research 2001, 19, (2), 318-327.
Edwards, R.; Seeherman, H.; Bogdanske, J.; Devitt, J.; Vanderby, P.; Markel, M., Percutaneous injection of recombinant human bone morphogenetic protein-2 in a calcium phosphate paste accelerates healing of a canine tibial osteotomy. Journal of Bone and Joint Surgery-American vol. 2004, 86A, (7), 1425-1438.
Walsh, W. R.; Cotton, N. J.; Stephens, P.; Brunelle, J. E.; Langdown, A.; Auld, J.; Vizesi, F.; Bruce, W., Comparison of poly-L-lactide and polylactide carbonate interference screws in an ovine anterior cruciate ligament reconstruction model. Arthroscopy 2007, 23, (7), 757-65, 765 e1-2.
International Search Report and Written Opinion for PCT/US2010/042312, dated Nov. 4, 2010, 17 pages.
Crane, G. M.; Ishaug, S. L.; Mikos, A. G., Bone tissue engineering. Nat Med 1995, 1, (12), 1322-4.
Mann, S., Ozin, G.A., Synthesis of inorganic materials with complex form. Nature 1996, 382, 313-318.
Statistics, Table 94, Ambulatory and inpatient procedures according to place, sex, age, and type of procedure: United States, 1994-1998. U.S. Department of Health and Human Services: Hyattsville, MD, 2000.
Sarikaya, M., Biomimetics: materials fabrication through biology. Proc Natl Acad Sci U S A 1999, 96, (25), 14183-5.
Linn, R. M.; Fischer, D. A.; Smith, J. P.; Burstein, D. B.; Quick, D. C., Achilles tendon allograft reconstruction of the anterior cruciate ligament-deficient knee. Am J Sports Med 1993, 21, (6), 825-31.
Buelow, J. U.; Siebold, R.; Ellermann, A., A new bicortical tibial fixation technique in anterior cruciate ligament reconstruction with quadruple hamstring graft. Knee Surg Sports Traumatol Arthrosc 2000, 8, (4), 218-25.
Kimura, Y.; Hokugo, A.; Takamoto, T.; Tabata, Y.; Kurosawa, H., Regeneration of anterior cruciate ligament by biodegradable scaffold combined with local controlled release of basic fibroblast growth factor and collagen wrapping. Tissue Eng Part C Methods 2008, 14, (1), 47-57.
Demirag, B.; Sarisozen, B.; Ozer, O.; Kaplan, T.; Ozturk, C., Enhancement of tendon-bone healing of anterior cruciate ligament grafts by blockage of matrix metalloproteinases. J Bone Joint Surg Am 2005, 87, (11), 2401-10.
Saltzman, W. M.; Olbricht, W. L., Building drug delivery into tissue engineering. Nat Rev Drug Discov 2002, 1, (3), 177-86.
Cohen, S.; Yoshioka, T.; Lucarelli, M.; Hwang, L. H.; Langer, R., Controlled delivery systems for proteins based on poly(lactic/glycolic acid) microspheres. Pharm Res 1991, 8, (6), 713-20.
Langer, R., New methods of drug delivery. Science 1990, 249, (4976), 1527-33.
Langer, R.; Folkman, J., Polymers for the sustained release of proteins and other macromolecules. Nature 1976, 263, (5580), 797-800.

(56) References Cited

OTHER PUBLICATIONS

Langer, R.; Moses, M., Biocompatible controlled release polymers for delivery of polypeptides and growth factors. J Cell Biochem 1991, 45, (4), 340-5.

Leong, K. W.; Kost, J.; Mathiowitz, E.; Langer, R., Polyanhydrides for controlled release of bioactive agents. Biomaterials 1986, 7, (5), 364-71.

Pekarek, K. J.; Jacob, J. S.; Mathiowitz, E., Double-walled polymer microspheres for controlled drug release. Nature 1994, 367, (6460), 258-60.

Lee, K. Y.; Peters, M. C.; Anderson, K. W.; Mooney, D. J., Controlled growth factor release from synthetic extracellular matrices. Nature 2000, 408, (6815), 998-1000.

Tabata, Y.; Ikada, Y., Vascularization effect of basic fibroblast growth factor released from gelatin hydrogels with different biodegradabilities. Biomaterials 1999, 20, (22), 2169-75.

Sullivan, F. a., U.S. Drug Delivery Technology Markets. Frost and Sullivan: 2001.

Murphy, W. L.; Peters, M. C.; Kohn, D. H.; Mooney, D. J., Sustained release of vascular endothelial growth factor from mineralized poly(lactide-co-glycolide) scaffolds for tissue engineering. Biomaterials 2000, 21, (24), 2521-7.

Murphy, W. L.; Simmons, C. A.; Kaigler, D.; Mooney, D. J., Bone regeneration via a mineral substrate and induced angiogenesis. J Dent Res 2004, 83, (3), 204-10.

Sheridan, M. H.; Shea, L. D.; Peters, M. C.; Mooney, D. J., Bioabsorbable polymer scaffolds for tissue engineering capable of sustained growth factor delivery. J Control Release 2000, 64, (1-3), 91-102.

Howdle, S. M. W., M.S.; Whitaker, M.J.; Popov, M.C.; Davies, M.C.; Mandel, F.S.; Wang, J.D.; Shakesheff, K.M., Supercritical fluid mixing: preparation of thermally sensitive polymer composites containing bioactive materials. Chemical Communications 2001, 1, (109-110).

Yang, X. B.; Green, D. W.; Roach, H. I.; Clarke, N. M.; Anderson, H. C.; Howdle, S. M.; Shakesheff, K. M.; Oreffo, R. O., Novel osteoinductive biomimetic scaffolds stimulate human osteoprogenitor activity—implications for skeletal repair. Connect Tissue Res 2003, 44 Suppl 1, 312-7.

Richardson, T. P.; Peters, M. C.; Ennett, A. B.; Mooney, D. J., Polymeric system for dual growth factor delivery. Nat Biotechnol 2001, 19, (11), 1029-34.

Zisch, A. H.; Schenk, U.; Schense, J. C.; Sakiyama-Elbert, S. E.; Hubbell, J. A., Covalently conjugated VEGF—fibrin matrices for endothelialization. J Control Release 2001, 72, (1-3), 101-13.

Raiche, A. T.; Puleo, D. A., Cell responses to BMP-2 and IGF-I released with different time-dependent profiles. J Biomed Mater Res 2004, 69A, (2), 342-50.

Raiche, A. T.; Puleo, D. A., In vitro effects of combined and sequential delivery of two bone growth factors. Biomaterials 2004, 25, (4), 677-85.

Alt, V.; Pfefferle, H. J.; Kreuter, J.; Stahl, J. P.; Pavlidis, T.; Meyer, C.; Mockwitz, J.; Wenisch, S.; Schnettler, R., Effect of glycerol-L-lactide coating polymer on bone ingrowth of bFGF-coated hydroxyapatite implants. J Control Release 2004, 99, (1), 103-11.

Mann, S.; Archibald, D.D.; Didymus, J.M., et al., Crystallization and inorganic-organic interfaces—biominerals and biomimetic synthesis. Science 1993, 261, 1286-1292.

Hossain, M.; Irwin, R.; Baumann, M. J.; McCabe, L. R., Hepatocyte growth factor (HGF) adsorption kinetics and enhancement of osteoblast differentiation on hydroxyapatite surfaces. Biomaterials 2005, 26, (15), 2595-602.

Liu, Y.; Hunziker, E. B.; Layrolle, P.; De Bruijn, J. D.; De Groot, K., Bone morphogenetic protein 2 incorporated into biomimetic coatings retains its biological activity. Tissue Eng 2004, 10, (1-2), 101-8.

Ripamonti, U.; Yeates, L.; van den Heever, B., Initiation of heterotopic osteogenesis in primates after chromatographic adsorption of osteogenin, a bone morphogenetic protein, onto porous hydroxyapatite. Biochem Biophys Res Commun 1993, 193, (2), 509-17.

Sumner, D. R.; Turner, T. M.; Urban, R. M.; Virdi, A. S.; Inoue, N., Additive enhancement of implant fixation following combined treatment with rhTGF-beta2 and rhBMP-2 in a canine model. J Bone Joint Surg Am 2006, 88, (4), 806-17.

Zambonin, G.; Grano, M.; Greco, G.; Oreffo, R. O.; Triffit, J. T., Hydroxyapatite coated with insulin-like growth factor 1 (IGF1) stimulates human osteoblast activity in vitro. Acta Orthop Scand 1999, 70, (2), 217-20.

Bajpai, P. K.; Benghuzzi, H. A., Ceramic systems for long-term delivery of chemicals and biologicals. J Biomed Mater Res 1988, 22, (12), 1245-66.

Feng, B.; Chen, J.; Zhang, X., Interaction of calcium and phosphate in apatite coating on titanium with serum albumin. Biomaterials 2002, 23, (12), 2499-507.

Zeng, H.; Chittur, K. K.; Lacefield, W. R., Analysis of bovine serum albumin adsorption on calcium phosphate and titanium surfaces. Biomaterials 1999, 20, (4), 377-84.

Zhang, R.; Xu, D.; Landeryou, T.; Toth, C.; Dimaano, N.; Berry, J.; Evans, J.; Hawkins, M., Ectopic bone formation using osteogenic protein-1 carried by a solution precipitated hydroxyapatite. J Biomed Mater Res A 2004, 71, (3), 412-8.

Liu, Y.; Hunziker, E. B.; Randall, N. X.; de Groot, K.; Layrolle, P., Proteins incorporated into biomimetically prepared calcium phosphate coatings modulate their mechanical strength and dissolution rate. Biomaterials 2003, 24, (1), 65-70.

Luong, L. N.; Hong, S. I.; Patel, R. J.; Outslay, M. E.; Kohn, D. H., Spatial control of protein within biomimetically nucleated mineral. Biomaterials 2006, 27, (7), 1175-86.

Yu, X.; Qu, H.; Knecht, D. A.; Wei, M., Incorporation of bovine serum albumin into biomimetic coatings on titanium with high loading efficacy and its release behavior. J Mater Sci Mater Med 2009, 20, (1), 287-94.

Azevedo, H.; Leonor, I.; Alves, C.; Reis, R., Incorporation of proteins and enzymes at different stages of the preparation of calcium phosphate coatings on a degradable substrate by a biomimetic methodology. Materials Science & Engineering C 2005, 25, (2), 169-179.

Jayasuriya, A. C.; Shah, C., Controlled release of insulin-like growth factor-1 and bone marrow stromal cell function of bone-like mineral layer-coated poly(lactic-co-glycolic acid) scaffolds. J Tissue Eng Regen Med 2008, 2, (1), 43-9.

Leonor, I.; Azevedo, H.; Reis, R., Effects of protein incorporation on calcium phosphate coating. Materials Science & Engineering C 2009, pp. 913-918.

Murphy, et al., "Bioinspired Growth of Crystalline Carbonate Apatite on Biodegradable Polymer Substrata", J. Am. Chem. Soc., 2002, vol. 124, p. 1910-1917.

* cited by examiner

Green = Oct3/4
Red = Nanog
Blue = nucleus

Day 0

Green = Oct3/4
Red = Nanog
Blue = nucleus

Day 1

Green = Oct3/4
Red = Nanog
Blue = nucleus

Day 2

Green = Oct3/4
Red = Nanog
Blue = nucleus

Day 3

All

Oct4

Nucleus

Nanog

All

Oct4

Nucleus

Nanog

All

Oct4

Nucleus

Nanog

All

Oct4

Nucleus

Nanog

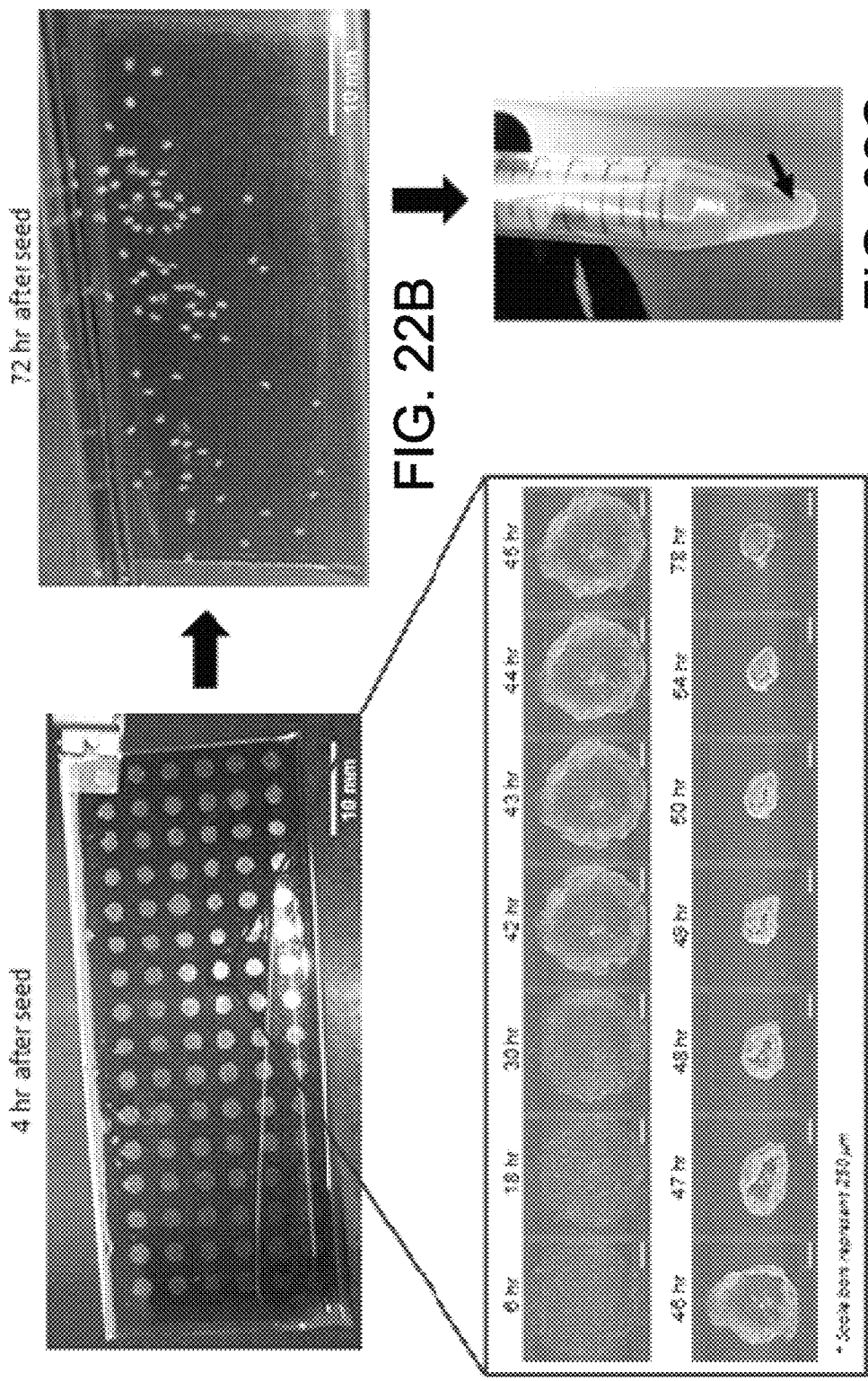

CHEMICALLY LABILE PEPTIDE-PRESENTING SURFACES FOR CELLULAR SELF-ASSEMBLY

CROSS-REFERENCE TO RELATED APPLICATION

This application is a continuation-in-part application of U.S. patent application Ser. No. 13/835,102, filed Mar. 15, 2013, which is hereby incorporated by reference in its entirety.

STATEMENT OF GOVERNMENT SUPPORT

This invention was made with government support under EB005374, HL093282, and TR000506 awarded by the National Institutes of Health. The government has certain rights in the invention.

INCORPORATION OF SEQUENCE LISTING

A paper copy of the Sequence Listing and a computer readable form of the Sequence Listing containing the file named "P150062US0128 (243-189)_ST25.txt", which is 2,152 bytes in size (as measured in MICROSOFT WINDOWS® EXPLORER), are provided herein and are herein incorporated by reference. This Sequence Listing consists of SEQ ID NOs: 1-9.

BACKGROUND OF THE DISCLOSURE

The present disclosure relates generally to the culture of stem cells. More particularly, the present disclosure relates to cell culture methods for generating colonies of stem cells having controlled size.

The substrate on which cells are cultured is important for successful cellular growth and tissue generation. For example, it has been demonstrated that attachment to the substrate by human embryonic stem cells may contribute to the variability in whether the cells remain undifferentiated or undergo differentiation.

Many protocols for differentiation of pluripotent stem cells begin with the formation of 3-dimensional aggregates of cells called embryoid bodies (EBs). Methods for forming embryoid bodies involve techniques such as scraping adherent ES cell and induced pluripotent stem cell cultures and mild treatment with proteases such as trypsin and/or dispase to release large clumps of cells, followed by placing the resulting aggregates in non-adherent suspension culture. The aggregates formed using these methods are heterogeneous in size and shape, which can lead to inefficient and uncontrolled differentiation. Aggregate size can also directly affect subsequent differentiation pathways. To address these issues, cell culture substrates such as multi-well plates with wells having defined widths have been developed. Another method creates dots of a substrate material such as Matrigel® onto the surface of a plate.

Self-assembled monolayers ("SAMs") in array formats (i.e., SAM arrays) have been constructed that present ligands to cells plated onto the array. A SAM array is an organized layer of amphiphilic molecules in which one end of the molecule exhibits a specific, reversible affinity for a substrate and the other end of the molecule has a functional group. Because the molecule used to form the SAM array is polarized, the hydrophilic "head groups" assemble together on the substrate, while the hydrophobic tail groups assemble far from the substrate. Areas of close-packed molecules nucleate and grow until the surface of the substrate is covered in a single monolayer. The use of alkanethiols to construct SAM arrays allow for the formation of reproducible SAM arrays and surfaces. SAM arrays may be used to identify specific ligands or epitopes that promote cellular attachment, spreading, proliferation, migration and differentiation, as well as for modulating these cellular activities differentially on each spot on the same SAM array.

Aggregate size and shape can also directly affect subsequent differentiation pathways and lead to inefficient and uncontrolled differentiation. Accordingly, there exists a need for alternative substrates and methods to control the size and/or shape of colonies as well as avoid treatments such as scraping and enzymes used to harvest the cell aggregates.

SUMMARY OF THE DISCLOSURE

The present disclosure relates generally to the culture of cells. More particularly, the present disclosure relates to cell culture methods for generating colonies of cells having controlled size. It has been found that cell colony size may be controlled in cell culture via SAM arrays with controlled spot size.

In one aspect, the present disclosure is directed to a method of controlling the formation of a cell culture aggregate. The method comprises: forming at least one alkanethiolate self-assembled monolayer ("SAM") spot of a self-assembled monolayer array, wherein the alkanethiolate self-assembled monolayer spot comprises a cellular adhesive peptide immobilized using a labile covalent bond; culturing a cell on the alkanethiolate self-assembled monolayer spot for a sufficient time to form a confluent monolayer of cells; and detaching the confluent monolayer of cells. The method can further comprise culturing the confluent monolayer for a sufficient time to allow the monolayer to invaginate.

In another aspect, the present disclosure is directed to a method of preparing a cell aggregate of a uniform size. The method comprises: forming at least one alkanethiolate self-assembled monolayer ("SAM") spot of a specified diameter of a self-assembled monolayer array, wherein the alkanethiolate self-assembled monolayer spot comprises a cellular adhesive peptide immobilized using a labile covalent bond; culturing a cell on the alkanethiolate self-assembled monolayer array spot for a sufficient time to form a confluent monolayer of cells; detaching the confluent monolayer of cells; and collecting the confluent monolayer of cells.

In another aspect, the present disclosure is directed to a method of preparing a cell aggregate of a specified shape. The method comprises: forming at least one alkanethiolate self-assembled monolayer ("SAM") spot of a specified shape of a self-assembled monolayer array, wherein the alkanethiolate self-assembled monolayer spot comprises a cellular adhesive peptide immobilized using a labile covalent bond; culturing a cell on the self-assembled monolayer array spot for a sufficient time to form a confluent monolayer of cells; detaching the confluent monolayer of cells; and collecting the confluent monolayer of cells.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The disclosure will be better understood, and features, aspects and advantages other than those set forth above will become apparent when consideration is given to the following detailed description thereof. Such detailed description makes reference to the following drawings, wherein:

FIG. 3B depicts invagination of circle-shaped hESC monolayers.

FIG. 3D depicts invagination of oval and cross-shaped hESC monolayers.

(FIG. 10B) non-labile (e.g., amide) bonds between the peptide and the SAM.

FIG. 18A depicts traces demonstrating change in population area over time for hESCs cultured on SAMs presenting cyclo(RGDF$_D$C) (SEQ ID NO:4) at 0.01%, 0.5%, and 5% total peptide density. Rate of hESC aggregate self-assembly increased as total peptide density decreased on labile (cyclo(RGDF$_D$C)) (SEQ ID NO:4) SAMs. FIG. 18B depicts hESCs cultured on 0.01%, 0.5%, and 5% cyclo(RGDF$_D$C) (SEQ ID NO:4) SAMs self-assembled with different kinetics. Effect of peptide density on kinetics of self-assembly was concentration-dependent, with conditions of lower peptide density resulting in accelerated self-assembly as quantified by $t_{50}$ of self-assembly. Error bars represent standard error, represented at 95% confidence interval. Asterisks denote statistical significance between indicated conditions (Student's t-test, p<0.001).

FIG. 20A depicts traces demonstrating change in population area over time for hESCs cultured on 5% cyclo(RGDF$_D$C) (SEQ ID NO:4) SAMs in the presence or absence of adhesion-blocking antibody. Rate of hESC aggregate self-assembly increases in conditions with the addition of $\alpha_v$ integrin-blocking antibody, in comparison to control conditions without antibody on 5% (cyclo(RGDF$_D$C)) (SEQ ID NO:4) SAMs. FIG. 20B depicts that adhesion dependence of self-assembly behavior is further validated by quantification of $t_{50}$ of self-assembly, where conditions in which $\alpha_v$ integrin-mediated adhesion is blocked lead to drastic decreases in $t_{50}$ (i.e., increases in rate of self-assembly) compared to controls in which no antibody was added. Error bars represent standard error, represented at 95% confidence interval. Asterisks denote statistical significance between indicated conditions (Student's t-test, p<0.05).

FIGS. 22A-22C depict that labile SAM arrays enable large-scale generation of embryoid bodies (EB). FIG. 22A depicts an image of 1.2 mm-diameter patterned circular SAM arrays presenting cyclo(RGDF$_D$C) (SEQ ID NO:4) peptide at 4 hours after initial seeding. FIG. 22B depicts the resulting EBs formed hESC after self-assembly (72 hours). FIG. 22C shows that the resulting EBs are easily collected (black arrow).

FIG. 25A depicts immunofluorescent staining of hESCs on 5% cyclo(RGDF$_D$C) (SEQ ID NO:4) SAMs and demonstrates that hESCs largely retain Oct4 and Nanog expression at 4 hours and 24 hours after seeding, prior to the beginning of aggregate self-assembly. FIG. 25B depicts quantification of immunofluorescence stains and indicates that high levels of Oct4 and Nanog expression (~90% Nanog$^+$ and >90% Oct4$^+$) at 4 hours are not significantly diminished by 24 hours on cyclo(RGDF$_D$C) (SEQ ID NO:4) SAMs. Error bars represent ±1 standard deviation.

FIG. 28A depicts traces demonstrating change in population area over time for hESCs or hMSCs cultured on 5% cyclo(RGDF$_D$C) (SEQ ID NO:4) SAMs. FIG. 28B depicts that cell type-dependent kinetics of the self-assembly process are further demonstrated, with hMSCs exhibiting a much quicker $t_{50}$ than hESCs. Furthermore, the small error associated with $t_{50}$ of hMSCs suggests that the hMSC self-assembly process occurs consistently within a very narrow time frame. Error bars represent standard error at 95% confidence interval. Asterisks denote statistical significance between indicated conditions (Student's t-test, p<0.05).

FIG. 29A depicts that inhibition of cellular actin-myosin contractility via treatment with Y-27632 (a ROCK inhibitor) is sufficient to delay both the onset and completion of hMSC self-assembly. FIG. 29B depicts that inhibition of cellular actin-myosin contractility via treatment with Y-27632 influences the kinetics of hMSC self-assembly in a concentration-dependent manner, as demonstrated by the increase in $t_{50}$ (i.e., decrease in rate of self-assembly) with increasing concentrations of Y-27632. Error bars represent standard error at 95% confidence interval. Asterisks denote statistical significance between indicated conditions (Student's t-test, p<0.05).

Figure 1:
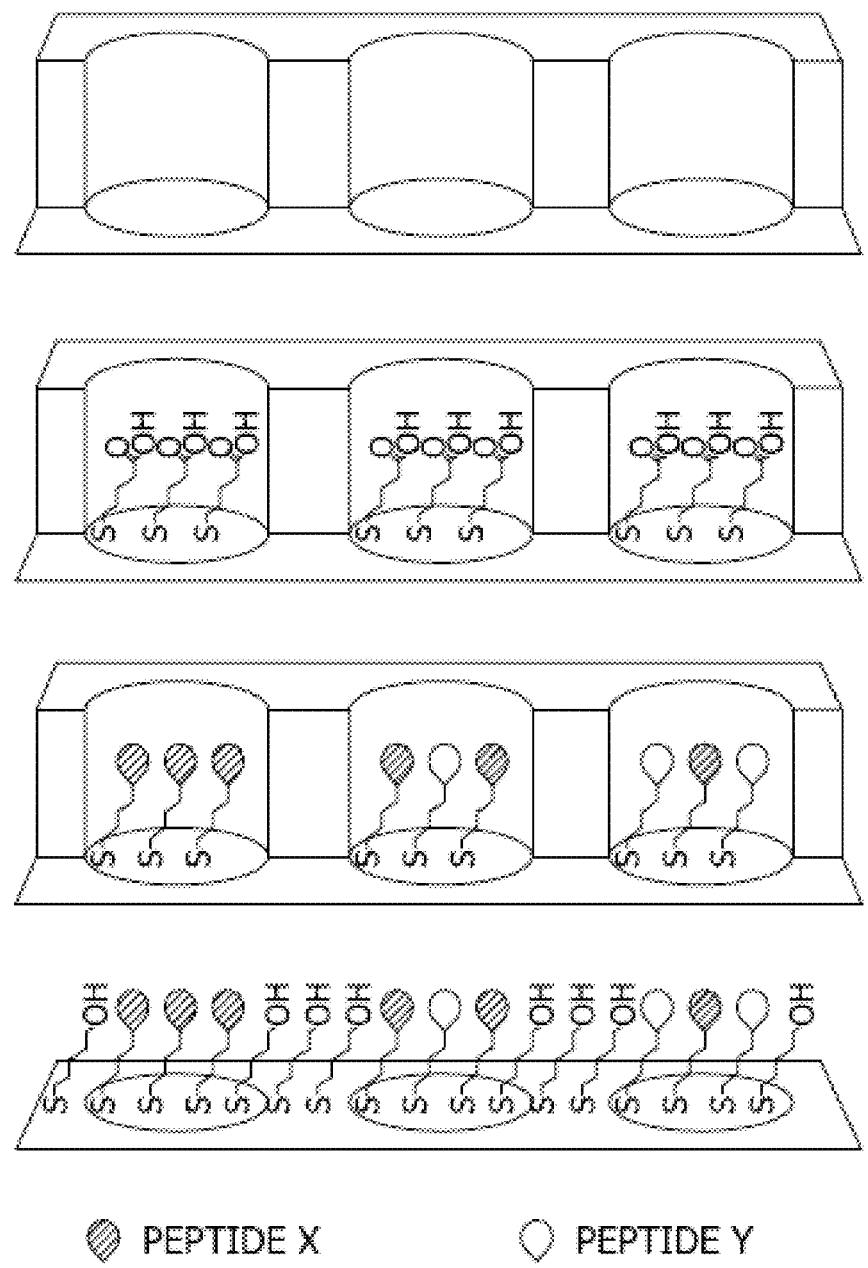
FIG. 1 is a schematic illustrating the steps for preparing a self-assembled monolayer array used in one embodiment of the methods of the present disclosure.

While the disclosure is susceptible to various modifications and alternative forms, specific embodiments thereof have been shown by way of example in the drawings and are herein described below in detail. It should be understood, however, that the description of specific embodiments is not intended to limit the disclosure to cover all modifications, equivalents and alternatives falling within the spirit and scope of the disclosure as defined by the appended claims.

DETAILED DESCRIPTION

Unless defined otherwise, all technical and scientific terms used herein have the same meaning as commonly understood by one of ordinary skill in the art to which the disclosure belongs. Although any methods and materials similar to or equivalent to those described herein may be used in the practice or testing of the present disclosure, the preferred materials and methods are described below.

In accordance with the present disclosure, methods for preparing colonies of stem cells with controlled size and/or shape have been discovered. More particularly, the present disclosure relates to methods for preparing stem cell colonies with controlled size and/or shape using SAM arrays. It has been found that stem cell colony size and/or shape may be controlled in cell culture via SAM arrays with controlled spot size and/or shape.

In one aspect, the present disclosure is directed to a method of controlling the formation of a cell culture aggregate. The method comprises culturing a cell on a spot (also referred to herein as "an array spot") of a self-assembled monolayer ("SAM") array for a sufficient time to form a confluent monolayer of cells and detaching the confluent monolayer of cells. As known by those skilled in the art, the initial density of the cells can influence the time to confluence. A particularly suitable seeding density can be, for example, $10^5$ cells/cm$^2$, in which cells can reach confluence in a range of between about 12 hours to about 36 hours. A particularly suitable time period after which cells can be detached can be, for example, about 6 hours to about 144 hours, including about 36 hours to about 84 hours. More particularly, for $10^5$ cells/cm$^2$, cells can be detached at a time period of from about 36 hours to about 60 hours after initial seeding. For larger colonies such as, for example, an area greater than about 7 mm$^2$, detachment can require up to about 84 hours.

The method may further comprise culturing the confluent monolayer for a sufficient time to allow the monolayer to invaginate. As used herein, "invaginate" or "invagination" or "invaginating" refer to the monolayer lifting from the surface of the SAM array and folding into a cell aggregate (also referred to herein, as self-assembly of cell aggregates).

Without being bound by theory, it is believed that, in one embodiment, the self-assembly of cell aggregates relies on the formation of a labile covalent bond between a terminal group of an alkanethiolate self-assembled monolayer spot of the SAM array and a cell adhesion peptide side chain to be immobilized on the spot as described more fully below. In one embodiment, as used herein, "labile" chemistry refers to a combination of alkanethiol(s) and peptide(s) that likely result in formation of a hydrolysis-labile linkage between the peptide(s) and the SAM spot. Since carboxylic acid groups provide the reactive functionality on the SAM spots in question, a hydrolysis-labile linkage between the peptide and the SAM spot may be formed if, for example, the peptide in question contains a free thiol as its only potential nucleophile, whereby successful coupling of the peptide to the SAM spot results in a relatively labile thioester bond (see FIG. 10A, wherein the peptide in question is cyclo(RGD-F$_D$C; "F$_D$" denotes D-phenylalanine) (SEQ ID NO: 4).

Figures 10A, 10B:
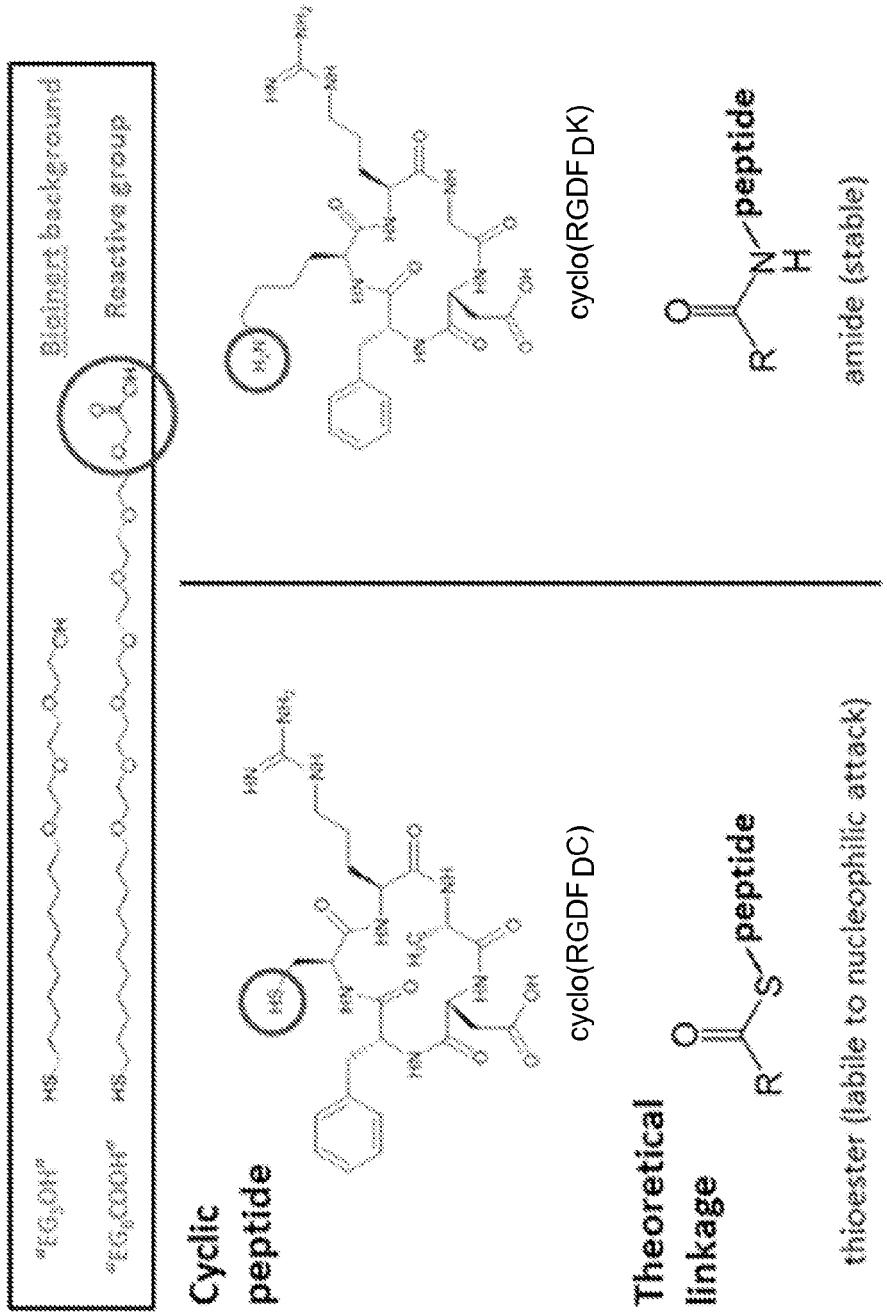
FIGS. 10A and 10B depict examples of peptide ligands that may covalently couple to carboxylic acid-terminated alkanethiol SAMs to form (FIG. 10A) labile.

A non-labile linkage between peptide and SAM spot may be formed if, for example, the peptide in question contains a free amine as its only nucleophile, whereby successful coupling of the peptide to the SAM spot results in a relatively stable amide bond (see FIG. 10B, wherein the peptide in question is cyclo(RGDF$_D$K) (SEQ ID NO: 7).

In one embodiment, cleavage of the labile bond, particularly, by nucleophilic attack, allows for release of the peptide from the SAM surface, allowing for cellular aggregate self-assembly. Unlike conventional SAM array technologies that are limited by dependence on highly specific enzymes and cleavable groups or mechanical manipulation, the cell aggregate self-assembly of this embodiment allows the array to be broadly applicable to any peptide containing an amino acid side chain capable of forming a labile bond (e.g., thioester bond) with the SAM array surface. Accordingly, this SAM array format has potential use to sort/enrich cell types differentiated from stem cells, based on selective release of labile peptides with particular affinity for cell surface markers of the cell type(s) of interest. Finally, the array format enables utilization as a platform for screening key parameters that influence cell aggregate self-assembly, stem cell differentiation, and microtissue/organoid formation processes.

Since the labile chemistry referred to herein relates to its use to promote a cellular self-assembly process, the concepts presented here may be extended to any chemical bond that has the potential to be labile within an environment that supports cell culture (i.e., physiologically relevant temperatures and ionic strengths, under aqueous conditions), over time frames associated with cell culture (typically hours to years). In particular, this may include chemical bonds that are labile to hydrolysis or nucleophilic attack in aqueous conditions. Such bonds may be formed here by any combination of alkanethiol(s) and cell-interactive molecule(s) (e.g., cell adhesion peptides) that result in formation of a hydrolysis-labile or nucleophile-labile linkage between the peptide(s) and the SAM. Under typical physiological conditions as described above, such bonds commonly include ester, thioester, acetal, and anhydride groups, as well as other carbonyl derivatives. Thus, the strategies presented here may apply to alkanethiol molecules with any terminal functional group that reacts with an appropriate nucleophile to form such a bond.

Aside from water, exemplary nucleophiles that could be used to break labile bonds include molecules with functional groups that are commonly appropriate nucleophiles under conditions of physiologically relevant temperature and pH, such as deprotonated primary and secondary amines, thiolates, and alkoxides. The likelihood of cleavage of a given labile bond by a given nucleophile depends on nucleophile identity/structure (e.g., pKa of the nucleophilic group), local chemical environment surrounding both labile group and nucleophile, and reaction conditions (e.g., temperature, pH, abundance of nucleophilic species and competing nucleophiles).

In principle, such nucleophiles in biological contexts could originate from side chains or termini of chemically modified or unmodified peptides or proteins. Such nucleophiles could originate from species inherently present in the aqueous culture media, species produced by cells and released into the aqueous culture media, and/or species from exogenous sources added to the aqueous culture media. In theory, these nucleophiles may be non-bioactive and thus serve the purpose of effectively eliminating the bioactive function (e.g., adhesion) of a previously coupled bioactive ligand, or may be bioactive and thus theoretically replace the bioactive function of a previously coupled peptide with a different function.

In addition, the concepts of labile chemistry for cellular self-assembly as presented here may also be applied to the tethering of cell-interactive molecules to self-assembled monolayers that are not based on a combination of alkanethiols on gold. In particular, these concepts may apply to SAMs of alkanethiols on copper, palladium, silver, platinum, and mercury, as well as alloys of these metals. These concepts, in combination with any of the paradigms described above, may also apply to non-alkanethiol SAMs, including alkylsilanes on glass, carboxylic acids on native oxides, and nitriles on platinum.

Further, as SAMs are not restricted to forming on planar surfaces, the present disclosure could also apply to SAMs formed on micro/nanoparticles or other geometric configurations composed of the aforementioned materials.

Because these materials are often amenable to cell culture in both two and three dimensions, the aforementioned types of SAM array systems may allow for cellular self-assembly in two dimensions or in three dimensions, depending on the capabilities of the chosen system.

In one embodiment, invagination of the monolayer can occur at a time of from about 48 hours to about 72 hours when the density of seeded cells is $10^5$ cells/cm$^2$. In another embodiment, invagination of the monolayer can occur at a time of from about 6 hours to about 144 hours, including from about 6 hours to about 72 hours by varying the ligand density from about 2% to about 10%. In another embodiment, invagination of the monolayer can occur at a time of from about 24 hours to about 72 hours by varying the diameter of the array spot size. Suitable array spot diameter size can be from about 600 µm to about 6 mm. A particularly suitable array spot diameter size can be from about 1.2 mm to about 2.4 mm. The method may further comprise collecting the cells after the cells are detached from the SAM array and/or an array spot.

Self-assembled monolayer (SAM) arrays are known in the art. Suitable SAM arrays include patterned SAM arrays. Patterned SAM arrays are those that have been developed to spatially localize ligands to create spatially and chemically-defined spots or islands created to promote cell attachment within the spot. Methods for preparing patterned SAM arrays can be, for example, those prepared by microcontact printing methods, microfluidics approaches, stamping, photochemistry with micro-patterned photomasks, and locally destroying/removing regions of a fully formed SAM and reforming new SAMs in the destroyed regions. Particularly suitable self-assembled monolayer arrays useful for the methods of the present disclosure are those described in U.S. patent application Ser. No. 13/465,120, and incorporated by reference herein in its entirety. Briefly, SAM arrays are prepared by adhering a polymer stencil to a metal-coated substrate. The polymer stencil includes at least one well. A solution of alkanethiolates bearing oligo (ethylene glycol) groups is added to each well of the stencil. Carbodiimide chemistry is used to covalently immobilize at least one cell adhesion peptide to the oligo (ethylene glycol) bearing alkanethiolates. An alkanethiolate self-assembled monolayer spot that presents a cell adhesion peptide is formed on the substrate in each well of the polymer stencil. The polymer stencil is then removed from the substrate to reveal a self-assembled monolayer spot on the substrate. The substrate is then backfilled with hydroxyl terminates alkanethiolates to form a second self-assembled monolayer that surrounds each alkanethiolate self-assembled monolayer spot. Use of alkanethiolate-bearing oligo (ethylene glycol) groups promotes specific protein-surface interactions, while backfilled regions with hydroxyl terminates surrounding each array spot generates an inert surface that prevents and/or hampers protein-surface and cell-surface interactions within the backfilled region.

Once a self-assembled monolayer array is prepared, the method includes contacting ("seeding") a cell with the self-assembled monolayer array. Single cell suspensions can be directly contacted with an array spot. Because of the array features described herein, a single cell suspension solution can also be applied to an entire SAM array. Cells that come in contact with an array spot that presents a surface that promotes cell adhesion and growth will adhere to the array spots, whereas cells that come in contact with the backfilled region will not adhere. After a time sufficient to allow cells to adhere to the array spots (e.g., about 12 hours to 36 hours for $10^5$ cells/cm$^2$), the SAM array can be washed with fresh culture medium (or another buffer) to remove unattached cells.

The cells are cultured on the arrays to form a confluent monolayer for a time that is sufficient for the cells to fill the area defined by the array spot. One skilled in the art can monitor whether cells fill the area using microscopy to directly observe cells on the arrays. A sufficient amount of time can be, for example, from about 12 hours to about 36 hours. The density of cells in the cell suspension that is used to seed the SAM array can increase or decrease the time that is sufficient for the cells to fill the area (i.e., form a confluent monolayer) defined by the array spot. If a low density of cells is used to seed the entire SAM array, for example, it can take the cells a longer length of time to proliferate to a colony size that fills the area. In contrast, if a high density of cells is used to seed the entire SAM array, for example, it can take the cells a shorter length of time to proliferate to a colony size that fills the area. Additionally, the type of cell that is used to seed the array or the array spot can determine the time needed to fill the area defined by the array spot. If the cell type that is used has a fast proliferation rate, for example, it can take the cells a shorter length of time to proliferate to a colony size that fills the area. In contrast, if the cell type that is used has a slow proliferation rate, for example, it can take the cells a longer length of time to proliferate to a colony size that fills the area. One skilled in the art can, without undue experimentation, determine the time that is sufficient for a specific cell type to form a confluent monolayer that fills the area defined by the array spot by seeding arrays or array spots and monitoring cell growth by microscopy, for example. One skilled in the art can, without undue experimentation, determine the time that is sufficient for a specific density of cells to be seeded to an array or array spot to form a confluent monolayer of cells that fills the area defined by the array spot by seeding arrays or array spots with different solutions containing different densities of cells and monitoring cell growth by microscopy, for example.

The method further includes detaching the confluent monolayer. The confluent monolayer can be detached from the SAM by mechanical perturbations. Suitable mechanical perturbations may be by gentle fluid shearing by pipetting culture medium over the colonies to dislodge the colonies. Another suitable method for detaching the confluent monolayer can be, for example, by gently tapping or bumping the substrate. Additionally, the confluent monolayer may be detached by monitoring the confluent monolayer for a sufficient time and collecting colonies that spontaneously detach from the substrate.

Upon detachment, colonies may further be collected. Colonies may be collected by aspirating the colonies from the medium. Additionally or alternatively, the media may be obtained and colonies collected by allowing colonies to settle by gravity or be collected by centrifugation.

In another aspect, the present disclosure is directed to a method of preparing cell aggregates of a uniform size. The method comprises culturing a cell on a self-assembled monolayer ("SAM") array spot of a specific diameter for a sufficient time to form a confluent monolayer of cells; detaching the confluent monolayer of cells; and collecting the confluent monolayer of cells. The method can further comprise placing the collected confluent monolayer of cells in non-adherent suspension culture.

The SAM array may be prepared as described herein or using other methods known by those skilled in the art to prepare a SAM array having array spots in which the method allows for controlling array spot size. Array spot size can be any desired size. Particularly suitable array spot size can be, for example, at least 400 μm, including from about 600 μm to about 6 mm.

In another aspect, the present disclosure is directed to a method of preparing cell aggregates of a specified shape. The method comprises culturing a cell on a self-assembled monolayer ("SAM") array spot of a specified shape for a sufficient time to form a confluent monolayer of cells; detaching the confluent monolayer of cells; and collecting the confluent monolayer of cells. The method can further comprise placing the collected confluent monolayer of cells in non-adherent suspension culture. The method can further comprise analyzing the confluent monolayer of cells.

The SAM array may be prepared as described herein or using other methods known by those skilled in the art to prepare a SAM array having array spots in which the method allows for controlling array spot shape. Array spot shape can be any desired shape as known in the art. Particularly suitable array spot shapes can be, for example, circular, oval, oval cross, star, and hand shaped spots. Spot shape can be used to control time to invagination. For example, a circular spot shape can increase the time it takes for cell monolayers to begin invaginating. Spots in the shape of oval or oval cross-shape, for example, can decrease the time it takes for cell monolayers to begin invaginating.

Cells can be seeded on SAM arrays or array spots as described herein. The cells are cultured on the arrays to form a confluent monolayer for a time that is sufficient for the cells to fill the area defined by the array spot. The shape of the confluent monolayer will correspond to the shape of the array spot. Once the confluent monolayer attains a shape defined by the array spot shape, the method further includes detaching the confluent monolayer as described herein. The confluent monolayer can then be collected as described herein. The collected confluent monolayer can then be placed in a non-adherent suspension culture.

Confluent monolayers and/or cells can be further processed by further culturing cells in a non-adherent suspension culture. Cells can also be further be analyzed by microscopy, for gene expression, protein expression, and combinations thereof.

Suitable cells for use in the methods of the present disclosure may be any cell known by those skilled in the art. Particularly suitable cells may be, for example, pluripotent stem cells, mesenchymal stem cells (MSCs), umbilical vein endothelial cells (UVECs), NIH 3T3 fibroblasts, dermal fibroblasts (DFs), fibrosarcoma cells (HT-1080s), and embryonic stem cells (ESCs). Particularly suitable cells may be, for example, human induced pluripotent stem cells, human mesenchymal stem cells (MSCs), human umbilical vein endothelial cells (UVECs), human dermal fibroblasts (DFs), HT-1080s fibrosarcoma cells (HT-1080s), human embryonic stem cells (ESCs), iPS IMR90-4 cells, and an iPS-derived endothelial cell.

The methods of the present disclosure provide alternative techniques for generating stem cell colonies having controlled size and/or shape. Advantageously, the aggregates formed using these methods are heterogeneous in size and shape, which can lead to more efficient and controlled differentiation of the cells. Because aggregates formed using these methods have a uniform size and shape, better control over which differentiation pathway the cells proceed can also be achieved.

The disclosure will be more fully understood upon consideration of the following non-limiting Examples.

Example 1

In this Example, a SAM array having an adhesion ligand was prepared.

Carboxylic acid-capped hexa(ethylene glycol) undecanethiole (HS—$C_{11}$—(O—$CH_2$—$CH_2$)$_6$—O—$CH_2$—COOH) (referred to herein as "HS—$C_{11}$-$EG_6$-COOH"), was purchased from Prochimia (Sopot, Poland). 11-tr(ethylene glycol)-undecane-1-thiol (HS—$C_{11}$—(O—$CH_2$—$CH_2$)$_3$—OH (referred to herein as "HS—$C_{11}$-$EG_3$-OH") was synthesized as described in (Prime and Whitesides, J. Am. Chem. Soc. 115(23)):10714-10721 (1993)). Fmoc-protected amino acids and Rink amid MBHA peptide synthesis resin were purchased from NovaBiochem (San Diego, Calif.). Hydroxybenzotriazol (HOBt) was purchased from Advanced Chemtech (Louisville, Ky.). Diisopropylcarbodiimide (DIC) was purchased from Anaspec (San Jose, Calif.). N-hydroxysuccinimide (NHS), n-(3-dimethylaminopropyl)-N'-ethylcarbodiimide hydrochloride (EDC), sodium dodecyl sulfate (SDS), trifluoroacetic acid (TFA), diethyl ether, and deionized ultrafiltered water (DIUF $H_2O$) were purchased from Fisher Scientific (Fairlawn, N.J.). Triisopropylsilane (TIPS), piperidine, dimethylformamide (DMF), acetone, hexanes, and acetonitrile were purchased from Sigma-Aldrich (St. Louis, Mo.). Absolute ethanol (EtOH) was purchased from AAPER Alcohol and Chemical Co. (Shelbyville, Ky.). All purchased items were of analytical grade and used as received. Thin films of 100 Å Au <111>, 20 Å Ti on 1"×3"×0.040" glass were purchased from Platypus Technologies, LLC (Madison, Wis.).

Standard solid phase Fmoc-peptide synthesis (Fmoc SPPS) was performed to synthesize peptides using a 316c automated peptide synthesizer (C S Bio, Menlo Park, Calif.). Rink amide MBHA resin was used as the solid phase, and HOBt and DIC were used for amino acid activation and coupling. After coupling the final amino acid, a 4-hour incubation in TFA, TIPS, and DIUF (95:2.5:2.5) released the peptide from resin and removed protecting groups. Released peptide was extracted from the TFA/TIPS/DIUF cocktail via precipitation in cold diethyl ether. Lyophilized peptides were analyzed using matrix-assisted laser desorption/ionization-time-of-flight (MALDI-TOF) mass spectrometry with a Bruker Reflex II (Billerica, Mass.). The purity of synthesized peptides was verified to be greater than 90% via HPLC using a C18 analytical column (Shimadzu, Kyoto, Japan) with a gradient of 0-70% $H_2O$+0.1% TFA/acetonitrile and a flow rate of 0.9 mL/minute. GWGGRGDSP (SEQ ID NO: 1), GWGGRGESP (SEQ ID NO: 2) adhesion and mutant peptides were synthesized with tryptophan-bearing spacers to aid in determination of peptide concentration via UV/Vis. Peptide stocks were prepared at 300 μM in PBS as pH 7.4 as determined by absorbance at 280 nm using extinction coefficients outlined by Gill and von Hippel (Analytical Biochemistry 182(2):319-326 (1989)). Fluorescently-labeled GGRGDSPK (SEQ ID NO: 3) was synthesized as previously described (Koepsel and Murphy, Langmuir 25(21):12825-34 (2009)) and peptide concentration was determined by absorbance of the 5(6)-carboxyfluorescein group at 492 nm using an extinction coefficient of 81,000 $cm^{-1}M^{-1}$.

Polymer stencils containing arrays of wells were created using soft lithography. Master molds containing arrays of 1.2 mm to 2.4 mm diameter posts were fabricated from SU-8 (Microchem, Newton, Mass.) spin-coated silicon wafers using conventional photolithography techniques. Polydimethylsiloxane (PDMS) (Sylgard 184, Dow Corning, Midland, Mich.) was prepared by mixing a 10:1 ratio of base:curing agent (w/w) followed by degassing for ~30 minutes. The degassed mixture was cast over the mold and cured for 4 hours at 85° C. Following curing, PDMS stencils were removed from molds and cleaned in hexanes using overnight Soxhlet extraction. After cleaning, stencils were placed in vacuo to remove residual solvent from the Soxhlet extraction process.

Gold slides were placed into a 150 mm glass Petri dish, covered with EtOH and sonicated for ~1 minute using an ultrasonic bath (Bransonic 1510, Branson, Danbury, Conn.). Sonicated gold chips were then rinsed with EtOH and blown dry with $N_2$. As illustrated in FIG. 1, SAM arrays were fabricated as follows: elastomeric (polymer) stencils containing arrays of 1.2 mm to 2.4 mm diameter holes were placed on a bare gold surface to form an array of wells on the gold substrate. For spot shape, elastomeric stencils with arrays in the shape of circles, ovals, and oval cross were placed on a bare gold surface to form an array of wells having these shapes on the gold substrate. Wells were then filled with 1 mM ethanolic alkanethiolate solution and incubated for 10 minutes in a chamber containing a laboratory wipe soaked in ethanol to prevent evaporation during local SAM formation. Alkanethiolate solutions were then aspirated and wells were rinsed with DIUF $H_2O$. Carboxylate groups were then converted to active ester groups by adding a solution of 100 mM NHS and 250 mM EDC in DIUF $H_2O$ pH 5.5 to wells and incubated for 10 minutes. After an additional rinse with DIUF $H_2O$, 300 μM solutions of GWGGRGDSP (SEQ ID NO: 1), GWGGRGESP (SEQ ID NO: 2; glycosaminoglycan peptide), cyclo(RGDF$_D$C) (SEQ ID NO: 4; wherein "$F_D$" denotes D-phenylalanine; commercially available from Peptides International, Louisville, Ky.), CGKKQRFRHRNRKG (SEQ ID NO: 5; commercially available from GenScript, Piscataway, N.J.) or KRTGQYKL (SEQ ID NO: 6; commercially available from GenScript, Piscataway, N.J.) in PBS and pH 7.4 were added to each well and incubated for 1 hour in a humidity controlled chamber to covalently couple peptides to each array spot. After a final rinse in DIUF $H_2O$, regions surrounding array spots were backfilled with HS—$C_{11}$-$EG_3$-OH. This was accomplished by submerging the gold substrate and attached elastomeric stencil in an aqueous 0.1 mM HS—$C_{11}$-$EG_3$-OH solution (pH 2.0), removing the stencil, and incubating for 10 minutes. Following backfilling, the array was rinsed with 0.1 wt % SDS in DIUF $H_2O$, DIUF $H_2O$, and EtOH and then dried under a stream of $N_2$. Arrays were stored in sterile DIUF $H_2O$ at 4° C. and used within 24 hours.

Pluripotent stem cells were seeded on arrays at a density of $10^5$ cells/$cm^2$. Cells were cultured in E8 medium with ROCK inhibition (using Y-27632) for 12 hours to 36 hours until reaching confluence. Colonies that spontaneously detached from SAM spots were also harvested. Colonies were analyzed for Oct 3/4 and Nanog expression by immunofluorescence using DAPI to stain nuclei.

Figure 2A:
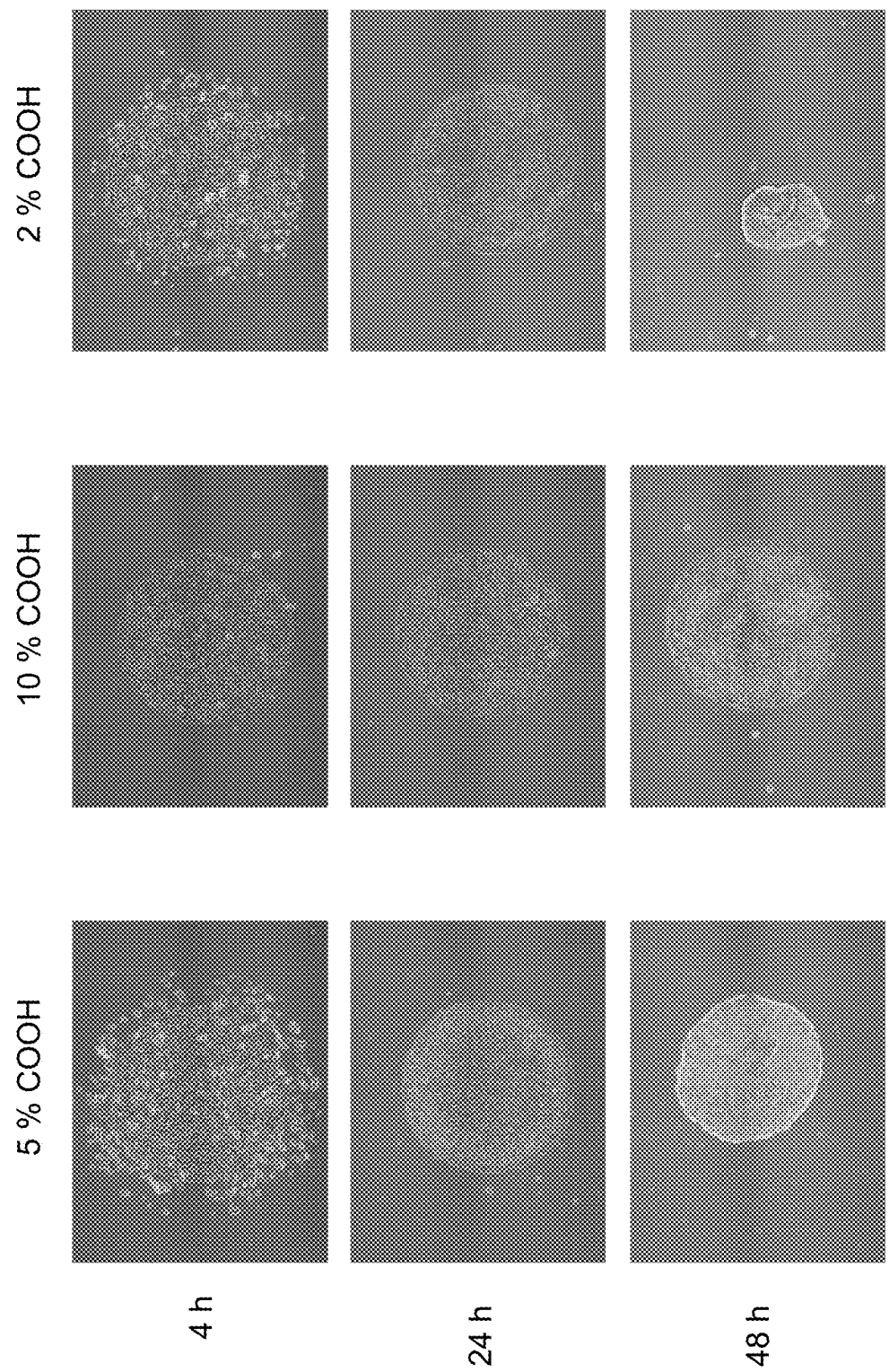
FIG. 2A depicts hESC (H1) monolayer formation as a function of density of adhesion ligands (cyclic RGD) as described in Example 1.

The concentration of the integrin adhesion peptides GWGGRGDSP (SEQ ID NO: 1) and cyclic RGD (SEQ ID NO: 4) on the array spot was varied between 2% and 10% by the fraction of COOH groups functionalized with peptides present at the spot among background OH functionalities. As shown in FIG. 2A, the density of the adhesion ligand (cyclic RGD; SEQ ID NO: 4) affected hESC monolayer adhesion over a time from 4 hours to 48 hours in culture. At 48 hours in culture, the hESC monolayer formed in the 2% COOH density array spot was loosely associated with the array spot, whereas the hESC monolayers formed in the 5% and 10% density array spots were more strongly adhered to the array spot. These results demonstrated that a COOH fraction of 2% led to a significantly lower cell adhesion as compared to 5% COOH, whereas 10% COOH did not lead to an improved attachment for surfaces functionalized with cyclic RGD. In addition, a lower peptide density leads to an earlier start of the invagination process (see, FIG. 2A, 2% COOH condition).

Figure 2B:
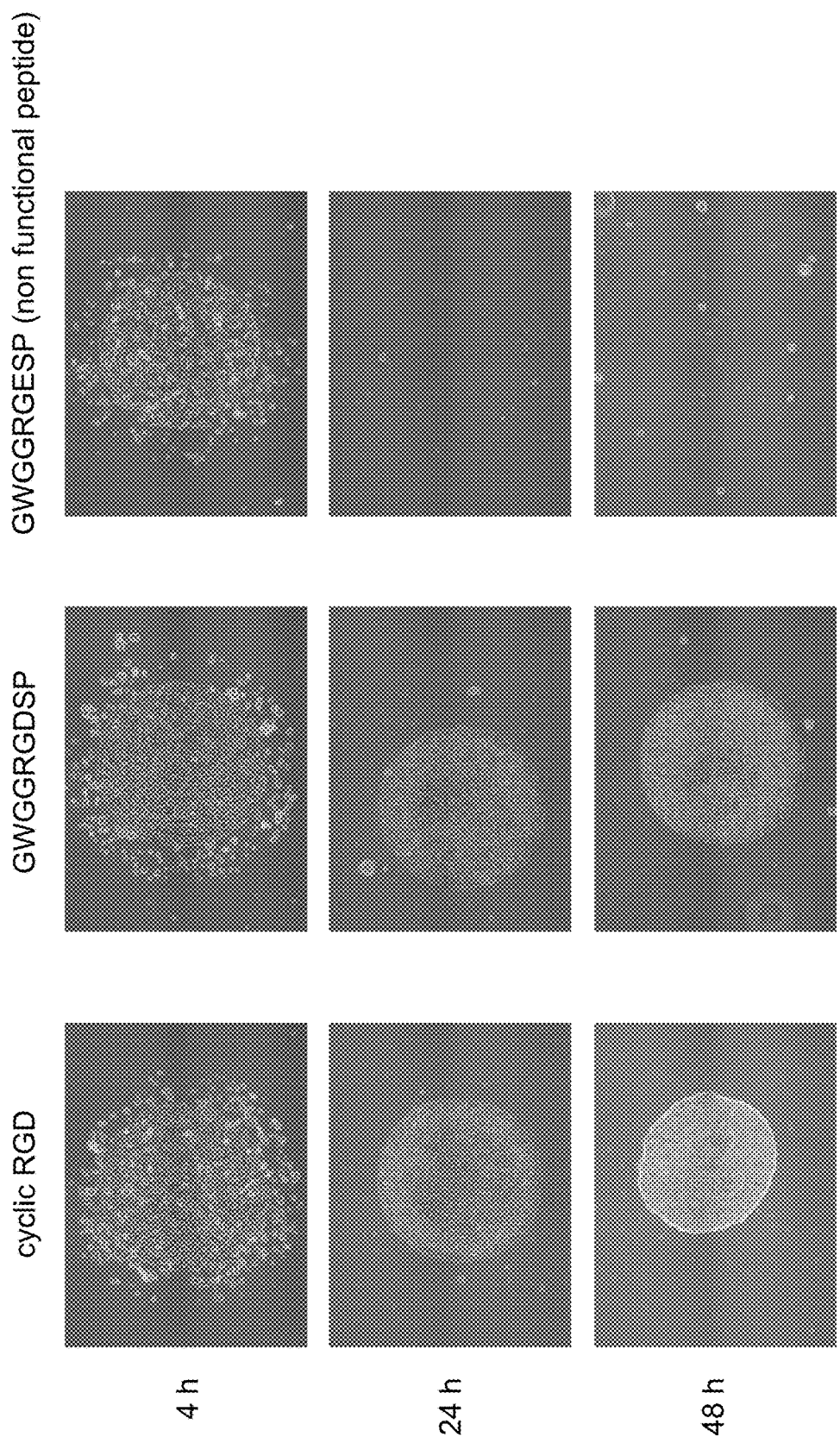
FIG. 2B depicts hESC (H1) monolayer formation as a function of adhesion ligands as described in Example 1.
Figure 2C:
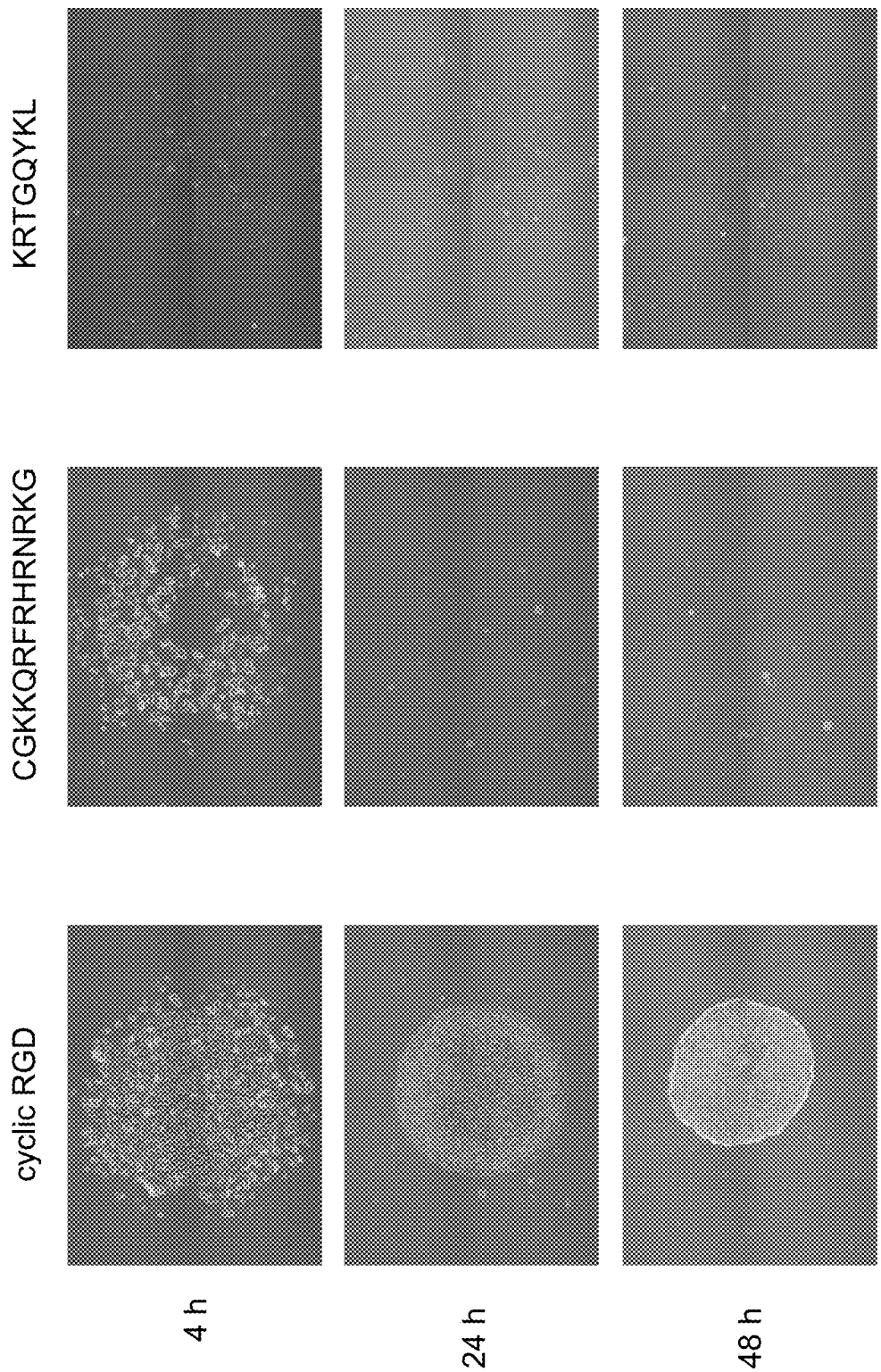
FIG. 2C depicts hESC (H1) monolayer formation as a function of adhesion ligands as described in Example 1.

The particular adhesion ligands used in the array spot also influenced cell monolayer adhesion in the array spot. As shown in FIG. 2B, the best cell adhesion of the hESC monolayer was observed with cyclic RGD (SEQ ID NO: 4) and GWGGRGDSP (SEQ ID NO: 1). No significant differences were observed using the scrambled reference GWG-GRGESP (SEQ ID NO: 2). As shown in FIG. 2C, no significant adhesion was observed with the heparin binding peptide KRTGQYKL (SEQ ID NO: 6). After initial attachment of the cells to the glycosaminoglycan binding peptide CGKKQRFRHRNRKG (SEQ ID NO: 5) array spots, the cells detached within 12 h (FIG. 2C). Additionally, significantly less cell attachment was observed on the glycosaminoglycan binding peptide CGKKQRFRHRNRKG (SEQ ID NO: 5) array spots.

Figure 3A:
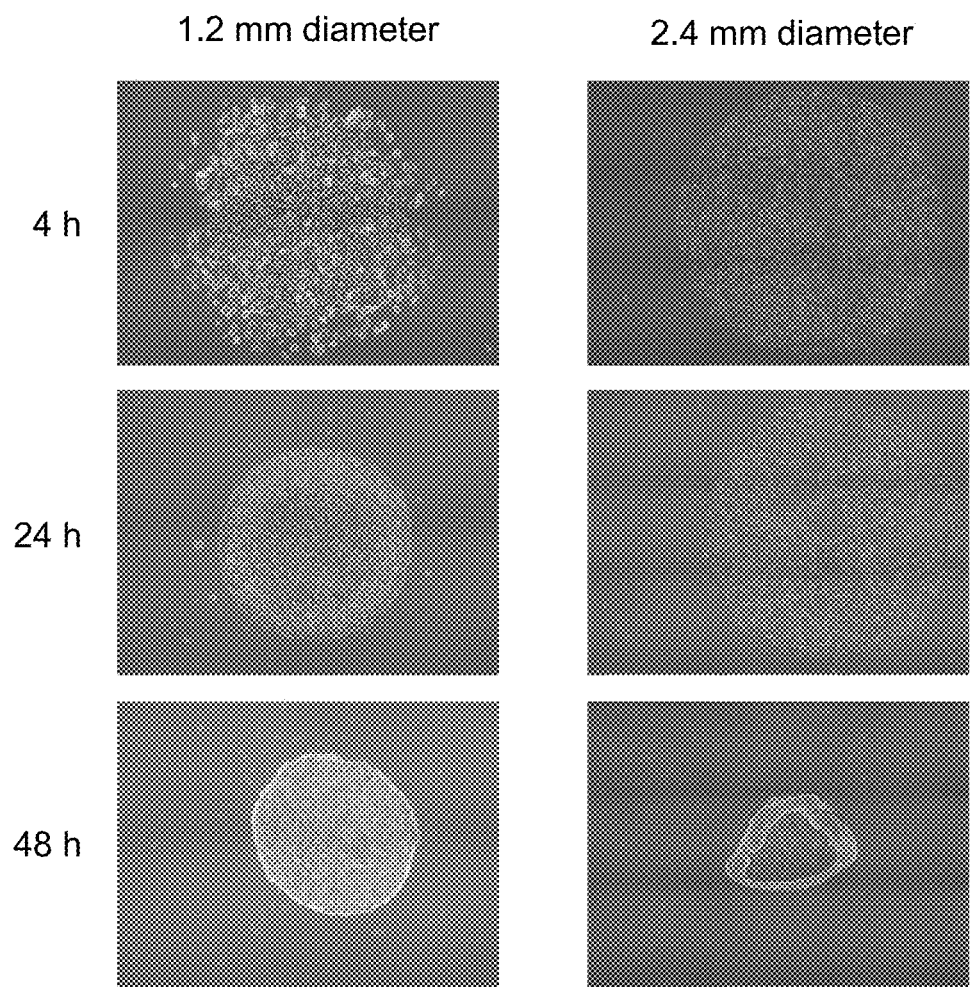
FIG. 3A depicts hESC (H1) monolayer formation as a function of spot size as described in Example 1.
Figure 3B:
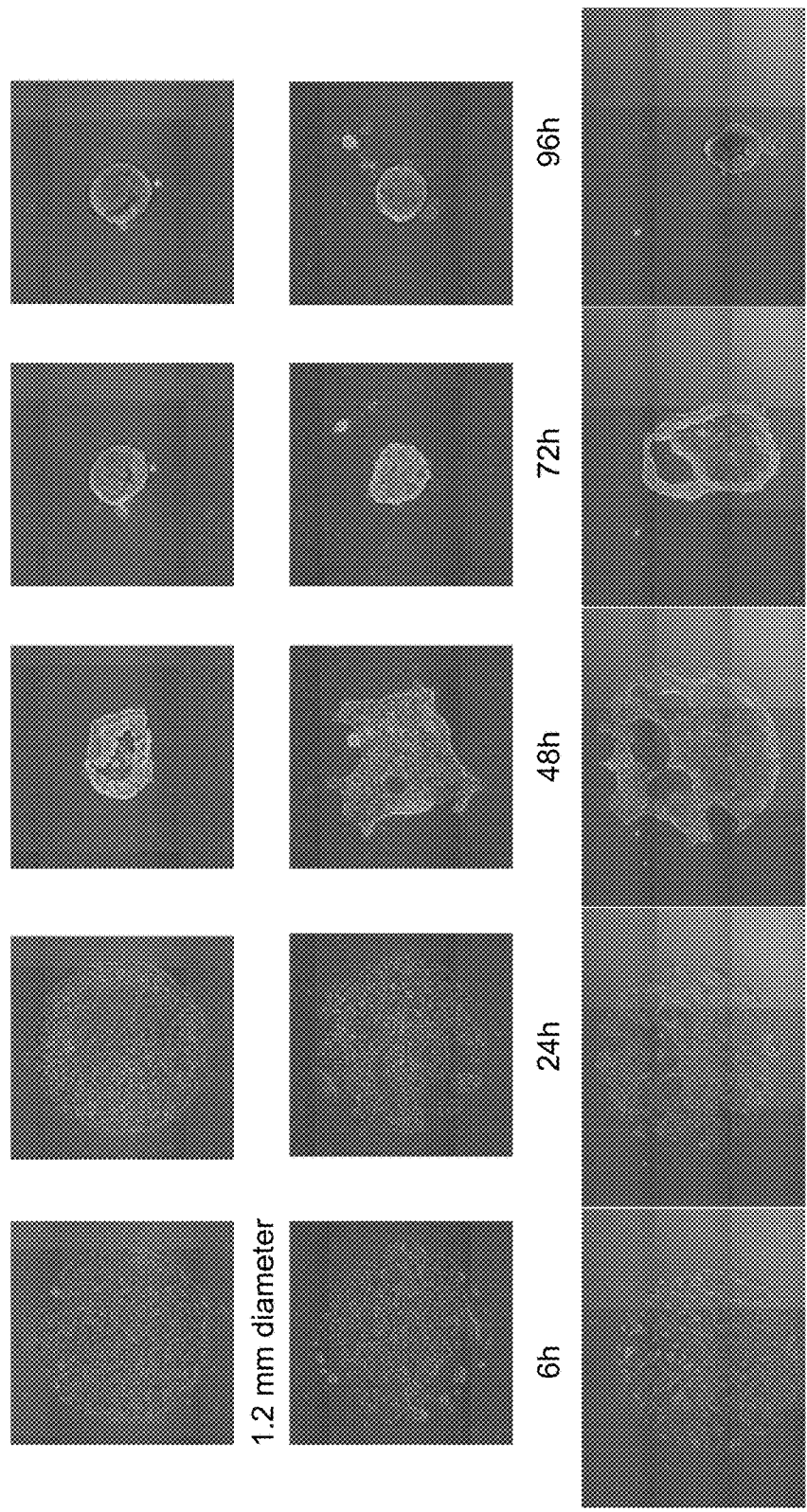
FIG. 3B depicts hESC (H1) monolayer formation as a function of spot size as described in Example 1. More particularly.

The size of the array spots was found to influence monolayer morphology over time. As shown in FIG. 3A, the edges of the hESC monolayers formed on 1.2 mm and 2.4 mm diameter array spots began to fold over after 48 hours in culture. As shown in FIG. 3B, the morphology of hESC monolayers cultured on circle-shaped array spots was followed from a time period of 6 hours to 96 hours. At 72 hours, hESC monolayers cultured on 1.2 mm diameter array spots were in the form of balls similar to embryoid bodies that became tight balls of cells by 96 hours. At 72 hours, the edges of cells from the hESC monolayers cultured on 2.4 mm diameter array spots were still in the process of folding over, but formed tight balls of cells by 96 hours.

Figure 3C:
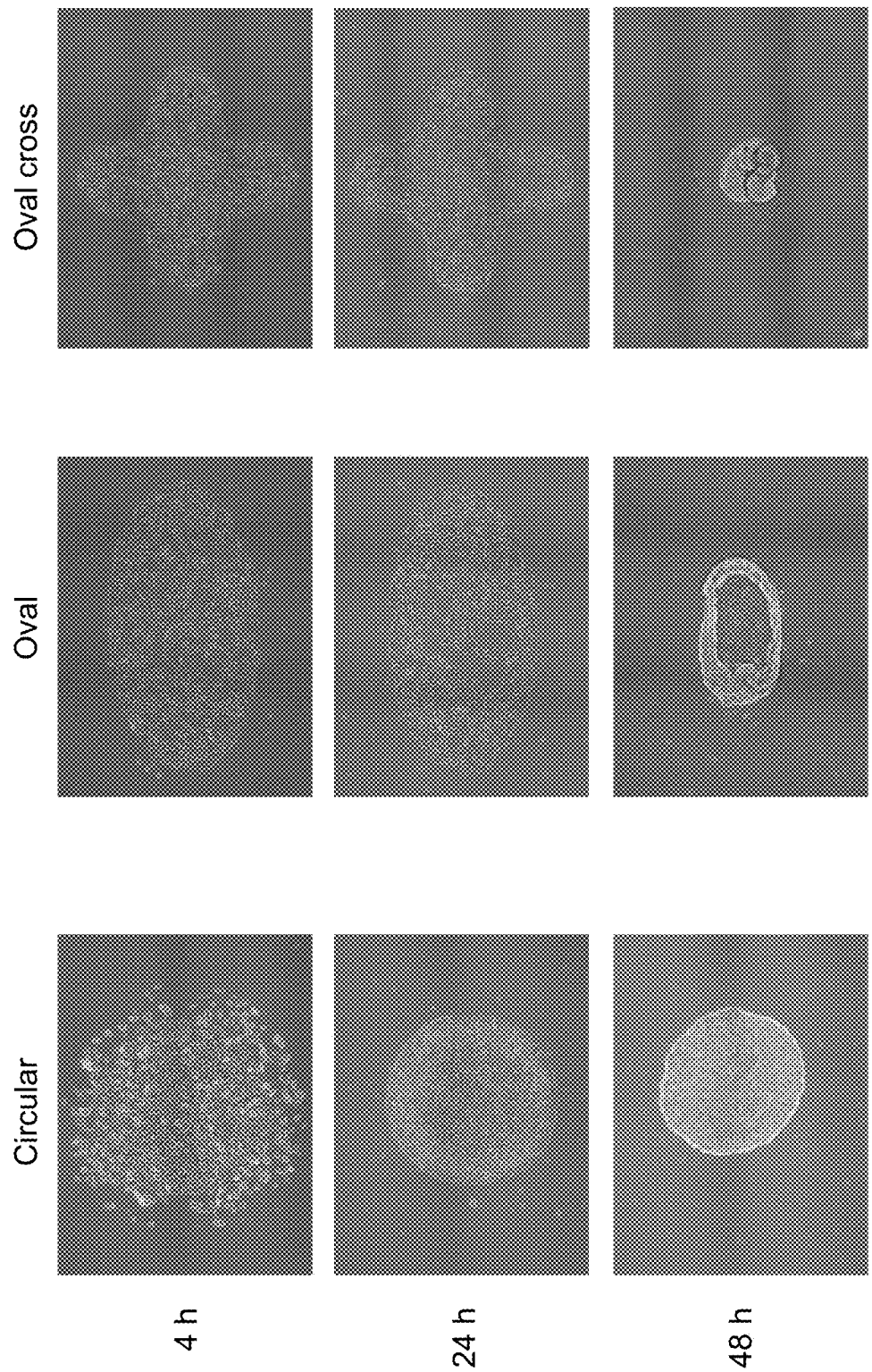
FIG. 3C depicts hESC (H1) monolayer formation as a function of spot shape as described in Example 1.
Figure 3D:
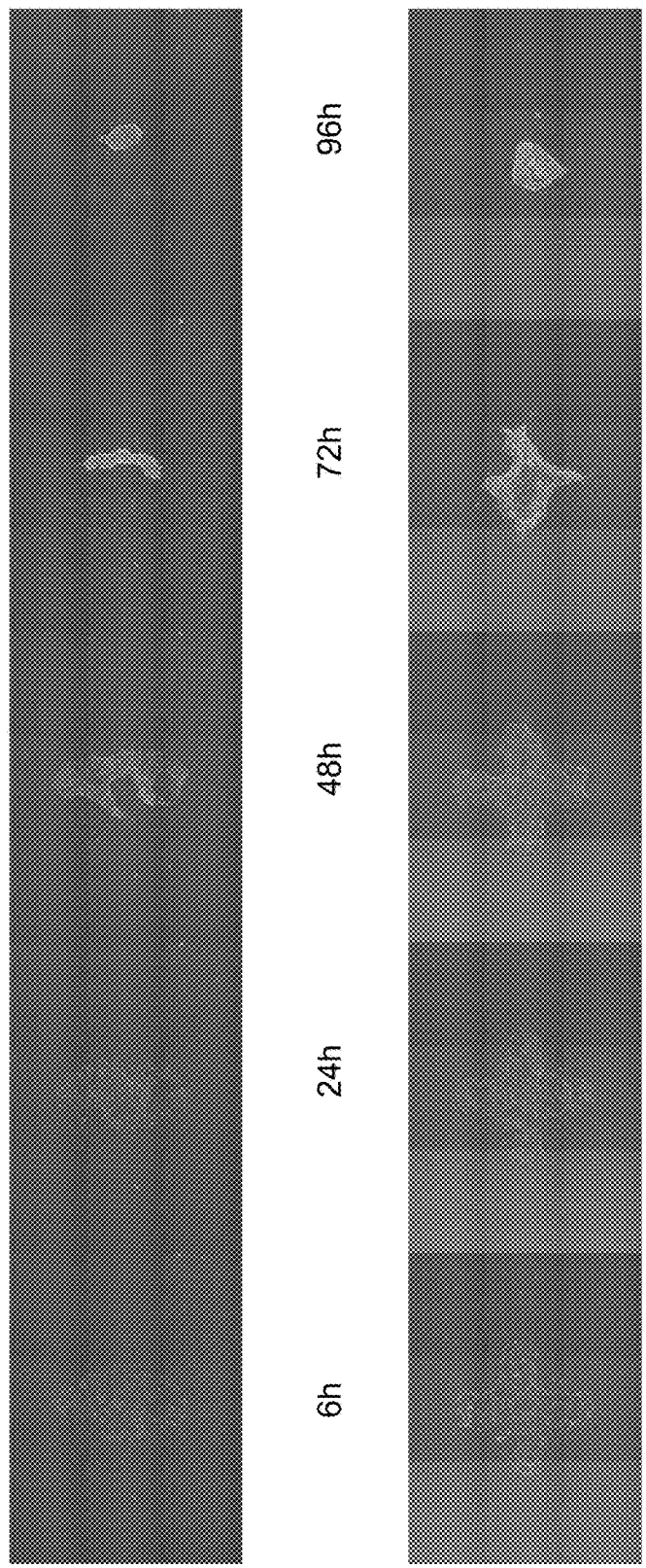
FIG. 3D depicts hESC (H1) embryoid body formation as a function of spot shape as described in Example 1. More particularly.

As shown in FIG. 3C, the morphology of hESC monolayers cultured on circle-, oval-, and oval cross-shaped array spots was followed from a time period of 4 hours to 48 hours. At 4 hours and 24 hours in culture, the cell monolayers assumed the shape of the array spot. At 48 hours, the edges of the hESC monolayers formed on the circular shaped array spot had just begun to fold over, whereas hESC monolayers formed on the oval-shaped array spot were folded. hESC monolayers formed on oval cross-shaped array spots were formed into a ball-like shape by 48 hours that was reminiscent of an embryoid body. As further shown in FIG. 3D, hESC monolayers formed on the oval-shaped array spot appeared to fold over longitudinally to form an elongated morphology (see 72 hour photomicrograph) before becoming more ball-like at the 96 hour time point. hESC monolayers formed on the oval cross-shaped array spot also appeared to fold along a longitudinal axis at each arm of the cross before becoming ball-shaped at the 96 hour time point.

Figure 3E:
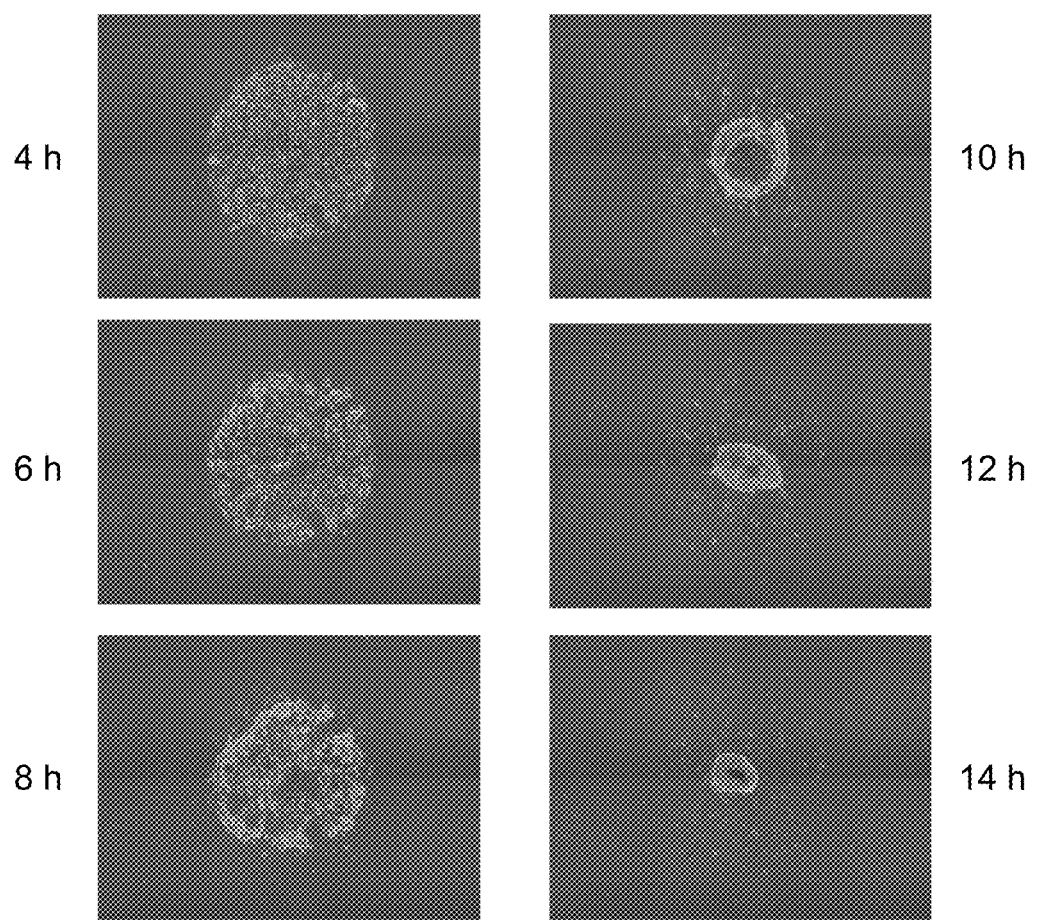
FIG. 3E depicts rapid embryoid body formation from 4-14 hours after hESC (H1) seeding on a spot with 5% ligand density, functionalized with a 1:1 mixed layer of cyclic RGD and CGKKQRFRHRNRKG as described in Example 1.

As shown in FIG. 3E, a mixed layer of the cyclic RGD (SEQ ID NO: 4) and the CGKKQRFRHRNRKG (SEQ ID NO: 5) could be used to influence the time it took for cell monolayers to form the ball-shaped (embryoid body-like) morphology. Specifically, a 1:1 functionalization with cyclic RGD (SEQ ID NO: 4) and CGKKQRFRHRNRKG (SEQ ID NO: 5) at a ligand density of 5% lead to invagination within 16 h after seeding.

Figure 4:
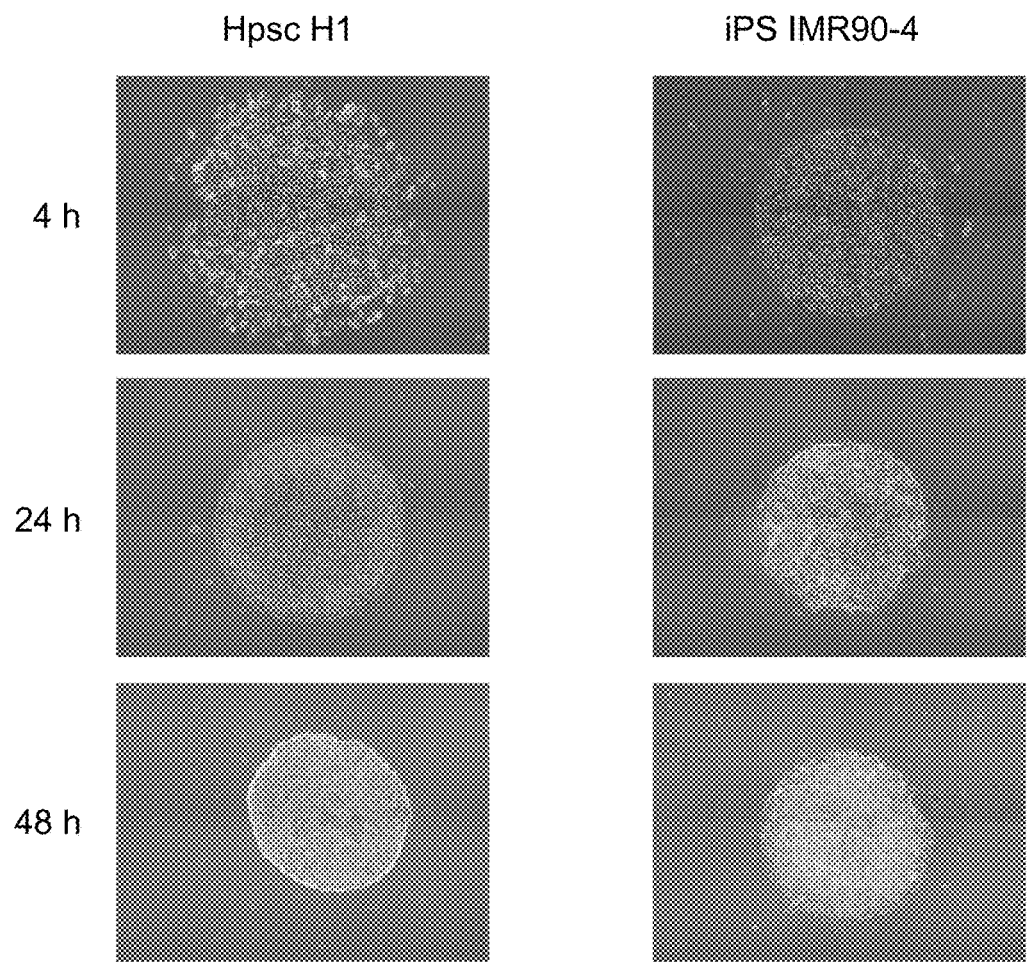
FIG. 4 depicts hESC (H1) monolayer formation as a function of cell lineages as described in Example 1.
Figure 5A:
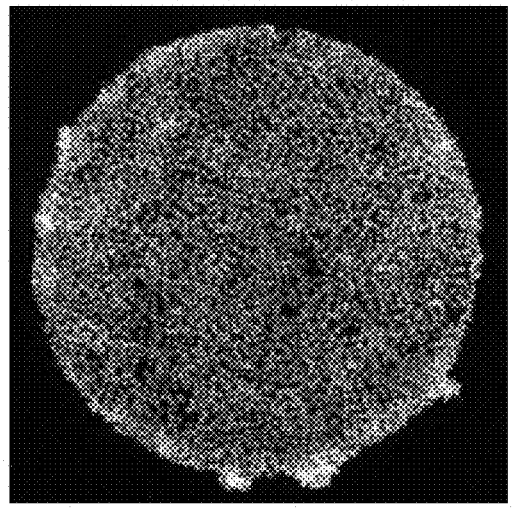
FIGS. 5A-D depict pluripotency staining of hESC (H1) grown on SAM array for Oct3/4 and Nanog as described in Example 1.
Figure 5B:
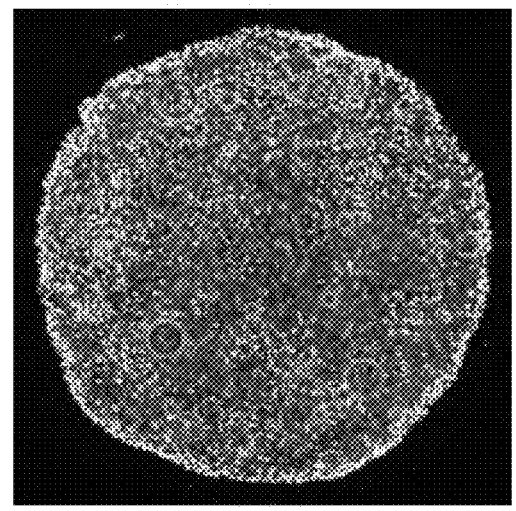
Figure 5C:
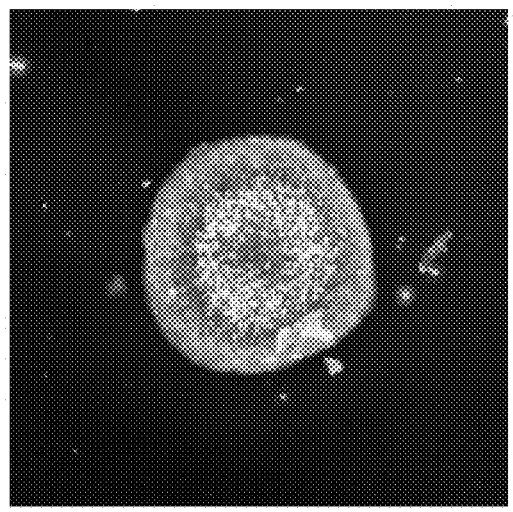
Figure 5D:
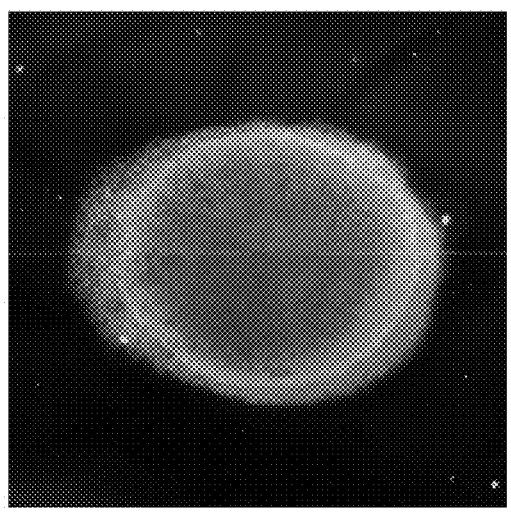
Figure 6A:
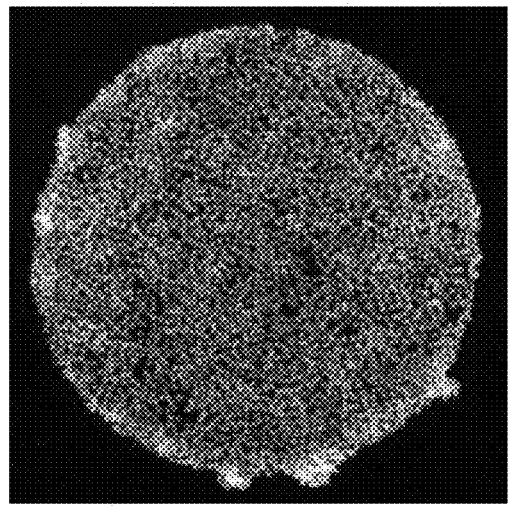
FIGS. 6A-D depict staining of hESC (H1) grown on SAM array for Oct3/4 and Nanog at Day 0 as described in Example 1.
Figure 6B:
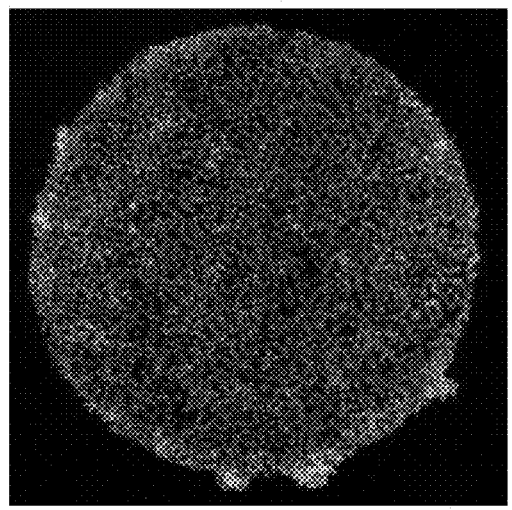
Figure 6C:
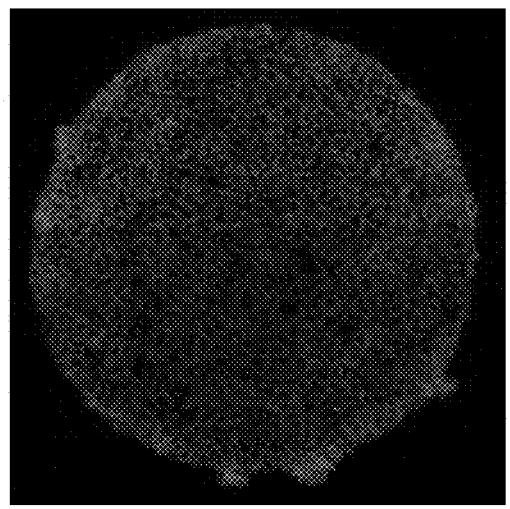
Figure 6D:
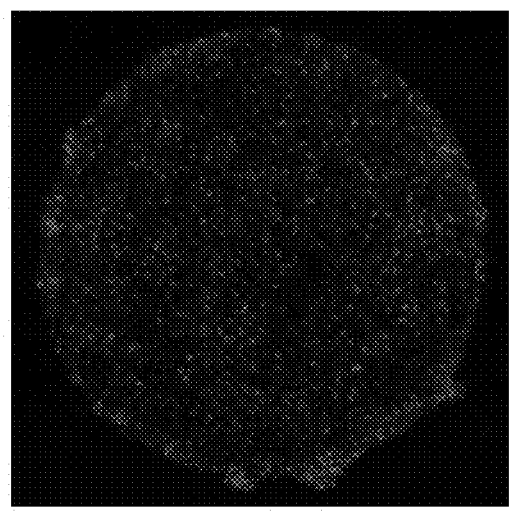
Figure 7A:
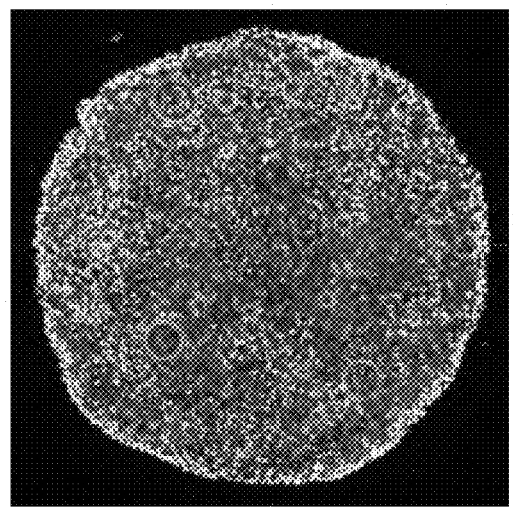
FIGS. 7A-D depict staining of hESC (H1) grown on SAM array for Oct3/4 and Nanog at Day 1 as described in Example 1.
Figure 7B:
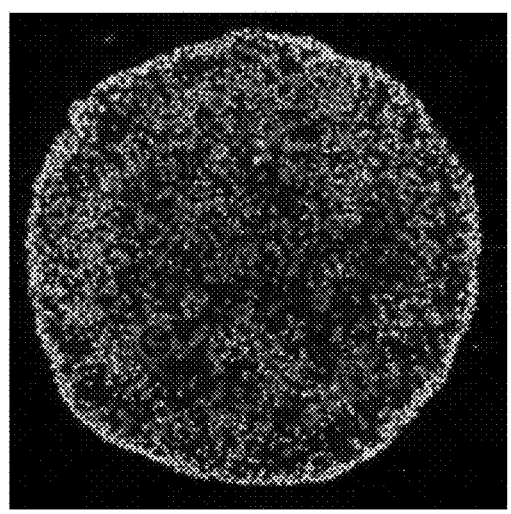
Figure 7C:
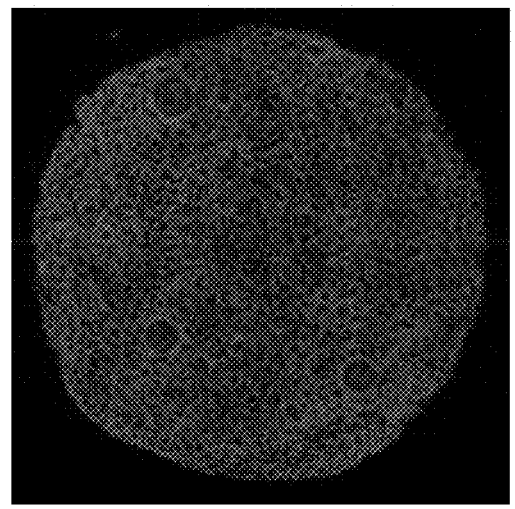
Figure 7D:
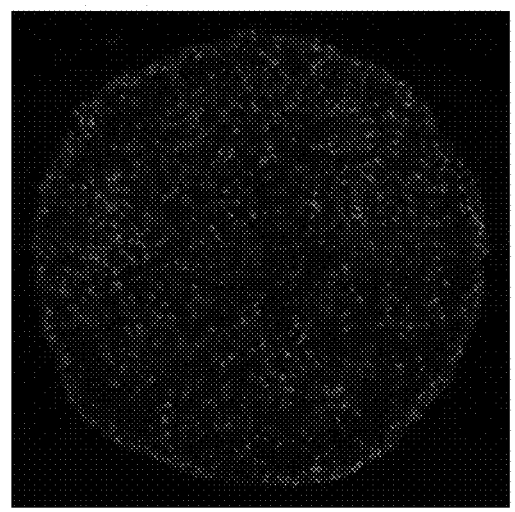
Figure 8A:
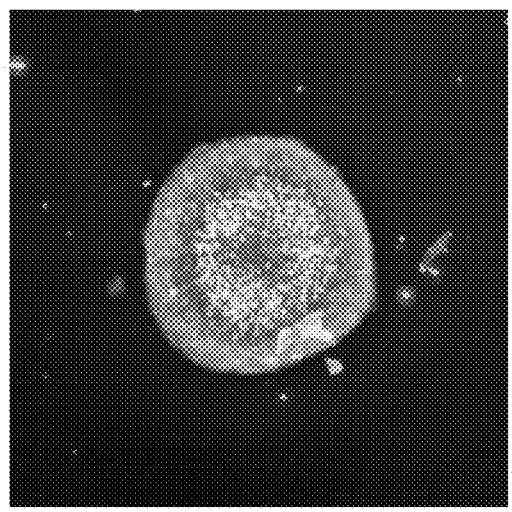
FIGS. 8A-D depict staining of hESC (H1) grown on SAM array for Oct3/4 and Nanog at Day 2 as described in Example 1.
Figure 8B:
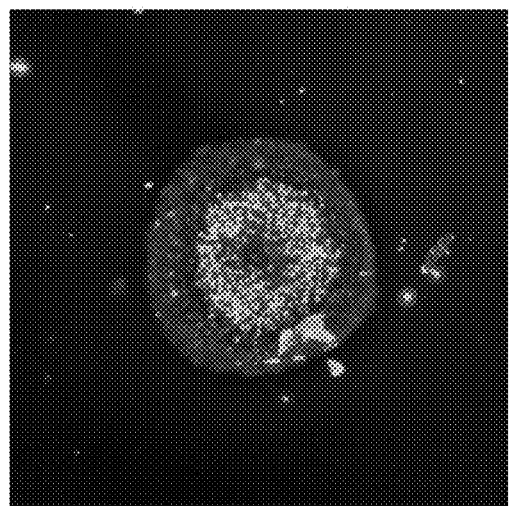
Figure 8C:
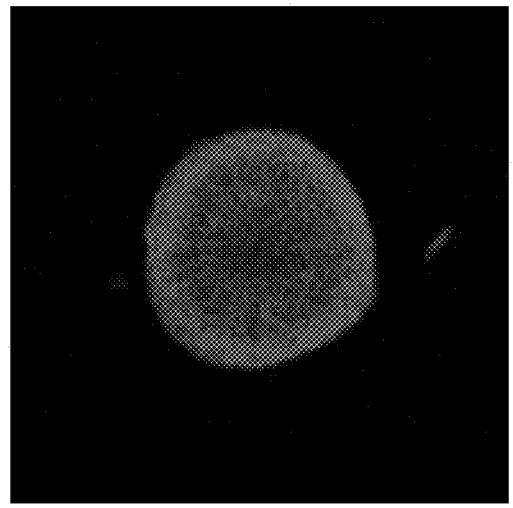
Figure 8D:
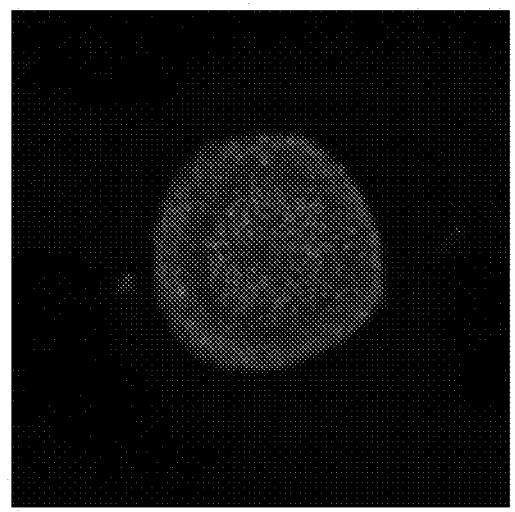
Figure 9A:
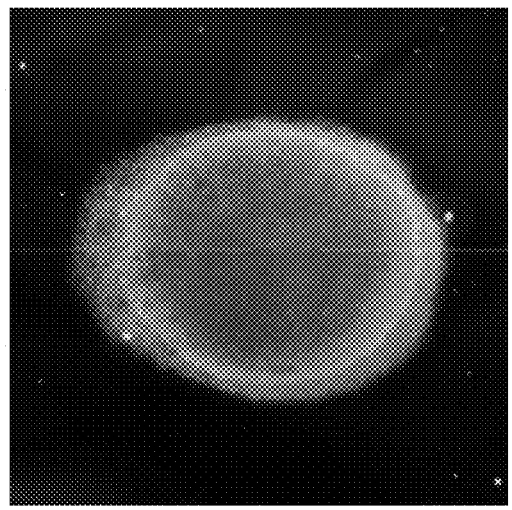
FIGS. 9A-D depict staining of hESC (H1) grown on SAM array for Oct3/4 and Nanog at Day 3 as described in Example 1.
Figure 9B:
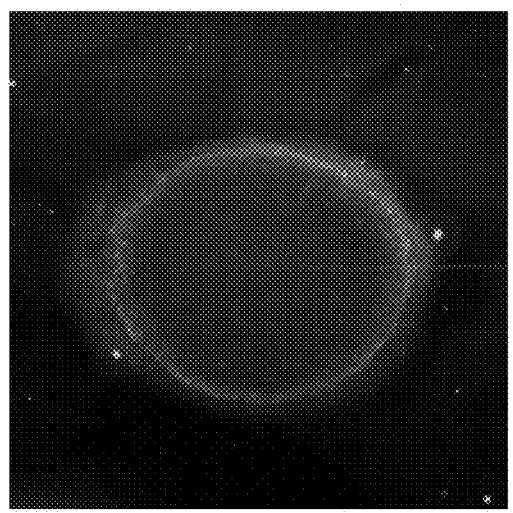
Figure 9C:
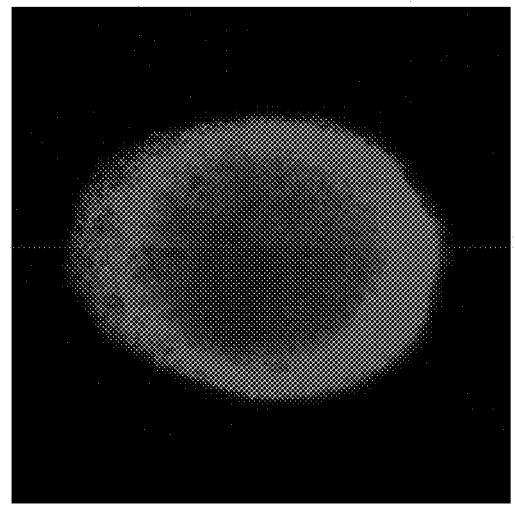
Figure 9D:
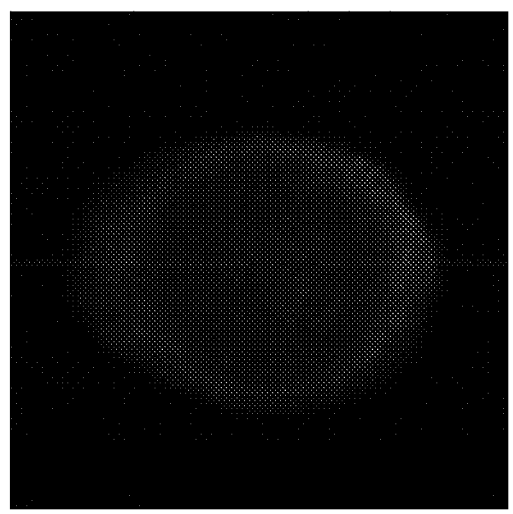

To show the universality of the cell culture approach, iPS IMR90-4 cells were grown on array spots. As demonstrated in FIG. 4, iPS IMR90-4 cells also formed monolayers on array spots.

Cells cultured on array spots were stained for pluripotency markers Oct 3/4 and Nanog. Cell nuclei were also stained with DAPI to identify cells. FIGS. 5A-D show overlay images of Oct 3/4, Nanog, and nuclear staining for Days 1-3 to demonstrate pluripotency of the cells at each day. As shown in FIGS. 6A-D, 5 hours after seeding (Day 0), cells stained positive for Oct 3/4 and Nanog. At 24 hours after seeding (Day 1), only cells near the edge of the monolayer stained positive for Oct 3/4 and Nanog (FIGS. 7A-D). At 48 hours after seeding (Day 2), right after the edges of the monolayer began to fold (invaginate), only a part of the cells stained positive for Oct 3/4 and Nanog (FIGS. 8A-D). At 72 hours after seeding (Day 3), no more cells stained positive for Oct 3/4 and Nanog (FIGS. 9A-D). These results demonstrate that as cells develop on the array spot, the morphological changes observed for the cell monolayers correlates with loss of pluripotency markers to form ball-like cells similar to embryoid bodies.

These results demonstrate that the SAM arrays of the present disclosure can be used to culture cells with controlled size and shape. Moreover, the methods of the present disclosure allow for the development of a monolayer of cells that proceeds through morphological stages to develop into 3-dimensional ball-shaped cells similar to embryoid bodies. Further, as the cells develop and go through morphological changes, pluripotency marker staining also indicates that the cells lose their pluripotency during culture.

Example 2

Figure 11:
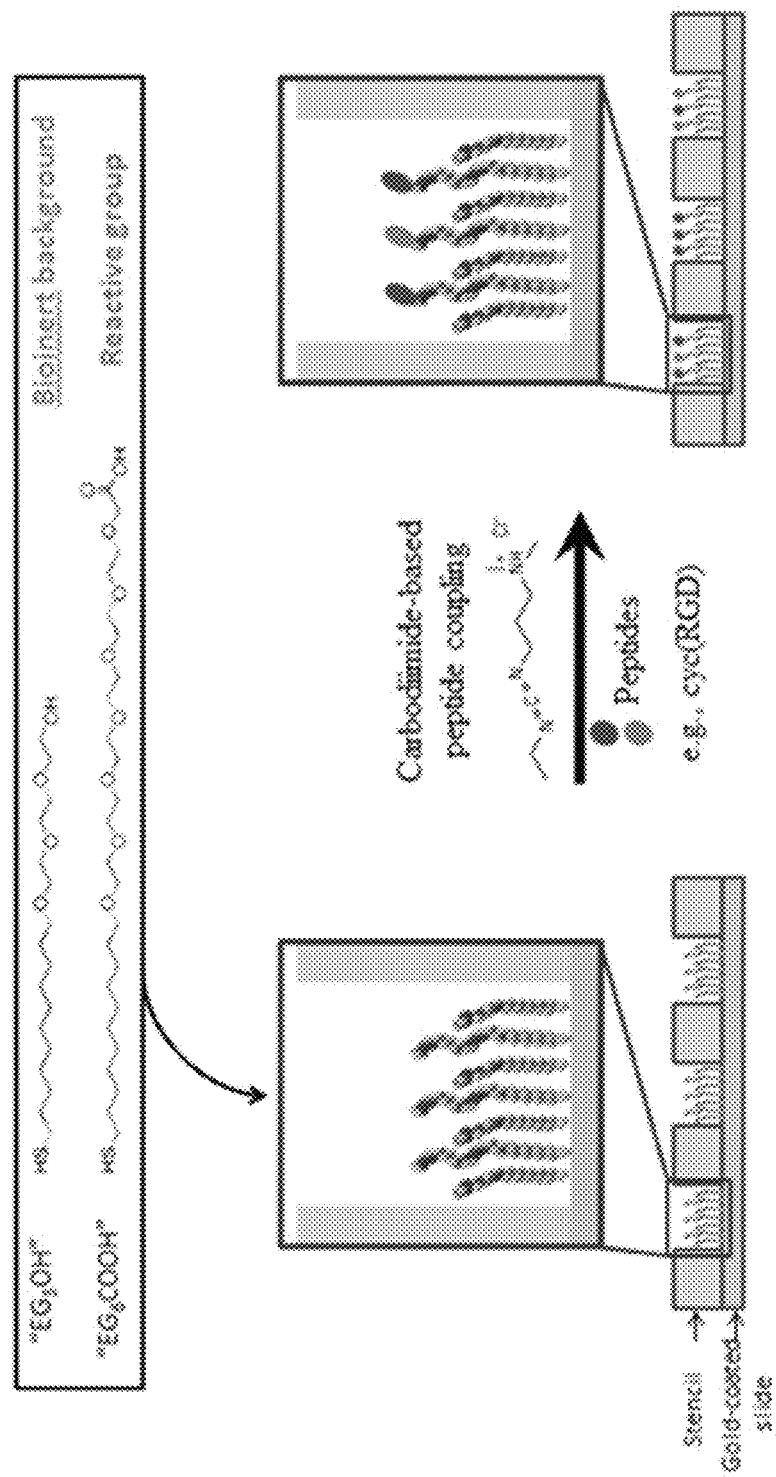
FIG. 11 is a schematic illustrating the steps for preparing a self-assembled monolayer array used in one embodiment of the methods of the present disclosure.
Figure 12:
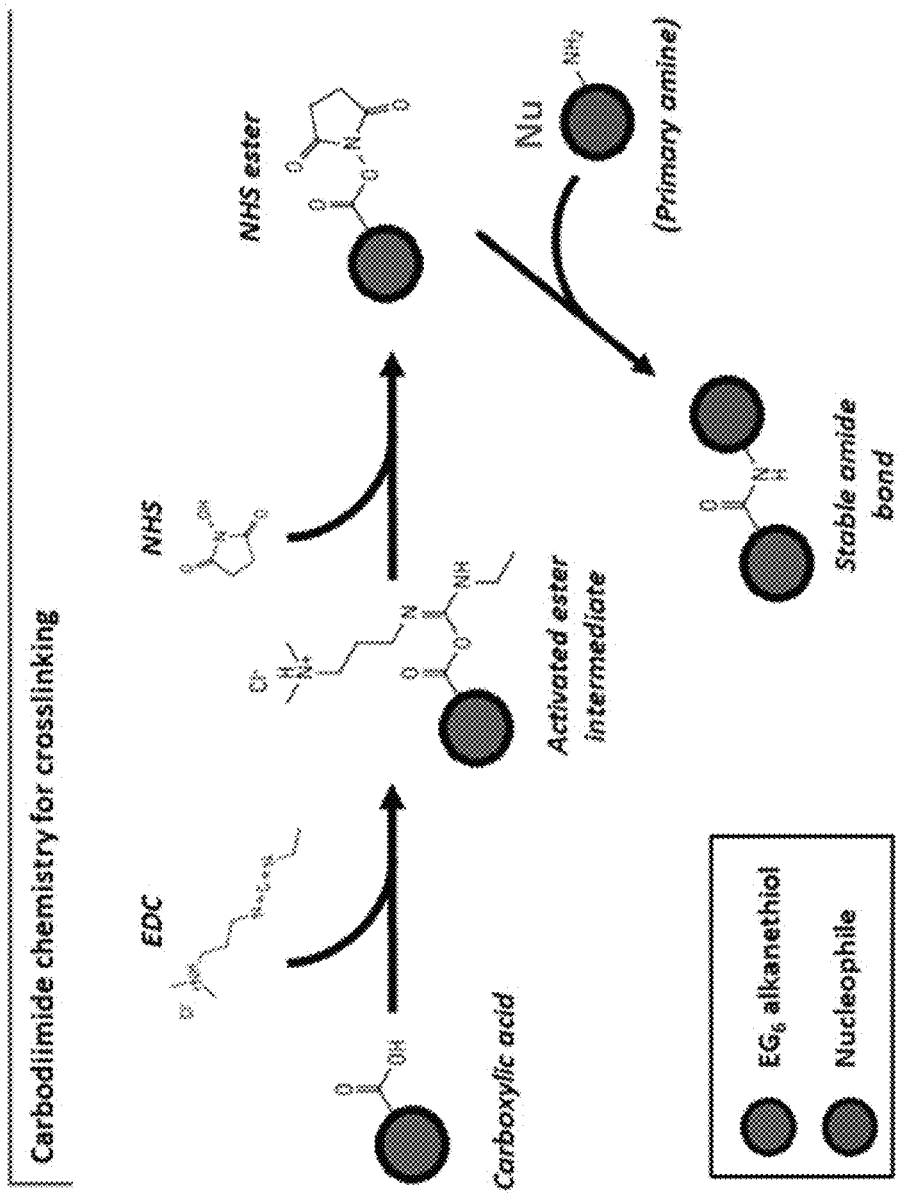
FIG. 12 is a schematic illustrating steps in EDC-based carbodiimide crosslinker chemistry typically used to cross-link between carboxylic acids and amine groups. The "primary amine" is enclosed in parentheses to indicate that non-amine nucleophiles could, in theory, also participate in this reaction to generate linkages other than amide bonds. The case where a thiolate acts as the nucleophile, for instance, would result in formation of a thioester bond (here, considered "labile" linkages).

In this Example, a SAM array having an adhesion ligand was prepared. Specifically, as shown in FIG. 11, carbodiimide chemistry was used to couple peptides to carboxylic acid-terminated alkanethiols on the surface of the SAM array. As shown in FIG. 12, an adhesion ligand containing nucleophilic group(s) was expected to couple to the SAM array spots through either a labile or non-labile chemical bond.

Carboxylic acid-terminated hexa(ethylene glycol) undecanethiol (HS—$C_{11}$—(O—$CH_2$—$CH_2$)$_6$—O—$CH_2$—COOH) (referred to herein as "HS—$C_{11}$-$EG_6$-COOH"), was purchased from Prochimia (Sopot, Poland). 11-tri(ethylene glycol)-undecane-1-thiol(HS—$C_{11}$—(O—$CH_2$—$CH_2$)$_3$—OH (referred to herein as "HS—$C_{11}$-$EG_3$-OH") was synthesized as described in (Prime and Whitesides, J. Am. Chem. Soc. 115(23)):10714-10721 (1993)). Cyclic pentapeptides cyclo(RGDF$_D$C) (SEQ ID NO: 4; wherein "F$_D$" denotes D-phenylalanine), cyclo(RGDF$_D$K) (SEQ ID NO: 7), and cyclo(RADF$_D$K) mutant peptide (SEQ ID NO:8) were purchased from Peptides International (Louisville, Ky.). N-hydroxysuccinimide (NHS), n-(3-dimethylaminopropyl)-N'-ethylcarbodiimide hydrochloride (EDC), sodium dodecyl sulfate (SDS), and deionized ultrafiltered water (DIUF $H_2O$) were purchased from Fisher Scientific (Fairlawn, N.J.). Absolute ethanol (EtOH) was purchased from AAPER Alcohol and Chemical Co. (Shelbyville, Ky.). Thin films of 100 Å Au <111>, 20 Å Ti on 1"×3"×0.040" glass were purchased from Platypus Technologies, LLC (Madison, Wis.).

The purity of purchased peptides was assumed as HPLC purity provided by the manufacturer.

Polymer stencils containing arrays of wells were created using soft lithography. Master molds containing arrays of 1.2 mm, 1.8 mm, and 2.4 mm diameter circular posts or oval-shaped or quatrefoil-shaped posts were fabricated from SU-8 (Microchem, Newton, Mass.) spin-coated silicon wafers using conventional photolithography techniques. Polydimethylsiloxane (PDMS) (Sylgard 184, Dow Corning, Midland, Mich.) was prepared by mixing a 10:1 ratio of base:curing agent (w/w) followed by degassing for approximately 45 minutes. The degassed mixture was cast over the mold and cured for 6 hours at 80° C. Following curing, PDMS stencils were removed from molds and cleaned in hexane using overnight Soxhlet extraction.

Gold slides were placed into a 150 mm glass Petri dish, covered with EtOH and sonicated for 2 minutes using an ultrasonic bath (Bransonic 1510, Branson, Danbury, Conn.). Sonicated gold chips were then rinsed with EtOH and blown dry with $N_2$. As illustrated in FIG. 11, SAM arrays were fabricated as follows: elastomeric stencils with arrays in the shape of circles, ovals, or quatrefoils were placed on a bare gold surface to form an array of wells having these shapes on the gold substrate. Wells were then filled with 1 mM ethanolic alkanethiolate solution and incubated for approximately 10 minutes at room temperature in a chamber containing a laboratory wipe soaked in ethanol to prevent evaporation during local SAM formation. Alkanethiolate solutions were then aspirated and wells were rinsed with DIUF $H_2O$. Carboxylate groups were then converted to active ester groups by adding a solution of 100 mM NHS and 250 mM EDC (in pH 5.5 DIUF $H_2O$) to wells and incubating for 15 minutes. After an additional rinse with DIUF $H_2O$, 300 µM solutions of peptide(s) in pH 7.4 PBS were added to each well and incubated for 1 hour in a humidity-controlled chamber at room temperature to covalently couple peptides to each array spot. After a final rinse in DIUF $H_2O$, regions surrounding array spots were backfilled with HS—C11-EG3-OH. This was accomplished by submerging the gold substrate and attached elastomeric stencil in an aqueous 0.1 mM HS—C11-EG3-OH solution (pH 2.0), removing the stencil, and incubating for 10 minutes. Following backfilling, the array was rinsed with 0.1 wt % SDS in DIUF $H_2O$, DIUF $H_2O$, and EtOH, and then dried under a stream of $N_2$. Arrays were stored away from light in di$H_2O$ at room temperature and used within 24 hours.

Pluripotent stem cells (H1 hESC line) were seeded on arrays at a density of approximately $2\times10^5$ cells/cm$^2$ to achieve confluent monolayers within 4 hours. Cells were cultured on SAMs in E8 medium with ROCK inhibition (using Y-27632) for 2 hours after seeding, before SAM arrays were rinsed in basal medium to remove nonspecifically adhered cells and replaced in E8 medium with Y-27632.

Colonies were analyzed for Oct4 and Nanog expression by immunofluorescence using DAPI to stain nuclei.

Figure 13:
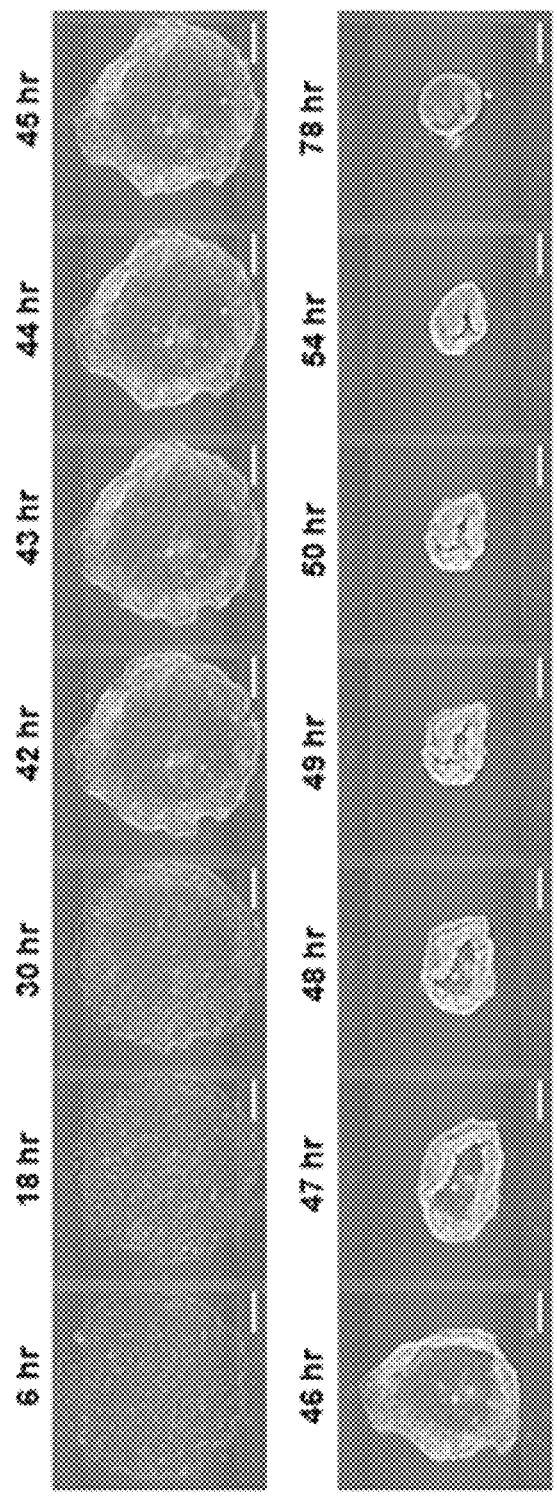
FIG. 13 depicts the nature and time scale of hESC aggregate self-assembly from 2D monolayers, as shown on 5% cyclo(RGDF$_D$C) (SEQ ID NO:4) SAMs and analyzed in Example 2. hESC monolayers were cultured on 1.2 mm diameter patterned SAM spots. Scale bars represent 250 μm.
Figure 14A:
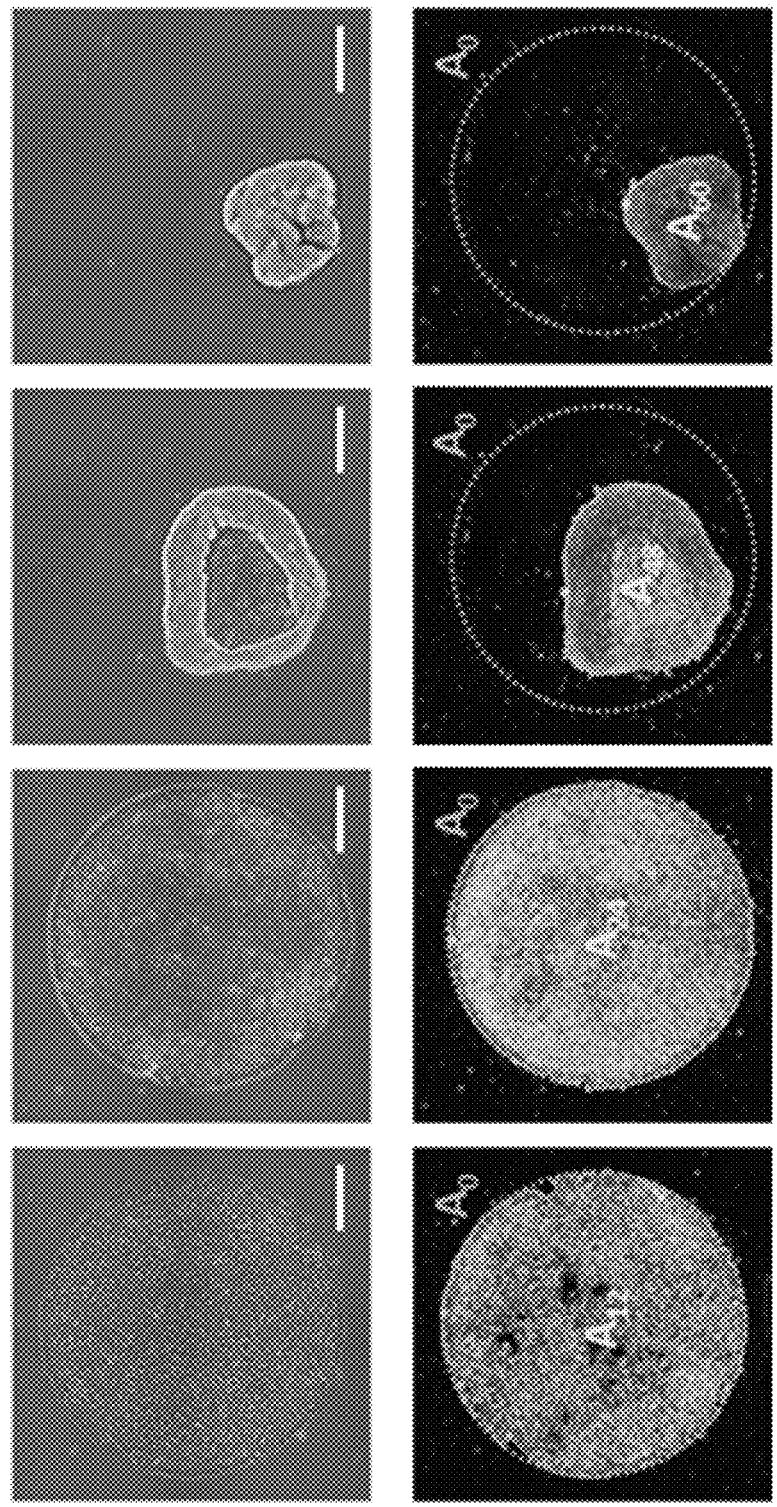
FIG. 14A depicts an image analysis method for assessing kinetics of aggregate self-assembly as used in Example 2. Timelapse images in phase contrast were acquired beginning at t=4 hours after initial cell seeding. Each frame of the timelapse acquisition was subjected to automated edge detection and automated ROI area detection using Nikon NIS Elements software. $A_0$ is defined as the area of the patterned cell population measured at t=4 hours. Percent of original spot area at a given time, n, in hours=$A_n/A_0$, where n≥4. Percent of original spot area was then plotted against n in hours, to give representative traces indicative of kinetics of cell aggregate self-assembly. Scale bars represent 250 μm.
Figure 14B:
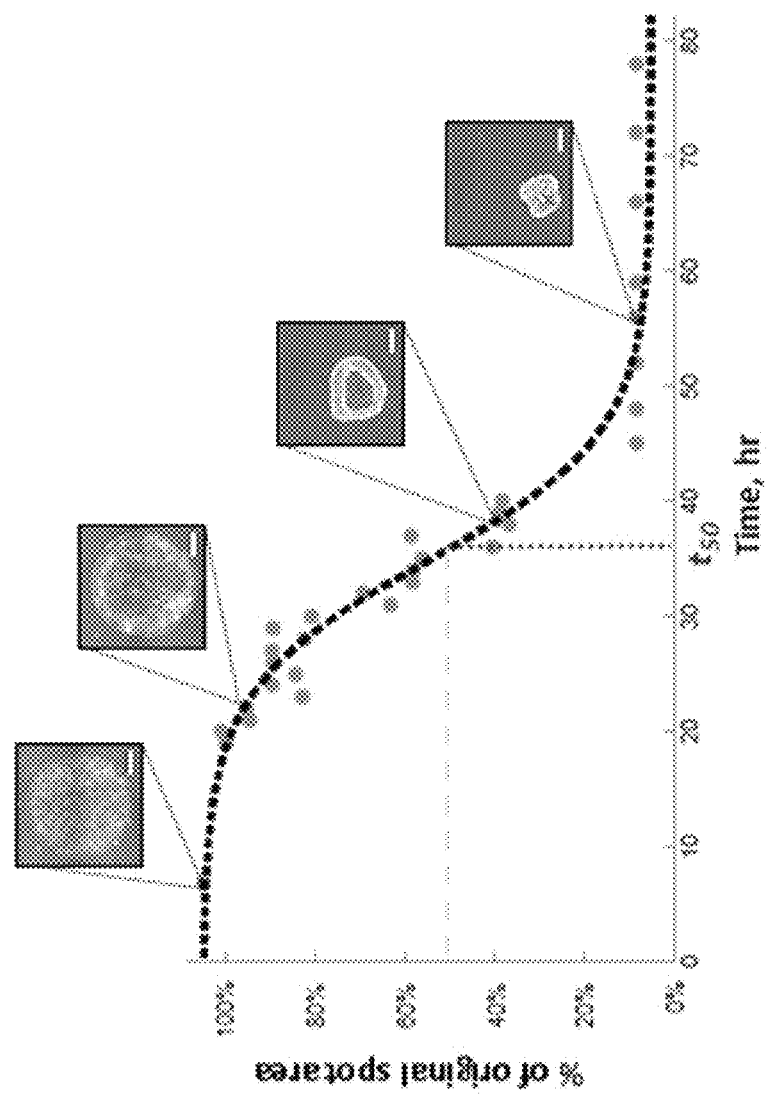
FIG. 14B depicts a sample trace generated by edge detection image analysis of timelapse images of self-assembling human embryonic stem cell populations, following approaches described in FIG. 14A. $t_{50}$ indicates the time point at which a given population (i.e., cell monolayer cultured on an individual patterned spot) reaches 50% of its original 2D projected area, and is used to assess the kinetics with which a cellular self-assembly process occurs. Scale bars represent 250 μm.

Self-assembly behavior of hESC monolayers was observed in certain conditions. This self-assembly phenomenon is described as detachment of cells from the underlying SAM and folding or contraction of monolayer edges to form a tight aggregate of cells (see t=78 hour condition in FIG. 13). As shown in FIG. 14A, the change in morphology of hESC colonies cultured on circular array spots was followed over time, usually beginning at approximately 4 hours after seeding. Time lapse images were analyzed using edge detection software to track projected area of colonies with respect to initial colony area over time. A $t_{50}$ of self-assembly was defined as the length of time required for a given patterned cell monolayer to reach 50% of its original 2D projected area, as assessed by automated edge detection. This metric is used throughout this specification to describe differences in the kinetics of aggregate self-assembly between different cell types and in different conditions.

Figure 15:
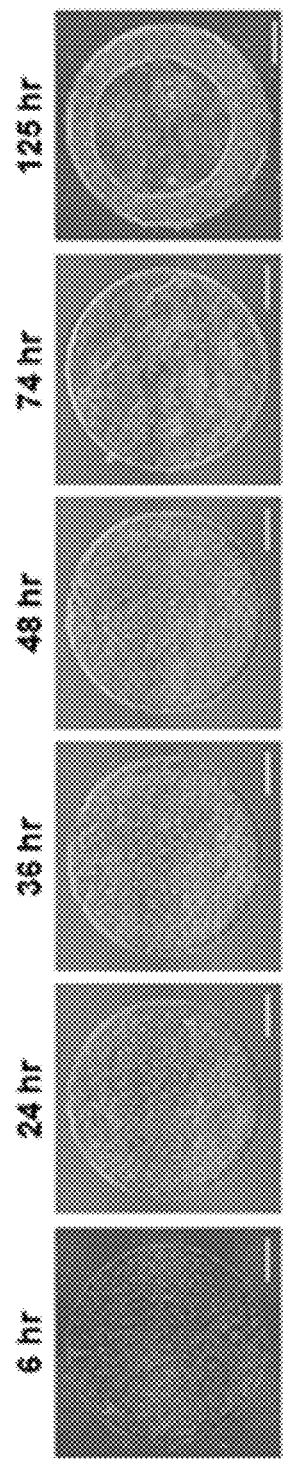
FIG. 15 depicts non-labile SAMs as analyzed in Example 2. In particular, in contrast to labile SAMs presenting cyclo(RGDF$_D$C) (SEQ ID NO:4), hESCs do not undergo self-assembly on non-labile SAMs, as shown over >5 days on 5% cyclo(RGDF$_D$K) (SEQ ID NO:7) SAMs. Scale bars represent 250 μm.

Using the image analysis methods described above, the particular identity of adhesion ligands used in the array spot was found to influence cellular self-assembly behavior. Adhesion peptides coupled to SAM spots via labile chemistry exhibited cellular self-assembly behavior while nearly identical peptides coupled via non-labile chemistry did not. As shown previously in FIG. 13, on 5% COOH SAMs presenting cyclo(RGDF$_D$C) (SEQ ID NO: 4), hESCs formed confluent monolayers by 4 hours and remained as two-dimensional monolayers until at least 24 hours. The edges of hESC monolayers began to detach thereafter, typically between 36 and 48 hours, forming three-dimensional cellular aggregates floating in suspension by 72-96 hours. Cellular aggregate formation and detachment from cyclo(RGDF$_D$C) (SEQ ID NO:4) SAM surfaces into suspension occurred in the absence of mechanical manipulation or enzymatic treatment. In contrast, on 5% COOH SAMs presenting cyclo(RGDF$_D$K) (SEQ ID NO: 7), hESCs formed similar confluent monolayers but exhibited no cellular self-assembly behavior. As shown in FIG. 15, SAMs presenting cyclo(RGDF$_D$K) (SEQ ID NO:7) allowed no observable detachment of hESC monolayers over 96 hours. Furthermore, minimal cell detachment occurred on cyclo (RGDF$_D$K) (SEQ ID NO:7) SAMs over 1 week in culture and in contrast to cyclo(RGDF$_D$C) (SEQ ID NO:4) SAMs, these conditions did not result in the formation of floating cell aggregates (not shown).

Figure 16A:
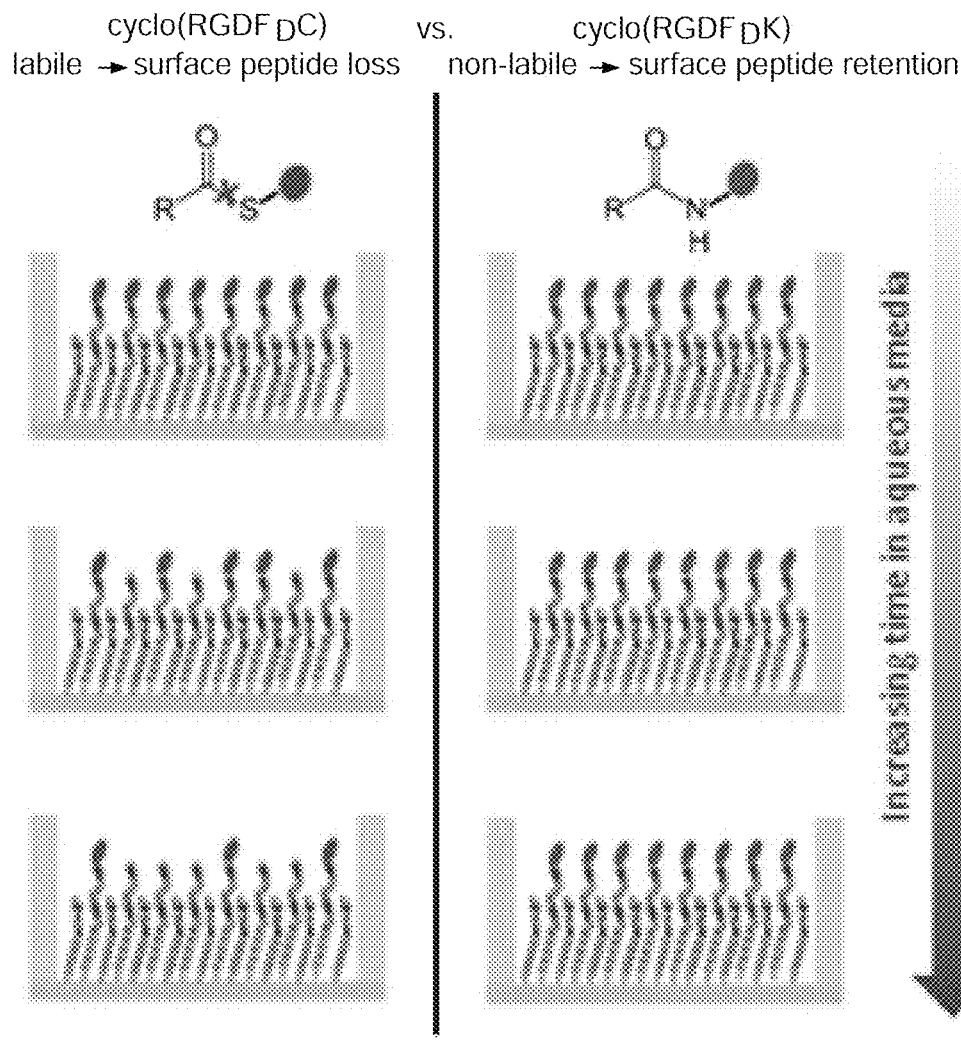
FIG. 16A is a schematic illustrating the proposed mechanism of cellular self-assembly mediated by loss of peptide over time due to hydrolysis on labile SAMs, but not on non-labile SAMs, as analyzed in Example 2.
Figure 16B:
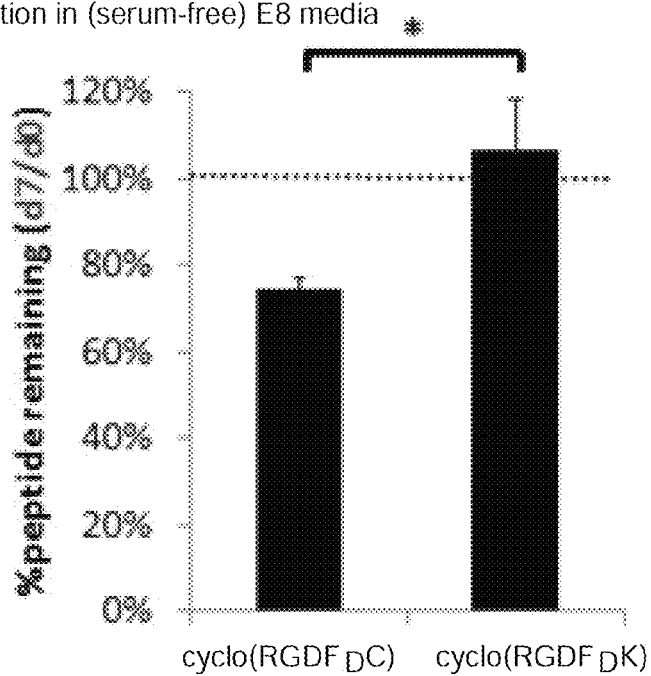
FIG. 16B depicts x-ray photoelectron spectroscopy surface analysis as used in Example 2, which demonstrates that peptide content over 7 days decreases significantly on "labile" SAMs presenting cyclo(RGDF$_D$C) (SEQ ID NO:4), but remains unchanged on "non-labile" SAMs cyclo(RGD-F$_D$K) (SEQ ID NO:7) in protein-containing cell culture media. Error bars represent ±1 standard deviation. Asterisks denotes statistical significance between conditions (Student's t-test, p<0.05). Non-labile cyclo(RGDF$_D$K) (SEQ ID NO:7) SAMs did not show significantly different surface peptide content compared to day 0 conditions.
Figure 16C:
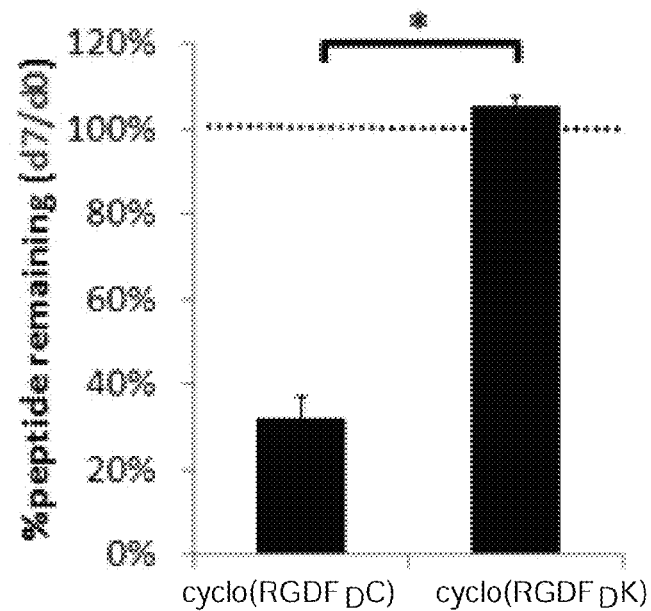
FIG. 16C depicts peptide loss from labile SAMs during incubation in protein-free aqueous conditions as analyzed in Example 2. X-ray photoelectron spectroscopy surface analysis demonstrates that peptide content over 7 days decreases significantly on "labile" SAMs presenting cyclo(RGDF$_D$C) (SEQ ID NO:4), but remains unchanged on "non-labile" cyclo(RGDF$_D$K) (SEQ ID NO:7) SAMs incubated in phosphate-buffered saline.
Figure 16D:
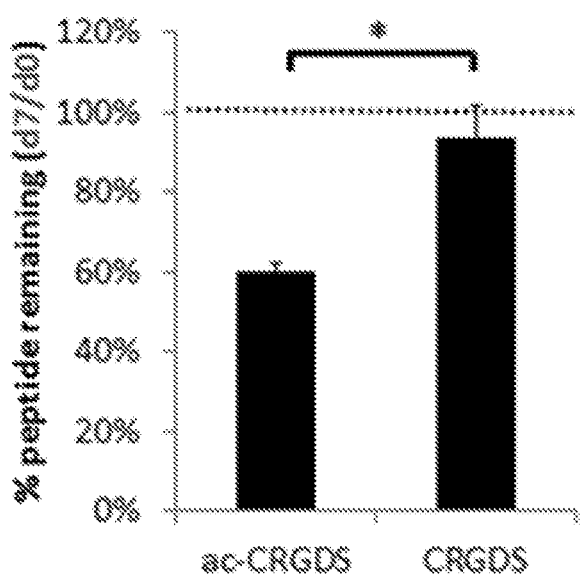
FIG. 16D depicts that peptide loss from labile SAMs during incubation in aqueous conditions is generalizable to labile chemistry, and is not specific to cyclic peptides. X-ray photoelectron spectroscopy surface analysis demonstrates that peptide content over 7 days decreases significantly on "labile" SAMs presenting acetylated-CRGDS (SEQ ID NO:9), but remains unchanged on "non-labile" CRGDS (SEQ ID NO:9) SAMs incubated in phosphate-buffered saline. Error bars represent ±1 standard deviation. Asterisks denote statistical significance between conditions (Student's t-test, p<0.05). Non-labile (i.e., cyclo(RGDF$_D$K) (SEQ ID NO:7) or CRGDS (SEQ ID NO:9)) SAMs did not show significantly different surface peptide content compared to day 0 conditions of the corresponding peptide.

To show that cellular aggregate self-assembly on SAMs was specific to the lability of the chemistry used, surface analysis was performed to assess the potential for labile chemistry to result in accelerated loss of peptide from the surface over time (see FIG. 16A, schematic). Here, X-ray photoelectron spectroscopy (XPS) analysis of 100% COOH SAMs presenting either cyclo(RGDF$_D$C) (SEQ ID NO:4) ("labile SAMs") or cyclo(RGDF$_D$K) (SEQ ID NO:7) ("non-labile SAMs") was performed over a 7-day incubation in serum-free cell culture medium (E8) in the absence of cells. As shown in FIG. 16B, adhesion peptides coupled to SAM spots via labile chemistry exhibited significant loss of surface peptide during incubation in aqueous cell culture media, while nearly identical peptides coupled via non-labile chemistry did not. Specifically, approximately 25% of surface peptide was lost from labile SAMs over 7 days in cell culture medium, while no significant loss of peptide was observed in the case of non-labile (cyclo(RGDF$_D$K)) (SEQ ID NO:7) SAMs incubated over the same time frame.

Figure 17A:
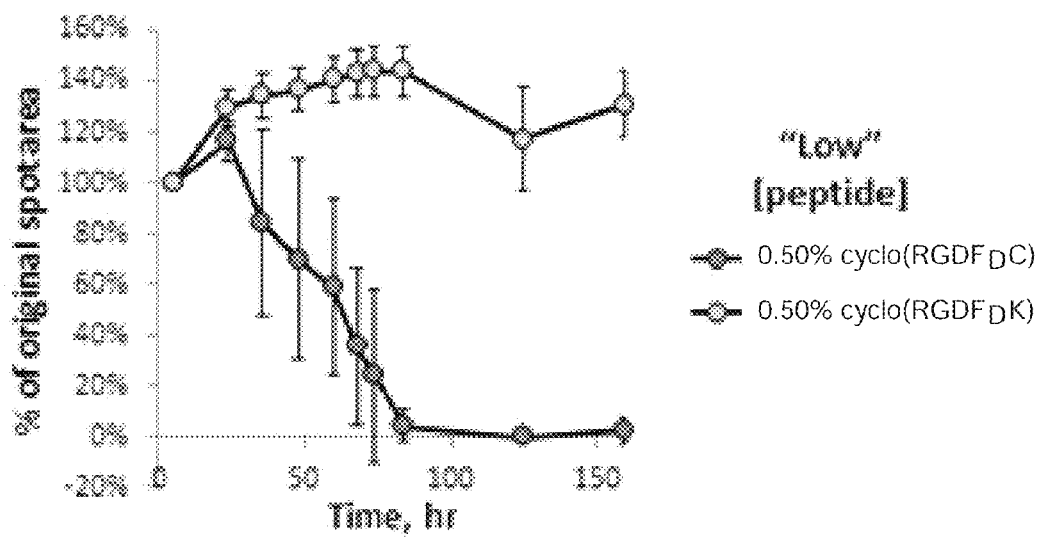
FIGS. 17A and 17B depict traces demonstrating change in population area over time for hESCs cultured on SAMs presenting either labile (cyclo(RGDF$_D$C) (SEQ ID NO:4)) or non-labile (cyclo(RGDF$_D$K) (SEQ ID NO:7)) chemistry at 0.5% ("low") or 5% ("high") total peptide density. Independent of total peptide density across the ranges shown, "labile" SAMs presenting cyclo(RGDF$_D$C) (SEQ ID NO:4) promoted hESC self-assembly as demonstrated by evident decreases in population area over time, while "non-labile" cyclo(RGDF$_D$K) (SEQ ID NO:7) SAMs prohibited hESC self-assembly. Error bars represent standard error, represented at 95% confidence interval.
Figure 17B:
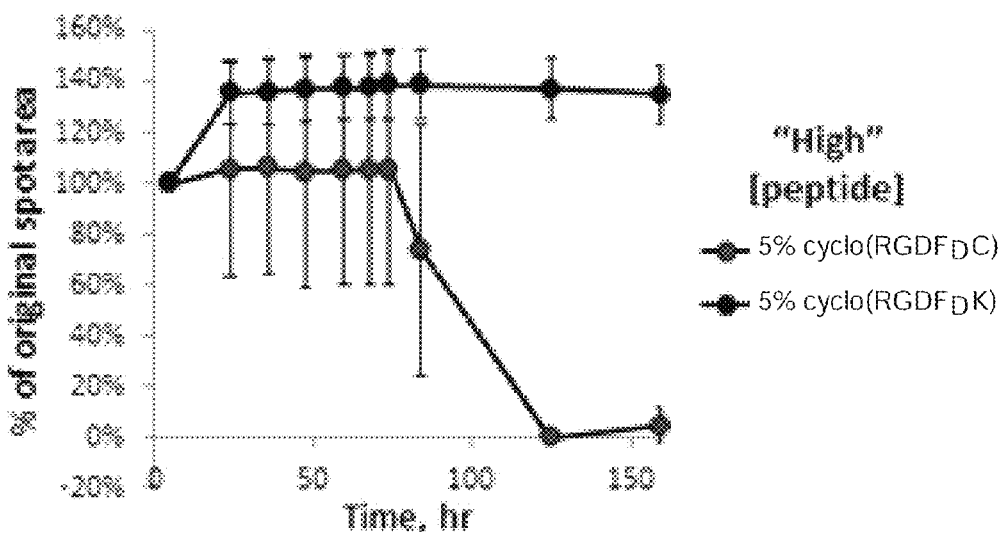
Figure 17C:
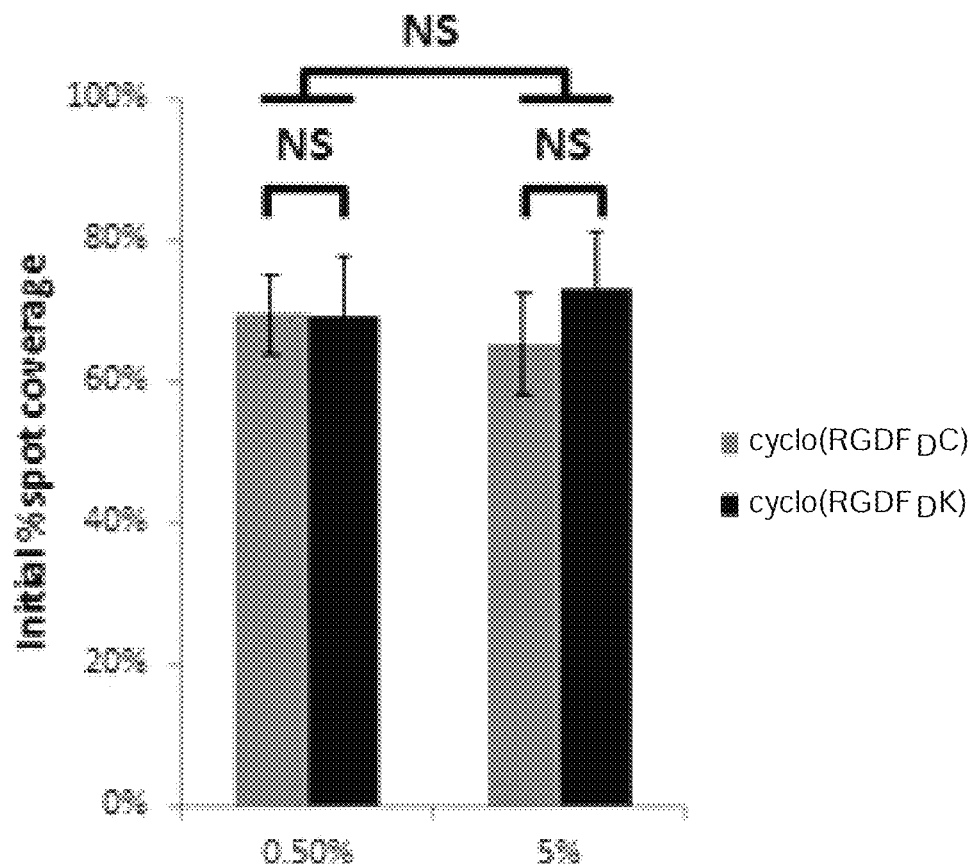
FIG. 17C depicts hESC initial adhesion, as measured by initial percentage of spot coverage, to labile and non-labile cyclic RGD SAMs as analyzed in Example 2. Particularly, there is no significant difference between the two peptides or within the ranges of peptide density shown, suggesting that lability of the chemical bond between SAM and peptide dictates whether cellular self-assembly occurs. "NS" denotes no statistical significance between indicated groups. Error bars represent ±1 standard deviation. Asterisks denote statistical significance between indicated conditions.

Whether cellular aggregate self-assembly behavior was observed on SAMs presenting a particular cyclic RGD peptide was independent of peptide density in the range tested. In this Example, total peptide density on the array spot was varied by changing the fraction of reactive COOH groups functionalized with peptides among background non-reactive OH functionalities. As shown in FIGS. 17A & 17B, evident decreases in hESC colony projected area, indicative of aggregate self-assembly, occurred on both 5% COOH and 0.5% COOH SAMs presenting cyclo(RGDF$_D$C) (SEQ ID NO:4). In contrast, no such decreases in hESC colony projected area were observed on either 5% COOH or 0.5% COOH SAMs presenting cyclo(RGDF$_D$K) (SEQ ID NO:7). Furthermore, initial (4-hour) hESC attachment to SAMs presenting 0.5% or 5% total peptide was similar irrespective of which cyclic peptide was coupled, suggesting that differences in bioactivity or initial cell seeding coverage between the two cyclic RGD peptides were not responsible for the phenomenon of cellular aggregate self-assembly (FIG. 17C). The results support the concept that lability of the bond between SAM surfaces and adhesion peptides is a driving force for cellular aggregate self-assembly.

Figure 18A:
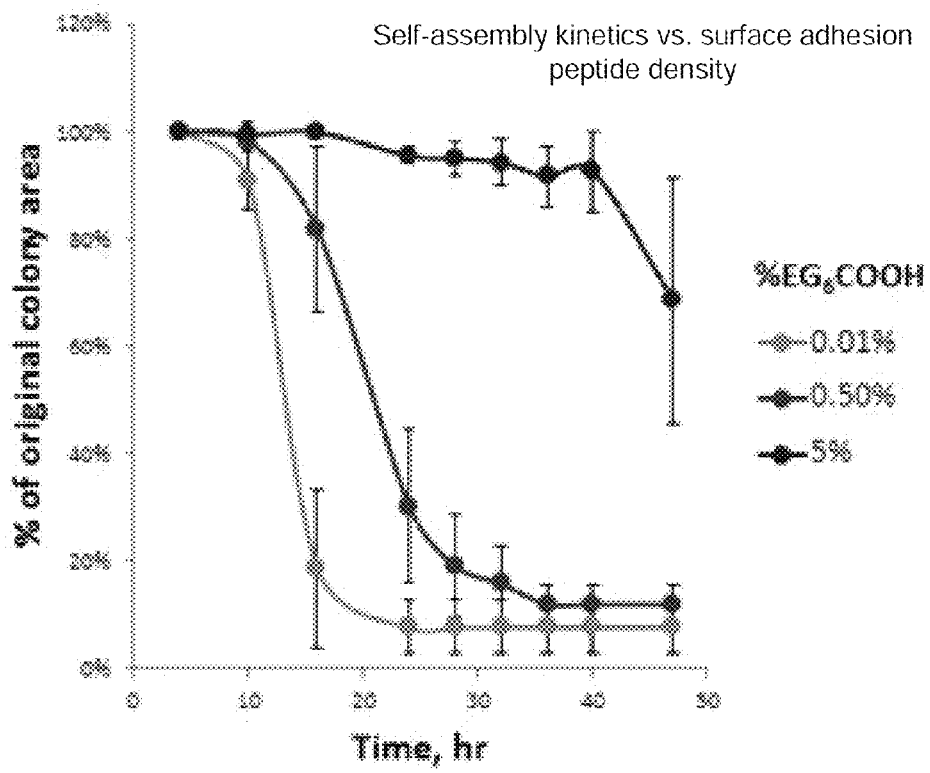
FIGS. 18A and 18B indicate that the changing total surface peptide density on labile SAMs influences the kinetics of cellular aggregate self-assembly.
Figure 18B:
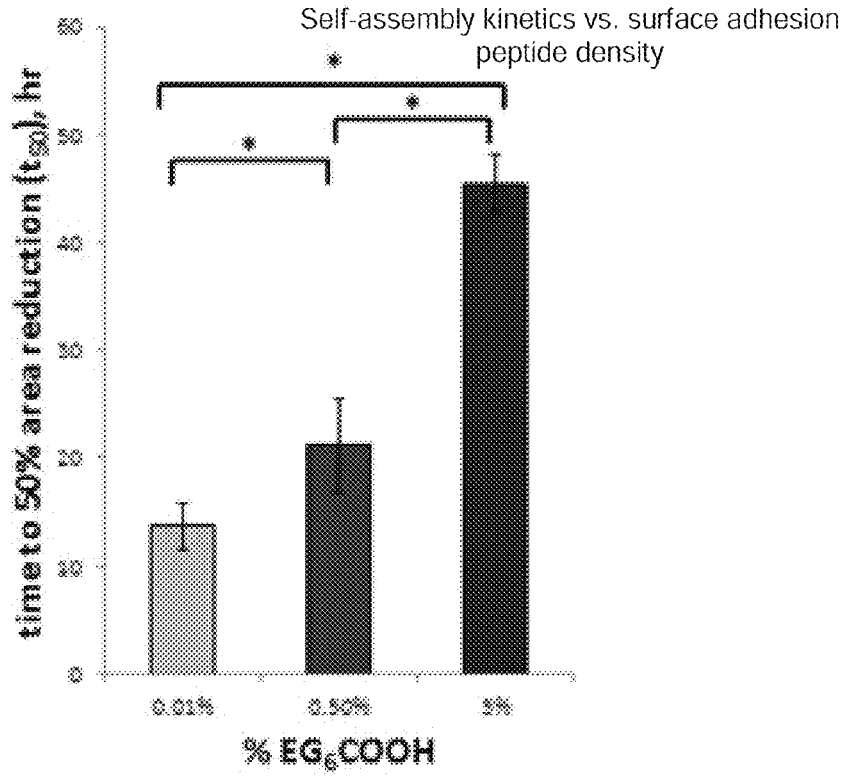

The density of the integrin adhesion peptide cyclo(RGDF$_D$C) (SEQ ID NO: 4) could be controlled in order to influence the timing of cellular aggregate self-assembly. Here, the concentration of cyclo(RGDF$_D$C) (SEQ ID NO:4) peptide on SAMs ranged from 0.01% COOH to 5% COOH. As previously shown in FIG. 13, hESC monolayers seeded onto 5% COOH cyclo(RGDF$_D$C) (SEQ ID NO:4) SAMs began the self-assembly process at 40-48 hours post-seeding, on average. Here, hESC monolayers on 5% cyclo (RGDF$_D$C) (SEQ ID NO:4) SAMs reached $t_{50}$ at approximately 45 hours. hESC monolayers on 0.5% COOH cyclo (RGDF$_D$C) (SEQ ID NO:4) SAMs underwent self-assembly into cellular aggregates with accelerated kinetics compared to those on 5% cyclo(RGDF$_D$C) (SEQ ID NO:4) SAMs, reaching $t_{50}$ at approximately 22 hours. Finally, hESC monolayers on 0.01% cyclo(RGDF$_D$C) (SEQ ID NO:4) SAMs exhibited the fastest rate of self-assembly, reaching $t_{50}$ at approximately 14 hours. These results demonstrate that decreasing surface density of cyclo(RGDF$_D$C) (SEQ ID NO:4) leads to an acceleration of the cell aggregate self-assembly process (see FIGS. 18A & 18B).

Figure 19:
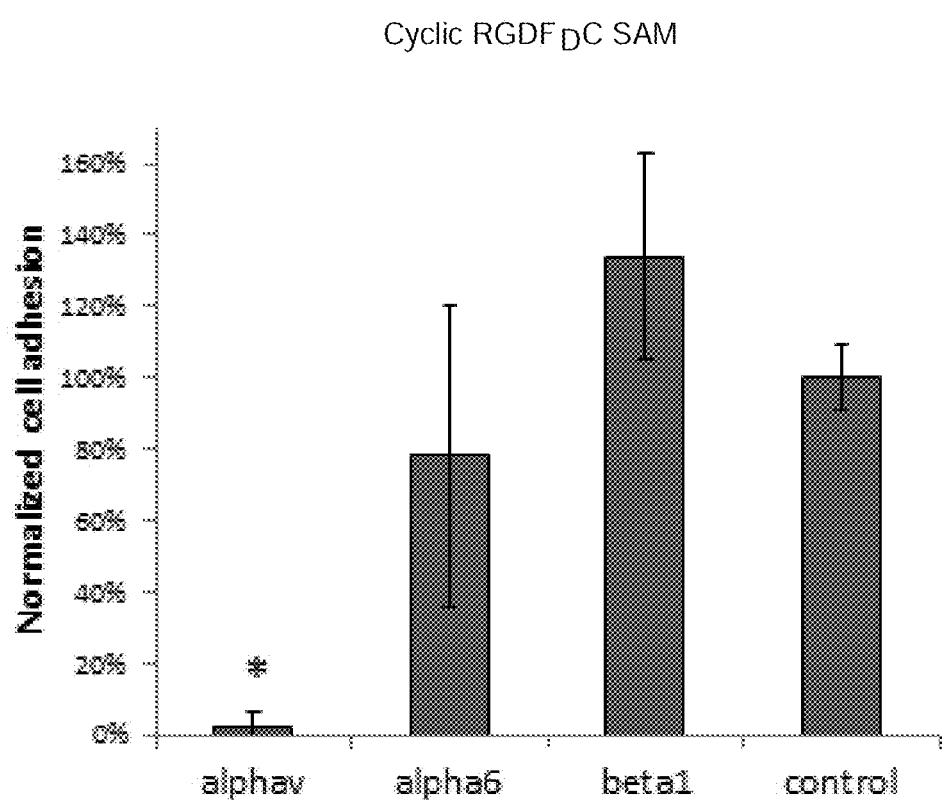
FIG. 19 depicts that hESC adhesion to cyclic RGD-presenting SAMs is mediated by $\alpha_v$-type integrins. Addition of $\alpha_v$ integrin-blocking antibody drastically decreases ability of hESCs to adhere to cyclo(RGDF$_D$C) (SEQ ID NO:4) SAMs, while blocking antibodies to other integrin subtypes had no effect on hESC adhesion to cyclo(RGDF$_D$C) (SEQ ID NO:4) SAMs. Error bars represent ±1 standard deviation. Asterisk denotes statistical significance in comparison to all other conditions (Student's t-test, p<0.05). Control condition denotes no antibody added.

Adhesion of hESCs to cyclo(RGDF$_D$C) (SEQ ID NO:4) SAMs was mediated by $\alpha_v$-type integrins. As shown in FIG. 19, function-blocking antibodies against $\alpha_v$ integrin drastically knocked down initial hESC adhesion to 5% cyclo (RGDF$_D$C) (SEQ ID NO:4) SAMs, while antibodies against $\beta_1$ integrin and $\alpha_6$ integrin had no significant effect on initial hESC adhesion. This result also suggested that blocking interactions between cyclo(RGDF$_D$C) (SEQ ID NO:4) presented by SAMs and $\alpha_v$ integrins is a strategy that could potentially be used to modulate hESC adhesion to cyclo (RGDFDC) (SEQ ID NO:4) SAMs.

Figure 20A:
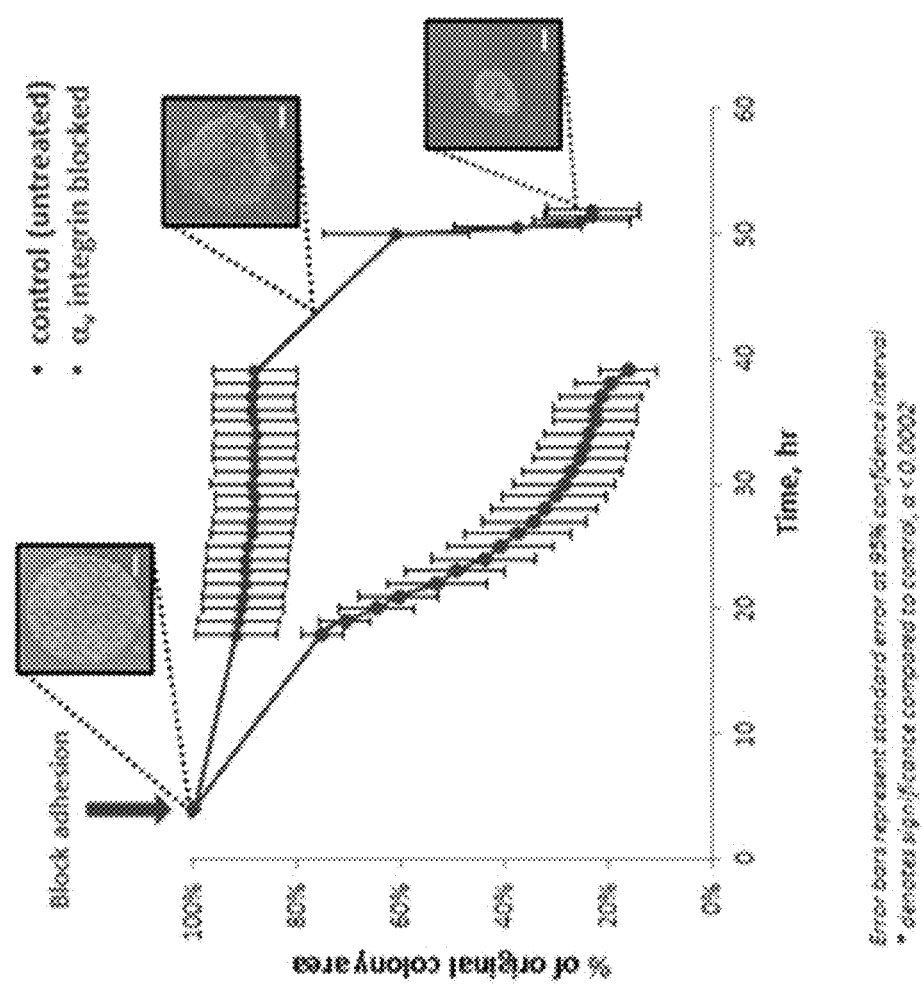
FIGS. 20A and 20B show that changing the degree of cell-material adhesion on labile SAMs via addition of $\alpha_v$ integrin-blocking antibody influences the kinetics of cellular aggregate self-assembly as analyzed in Example 2.

The degree of cell-material adhesion, mediated by specific cell-surface integrin binding to adhesion peptides, also influenced the timing of cellular aggregate assembly on cyclo(RGDF$_D$C) (SEQ ID NO:4) SAMs. As shown in FIG. 20A, inhibiting adhesion of confluent hESC monolayers to 5% cyclo(RGDF$_D$C) (SEQ ID NO:4) SAMs via addition of function-blocking antibody against $\alpha_v$ integrin accelerated cellular aggregate assembly in comparison to control conditions in which monolayers were allowed to self-assemble in the absence of antibody.

Figure 20B:
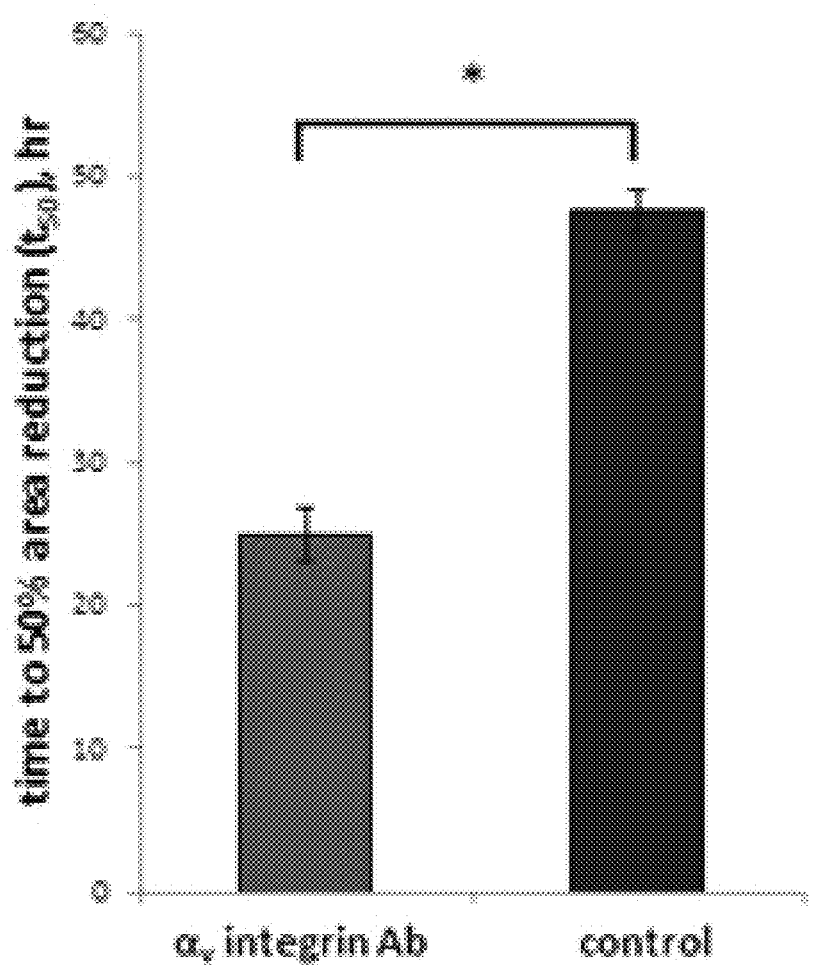
Figure 21:
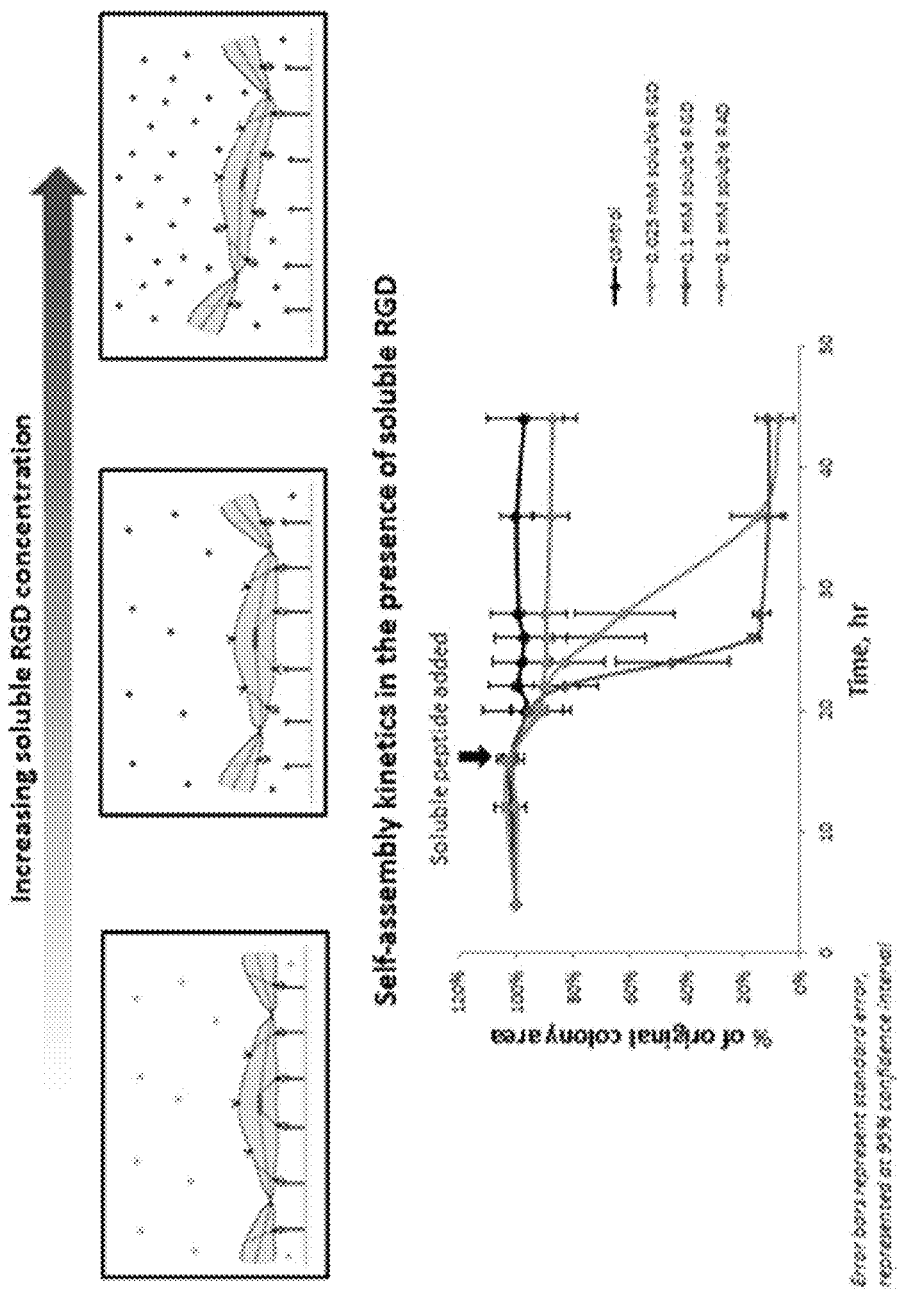
FIG. 21 depicts that changing the degree of cell-material adhesion on labile SAMs via addition of soluble RGD influences the kinetics of cellular aggregate self-assembly. At the bottom, traces demonstrate change in population area over time for hESCs cultured on 5% cyclo(RGDF$_D$C) (SEQ ID NO:4) SAMs in the presence of varying concentrations of soluble RGD peptide. Soluble cyclo(RGDF$_D$C) (SEQ ID NO:4) (green) competes with surface-tethered cyclo(RGDF$_D$C) (SEQ ID NO:4) in a concentration-dependent manner to increase the rate of hESC aggregate self-assembly on 5% cyclo(RGDF$_D$C) (SEQ ID NO:4) SAMs compared to control conditions in which no soluble peptide was added (black). Addition of an equivalent concentration of the mutant peptide cyclo(RADF$_D$K) (SEQ ID NO:7) (orange) has minimal effect on hESC self-assembly during the assessed time period. Error bars represent standard error, represented at 95% confidence interval.

As shown in FIG. 21, soluble cyclic RGD adhesion peptides could be used to modulate hESC adhesion to cyclo(RGDF$_D$C) (SEQ ID NO:4) SAMs, thereby influencing the timing of cellular aggregate assembly. In particular, addition of soluble cyclo(RGDF$_D$C) (SEQ ID NO:4) to culture media was shown to accelerate the assembly behavior of cellular aggregates on 5% cyclo(RGDF$_D$C) (SEQ ID NO:4) SAMs in a concentration-dependent manner. Addition of 0.025 mM soluble cyclo(RGDF$_D$C) (SEQ ID NO:4) led to faster aggregate assembly in comparison to control conditions in which no adhesion ligand was added. Addition of 0.1 mM soluble cyclo(RGDF$_D$C) (SEQ ID NO:4) led to the most rapid aggregate assembly in the conditions tested. Addition of 0.1 mM soluble cyclo(RADF$_D$K) mutant peptide (SEQ ID NO:8) had no evident effect on the kinetics of cellular aggregate assembly over the time period evaluated, implying minimal nonspecific adhesion of hESCs to cyclo (RGDF$_D$C) (SEQ ID NO:4) SAMs. Altogether, these results, in combination with those of FIG. 19 and FIG. 20, suggest that cellular aggregate self-assembly is dependent on hESC $\alpha_v$ integrin-mediated adhesion to cyclo(RGDF$_D$C) (SEQ ID NO:4) SAMs. The results further suggest that this adhesion may be tailored by i) changing cyclo(RGDF$_D$C) (SEQ ID NO:4) peptide density on SAMs (FIGS. 18A & 18B), ii) blocking adhesion with $\alpha_v$ integrin-specific antibodies (FIGS. 20A & 20B), and iii) blocking adhesion with soluble RGD peptides (FIG. 21). All three of the aforementioned approaches can be used to influence the timing of cellular aggregate assembly.

SAM arrays presenting cyclo(RGDF$_D$C) (SEQ ID NO:4) could be used to generate large populations of self-assembling hESC aggregates, herein termed "embryoid bodies" (EBs). As shown in FIGS. 22A-22C, hESC monolayers on 5% cyclo(RGDF$_D$C) (SEQ ID NO:4) SAMs patterned in circular spots of 1.2 mm diameter typically formed self-assembled EBs within 72 hours. These EBs formed from individual patterned spots in the absence of mechanical or enzymatic perturbation, and were easily collected from suspension after 72 hours.

Figure 23A:
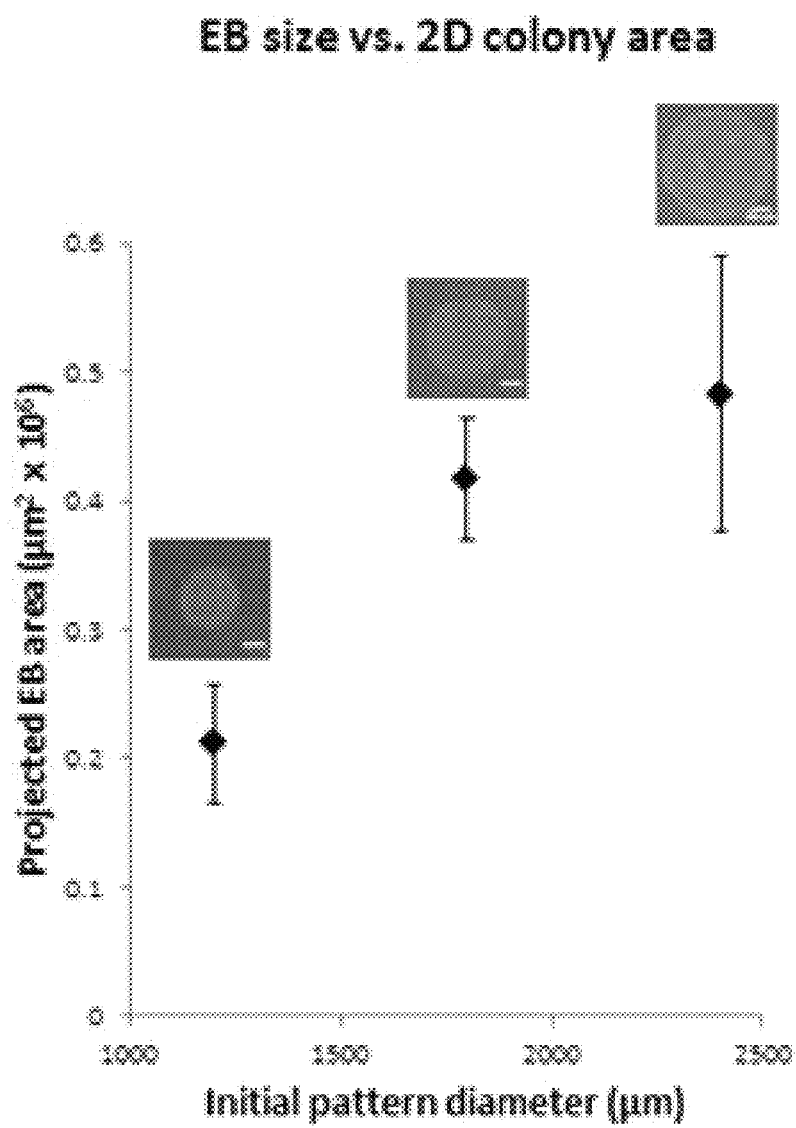
FIG. 23A depicts the projected area of EBs generated from circular patterns of varying size. Average projected area of generated EBs was approximately $2 \times 10^5$ $\mu m^2$, ~$4 \times 10^5$ $\mu m^2$, and ~$5 \times 10^5$ $\mu m^2$ for circular patterns of 1.2 mm, 1.8 mm, and 2.4 mm diameter, respectively.
Figure 23B:
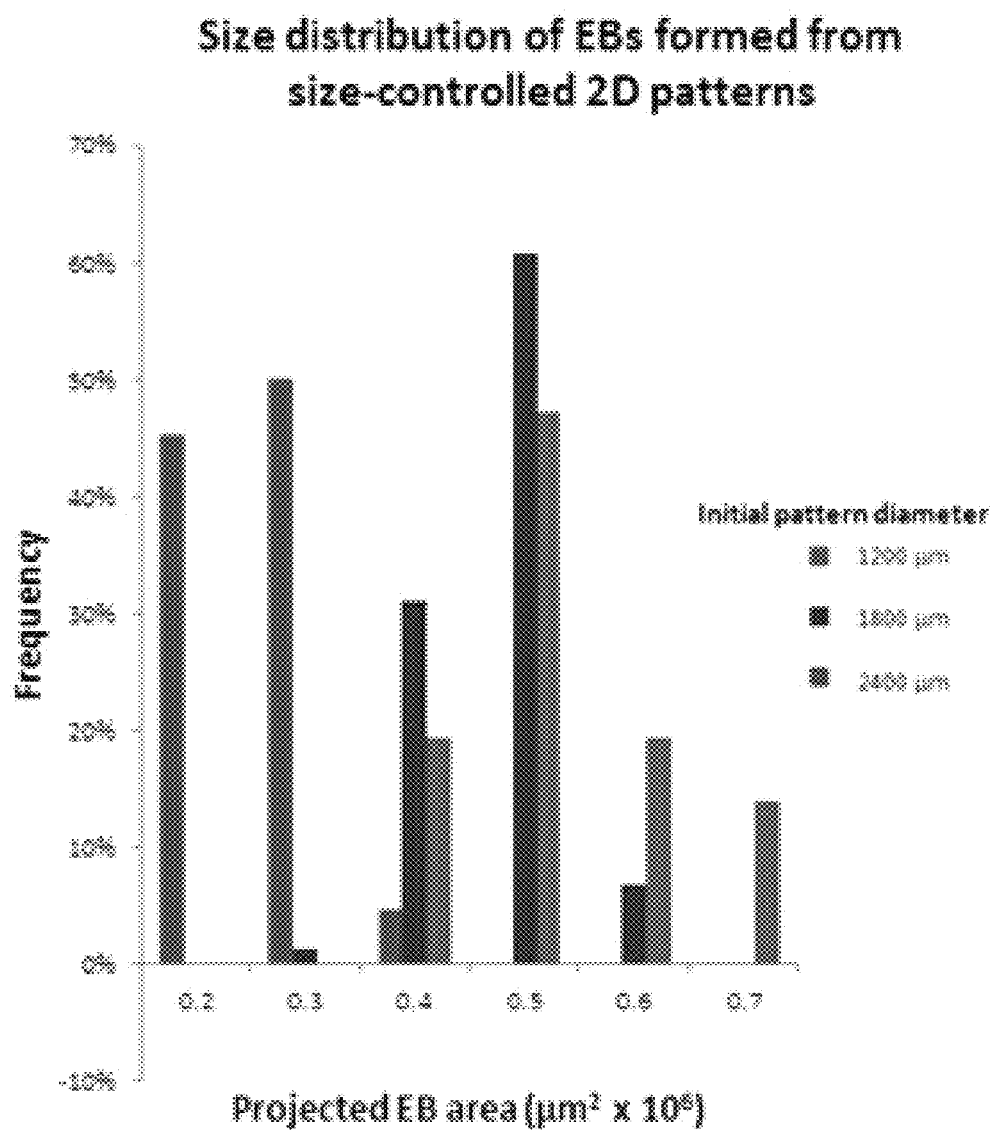
FIG. 23B depicts that EBs self-assembled from circular patterns 1.2 mm, 1.8 mm, and 2.4 mm in diameter exhibit distinct size distribution profiles. Narrow size distribution profiles are desired in applications where EB homogeneity is desired.

The size of self-assembled EBs formed from 5% COOH SAMs presenting cyclo(RGDF$_D$C) peptide (SEQ ID NO:4) was dependent on the size of initial circular patterns used to spatially localize SAMs. As shown in FIG. 23A, 1.2 mm diameter circular patterns generated EBs with average areas of ~2×10$^5$ μm$^2$, while 1.8 mm and 2.4 mm diameter patterns generated EBs with average areas of approximately 4×10$^5$ μm$^2$ and ~5×10$^5$ μm$^2$, respectively. The size distribution of EBs formed from circular patterns of the aforementioned sizes is shown in the histogram in FIG. 23B. Narrow size distribution profiles are desired in applications where EB homogeneity is desired. EB homogeneity is particularly important in the context of directed differentiation of EBs, where numerous studies have shown that EB size is a determinant of the propensity for cells of a given germ layer (i.e., endoderm, mesoderm, or ectoderm) to be generated during EB differentiation.

Figures 24A, 24B, 24C:
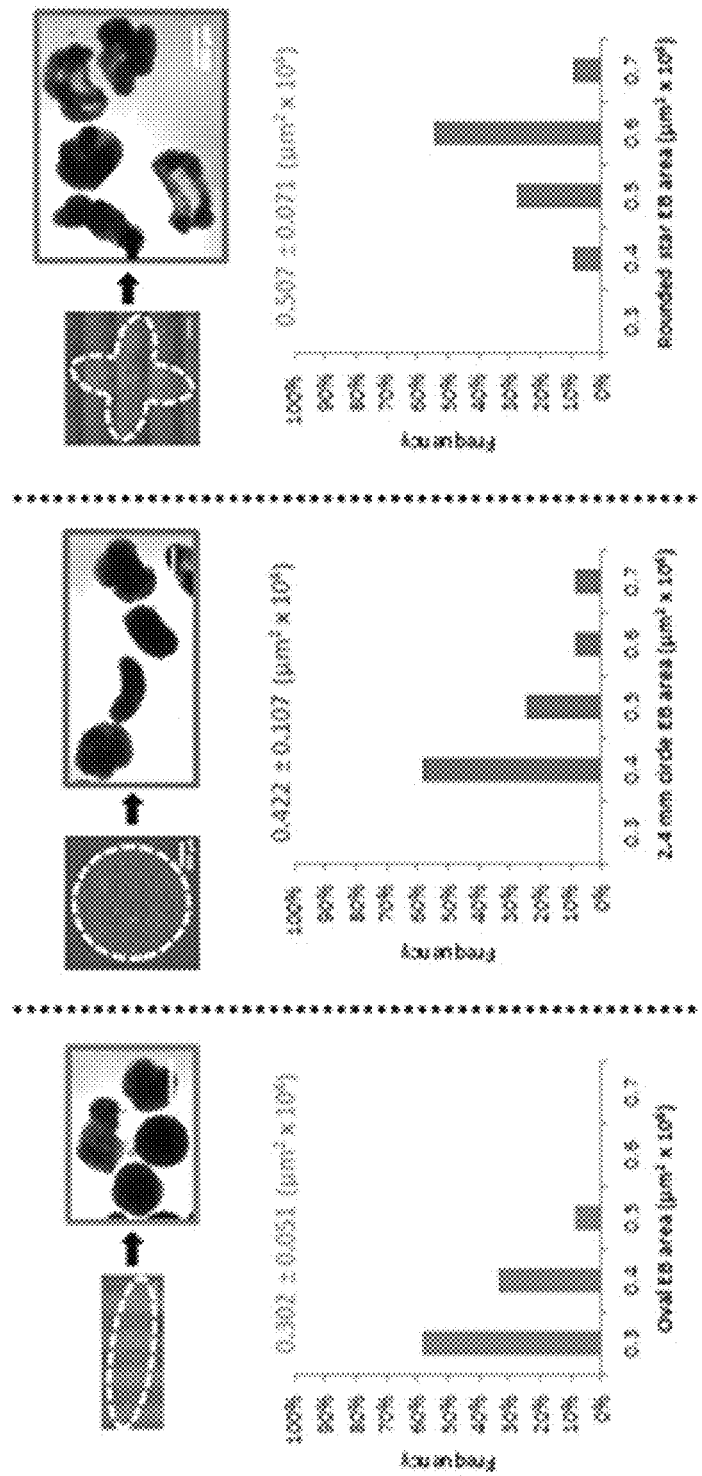
FIGS. 24A-24C depict that patterned SAM arrays of varying size and shape generate EBs with distinct size and shape profiles. Exemplary patterns demonstrated here include (24A) ovals, (24B) 2.4 mm circles, and (24C) quatrefoils. Average 2D projected area of EBs generated from a given pattern are indicated above each size distribution graph.

As shown in FIG. 24, hESC monolayers can be cultured on SAM patterns of various geometries and sizes, including (FIG. 24A) ovals, (FIG. 24B) circles, and (FIG. 24C) quatrefoils of varying size (scale bar=500 μm in all images). hESC monolayers generated on these various patterns of cyclo(RGDF$_D$C) (SEQ ID NO:4) SAMs formed self-assembled cellular aggregates of varying size and shape (shown in brightfield images in FIG. 24A-24C and corresponding graphs of aggregate size distribution). Specifically, ovals, circles, and quatrefoils of the sizes shown in FIG. 24 generated cellular aggregates with approximate average areas of 3×10$^5$ μm$^2$, 4.25×10$^5$ μm$^2$, and 5×10$^5$ μm$^2$, respectively.

Figure 25A:
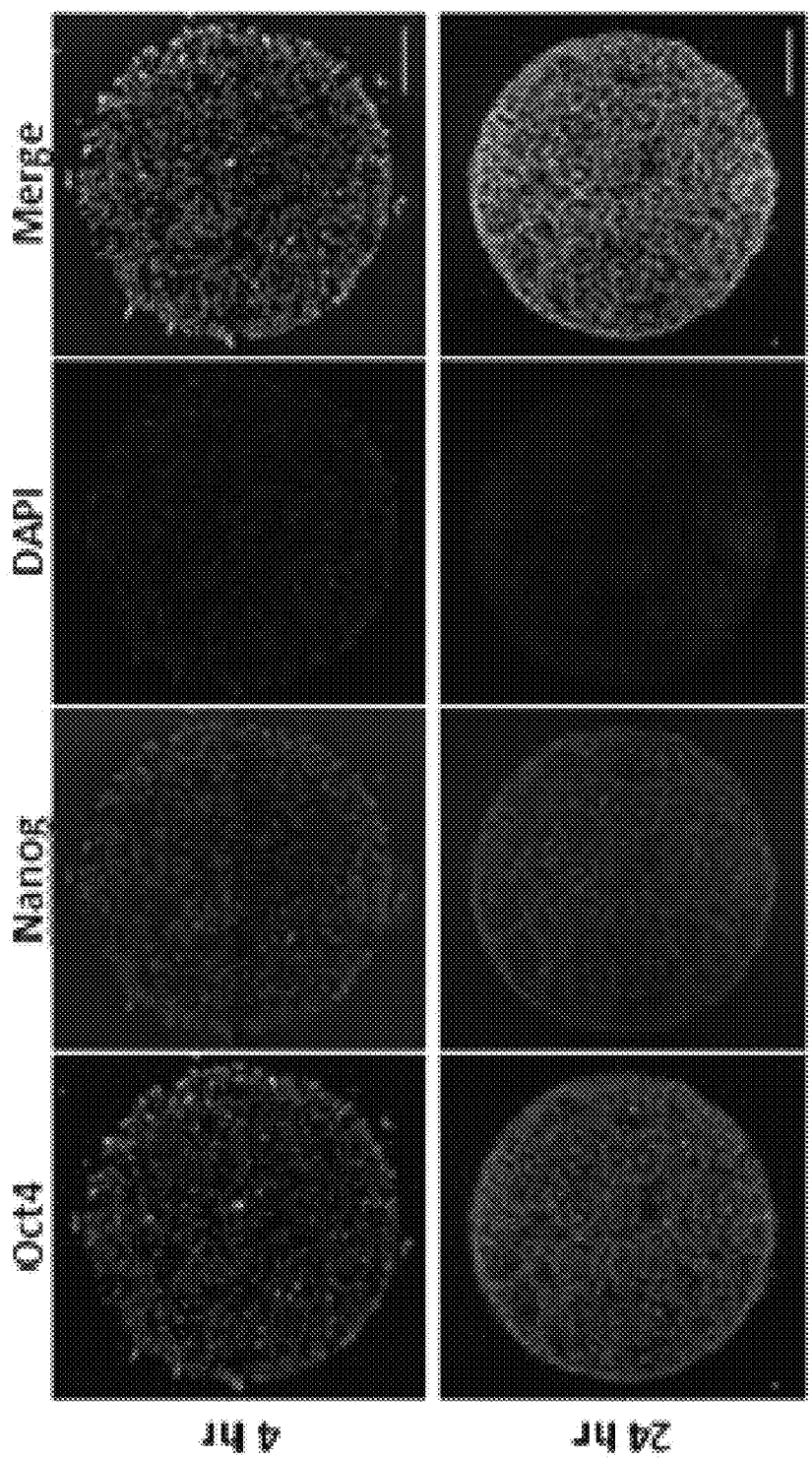
FIGS. 25A and 25B depict that self-assembled EBs formed in Example 2 from pluripotent hESC monolayers.
Figure 25B:
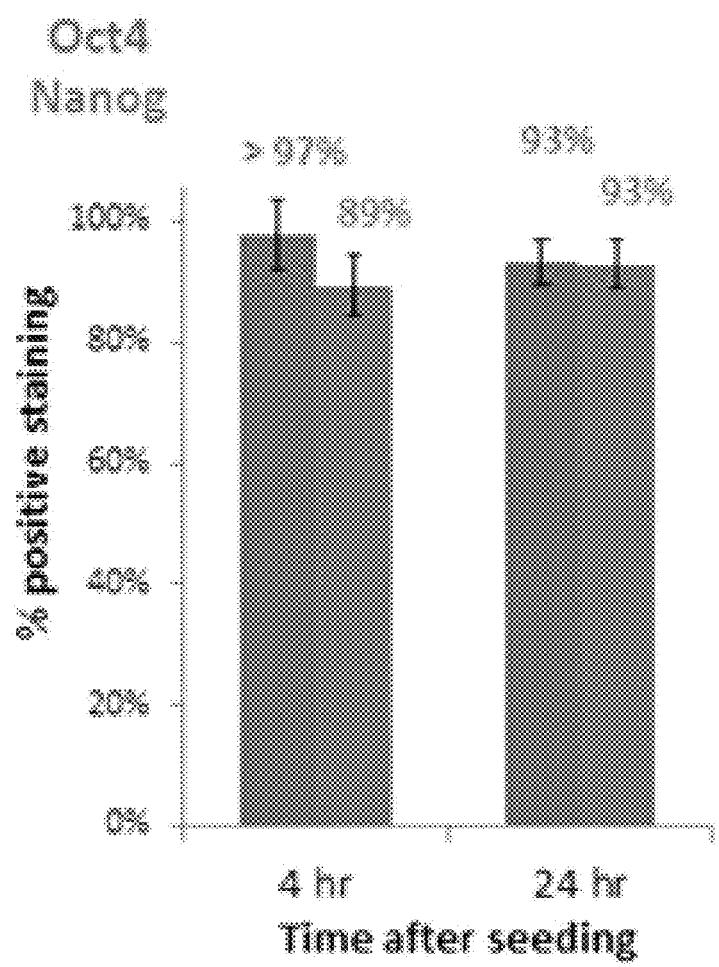

Self-assembled EBs formed from largely pluripotent 2D hESC populations. hESC monolayers cultured on array spots were stained for pluripotency markers Oct4 and Nanog, as well as DAPI to identify cell nuclei. FIG. 25A shows representative images demonstrating expression of each marker and merged images of all markers assessed, in order to demonstrate pluripotency of the cells at time points prior to self-assembly. hESC monolayers on 5% cyclo (RGDF$_D$C) (SEQ ID NO:4) SAMs are largely pluripotent at 4 hours and 24 hours after initial seeding, prior to the start of cellular aggregate self-assembly. Quantification of positive staining for Oct4 and Nanog, relative to number of cells as quantified by DAPI staining, is shown in FIG. 25B. In this Example, Oct4 was expressed by greater than 97% of hESCs in monolayers at 4 hours and was expressed by 93% of hESCs in monolayers at 24 hours. Nanog was expressed by 89% and 93% of hESCs in monolayers at 4 hours and 24 hours, respectively. These results suggest that large-scale changes in pluripotency status of cells within hESC monolayers are not required in order for the self-assembly process observed on cyclo(RGDF$_D$C) (SEQ ID NO:4) SAMs to occur.

Figure 26A:
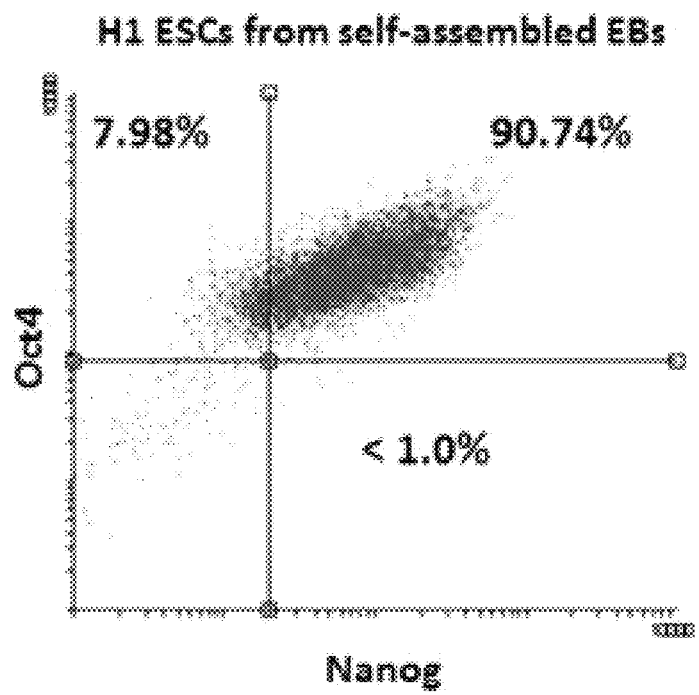
FIG. 26A depicts that self-assembled EBs maintain high levels of Oct4 and Nanog expression throughout EB self-assembly and at least 24 hours post-formation as analyzed in Example 2. Expression levels were assessed by flow cytometry of hESCs dissociated from EBs collected 24 hours after self-assembly on 5% cyclo(RGDF$_D$C) (SEQ ID NO:4) SAMs.
Figure 26B:
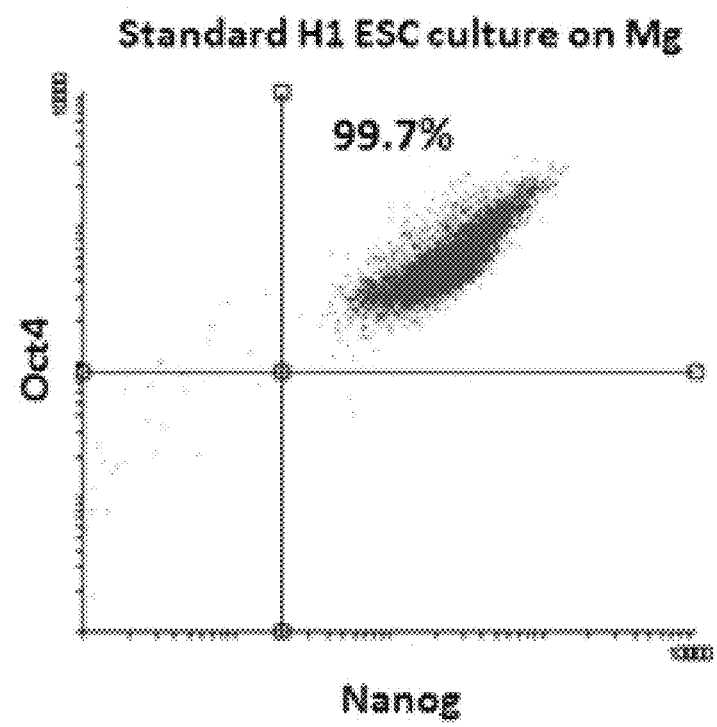
FIG. 26B depicts typical levels of Oct4 and Nanog, as expressed by hESCs maintained in routine culture on Matrigel.

Self-assembled EBs remain pluripotent throughout the self-assembly process. Self-assembled EBs from 5% cyclo (RGDF$_D$C) (SEQ ID NO:4) SAMs were collected at 24 hours post-assembly (approximately 96 hours after initial seeding) and dissociated using Accutase before being assessed for Oct4 and Nanog expression by flow cytometry. To give reference, 0 hours "post-assembly" refers to the time at which an hESC monolayer has detached from the SAM surface during the process of folding up into a cellular aggregate. As shown in FIG. 26A, approximately 99% of cells dissociated from 24 hour post-assembly EBs were Oct4$^+$ (top left and top right quadrants combined), with the majority (approximately 91%) also Nanog$^+$ (top right and bottom right quadrants combined). The aforementioned levels of pluripotency marker expression in self-assembled EBs are comparable to expression in hESCs (H1 line) maintained routinely on Matrigel-coated tissue culture polystyrene, >99% of which express both Oct4 and Nanog (see FIG. 26B). These results demonstrate that self-assembly of hESCs on cyclo(RGDF$_D$C) (SEQ ID NO:4) SAMs generates cell aggregates that remain pluripotent through the self-assembly process and up to at least 24 hours post-assembly.

hMSCs or hDFs were seeded on arrays at a density of ~1×10$^5$ cells/cm$^2$ to achieve confluent monolayers within 4 hours. Cells were cultured on SAMs in αMEM media containing 10% fetal bovine serum (FBS) for 2 hours after seeding. At this time, SAM arrays were rinsed in basal medium to remove nonspecifically adhered cells and replaced in fresh αMEM+10% FBS.

Figure 27:
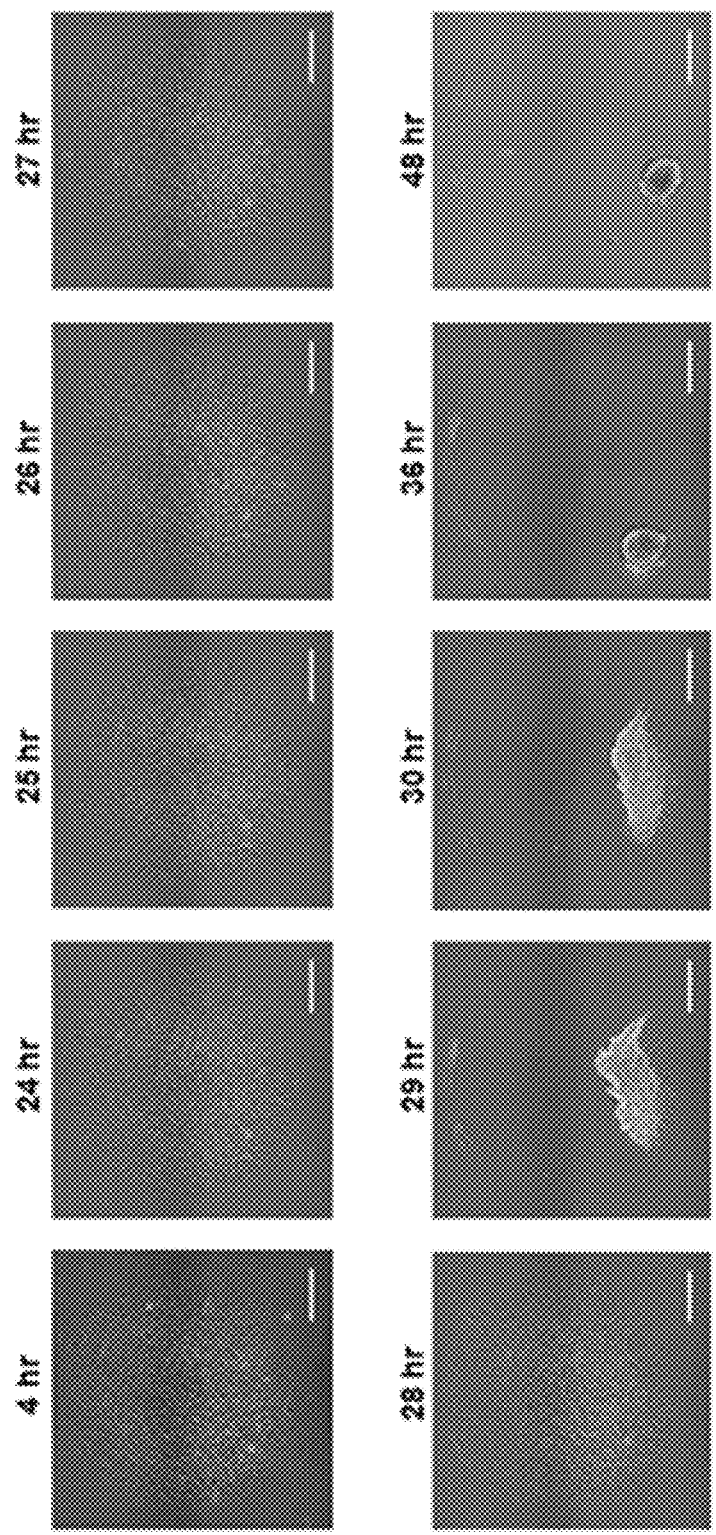
FIG. 27 depicts the nature and time scale of hMSC aggregate self-assembly from 2D monolayers, as shown on 5% cyclo(RGDF$_D$C) (SEQ ID NO:4) SAMs. hMSC monolayers were cultured on 1.2 mm diameter patterned SAM spots. In contrast to hESCs, hMSCs consistently completed self-assembly within 36 hours of initial seeding. Furthermore, hMSC self-assembly is characterized by large, rapid changes in population area (here, for example, between 28 hr and 29 hr). Qualitative observations suggest that hMSC self-assembly occurs in part due to cells rapidly contracting or pulling off the SAM substrate, thus implicating cellular contractility in this process. Scale bars represent 250 µm. hDF monolayers on 5% cyclo(RGDF$_D$C) (SEQ ID NO:4) self-assembled into aggregates with morphological similarity to hMSC self-assembly. Time scale of hDF self-assembly was variable.

Aggregates of non-pluripotent cells were also shown to self-assemble on labile SAMs. Specifically, monolayers of hMSCs or hDFs cultured on cyclo(RGDF$_D$C) (SEQ ID NO:4) SAMs detached from the SAM surface and contracted into small aggregates, in a manner distinct from the self-assembly of hESCs. As shown in FIG. 27, the self-assembly process of hMSCs began with contraction of the monolayer toward its center, followed by rapid pulling of the monolayer off the SAM surface and accumulation into an aggregate that typically retained adhesion to the edge of a patterned SAM spot. hDFs self-assembled into tight aggregates in an analogous manner (not shown). Aggregates of hMSCs and hDFs formed in this manner do not typically float into suspension, but can be physically released from the SAM surface by manual pipetting and collected thereafter.

Figure 28A:
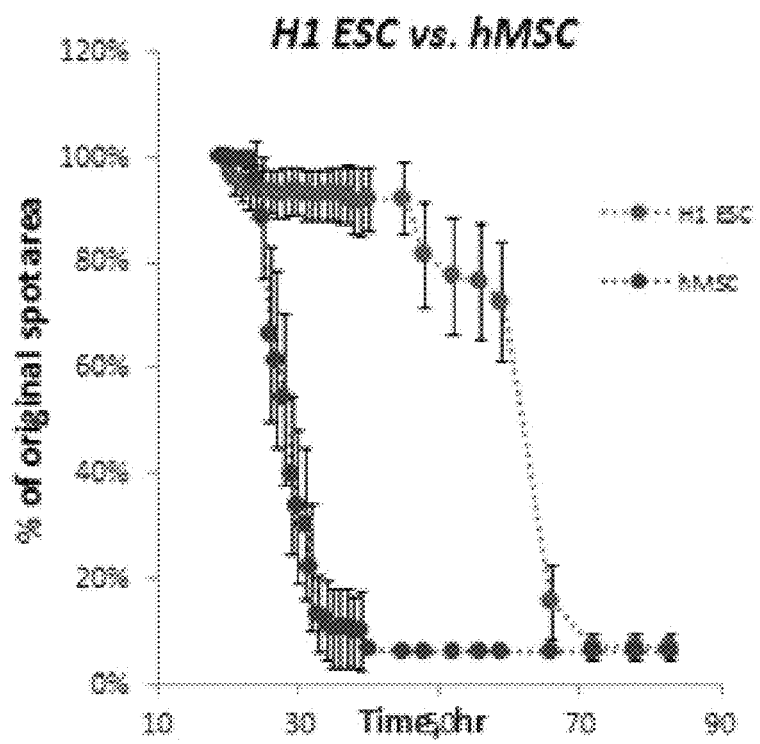
FIGS. 28A and 28B depict that cellular aggregate self-assembly is dependent on cell type.

The kinetics of aggregate self-assembly on cyclo(RGDF$_D$C) (SEQ ID NO:4) SAMs were found to be cell type-dependent. As demonstrated by FIG. 13 and FIG. 27, monolayers of hESCs and hMSCs undergo self-assembly into aggregates on vastly different time scales. As shown in the graphs in FIG. 28A, hESC monolayers typically begin the self-assembly process between 36 and 48 hours after initial seeding and have completed this self-assembly process by 72 hours, while hMSC monolayers typically begin self-assembly by 24 hours after initial seeding and have completed this process by 36 hours. In this Example, the beginning of self-assembly is characterized by the time point at which an evident decrease in projected area of the cell monolayer first occurs. The completion of self-assembly is considered the time point at which no further decreases in monolayer projected area occur, and is marked by the appearance of a plateau in graphical traces of monolayer projected area (see FIG. 28A).

Figure 28B:
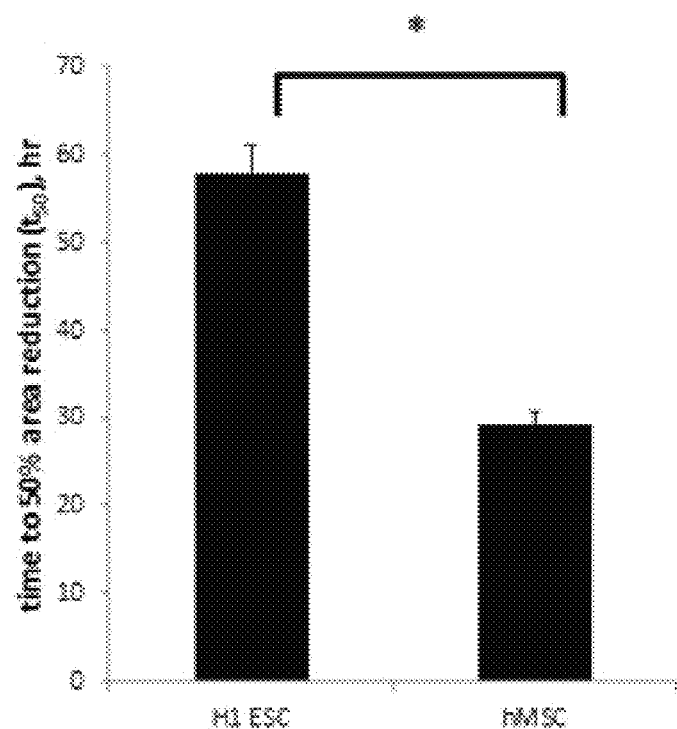
Figure 29A:
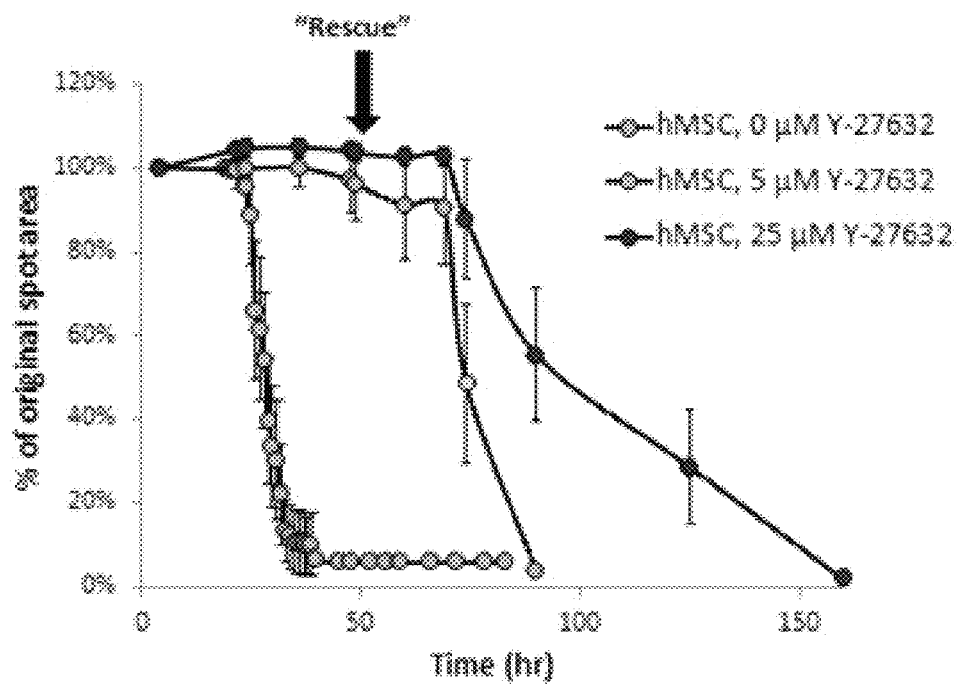
FIGS. 29A and 29B depict that cellular contractility influences the kinetics of cellular aggregate self-assembly.
Figure 29B:
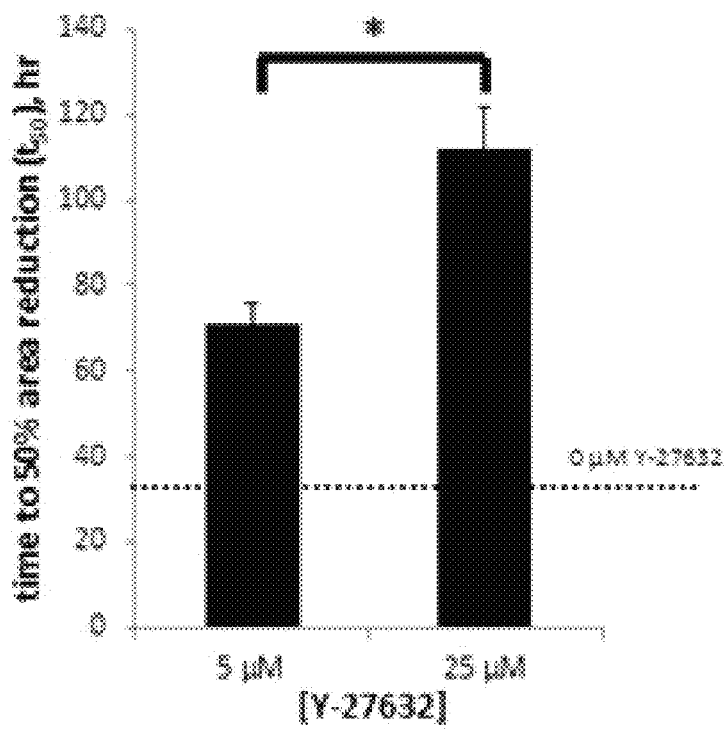

Cellular contractility was found to influence the kinetics of aggregate self-assembly on cyclo(RGDF$_D$C) (SEQ ID NO:4) SAMs. Based on cell type-dependent differences in the kinetics and morphological nature of aggregate self-assembly between hESCs and hMSCs, the influence of cellular contractility on self-assembly was investigated in hMSCs, a type of adult stem cell in which actin-myosin contractility has been shown to regulate lineage commitment toward adipogenesis or osteogenesis. As shown in FIGS. 29A & 29B, inhibition of Rho kinase (ROCK, "Y-27632"), an effector downstream of the actin-myosin contractile apparatus, was sufficient to delay the onset of hMSC aggregate self-assembly. In particular, while $t_{50}$ of self-assembly of hMSCs in the absence of Y-27632 occurred at approximately 30 hours after initial seeding, a 48-hour treatment of hMSC monolayers with 5 μM Y-27632 delayed $t_{50}$ of self-assembly to approximately 70 hours. The effect of ROCK inhibition was concentration-dependent in the range tested, as a 48-hour treatment with 25 μM Y-27632 further delayed the $t_{50}$ of hMSC self-assembly to approximately 112 hours. These findings support the results of FIGS. 28A & 28B, wherein hMSC monolayers tend to self-assemble significantly more rapidly than hESC monolayers, based on the higher contractility exhibited by hMSC monolayers. Together, these results suggest that cellular contractility is a key parameter that, in addition to cell-material adhesion, may be modulated to control the kinetics of cellular aggregate self-assembly on cyclo(RGDF$_D$C) (SEQ ID NO:4) SAMs.

These results demonstrate that the SAM arrays of the present disclosure can be used to culture cell populations with controlled size and shape. Moreover, the methods of the present disclosure allow for the development of a two-dimensional monolayer of cells that proceeds through morphological stages to develop into a three-dimensional cell aggregate. Further, it is shown that these morphological changes are likely to occur as a direct result of labile surface chemistry that promotes the loss of adhesion peptides covalently coupled to the SAMs over time in aqueous cell culture media. Using this technology, it has been demonstrated that cell-material adhesion and cellular contractility are important aspects of the aggregate self-assembly process, and can be tailored to control self-assembly kinetics.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements.

What is claimed is:

1. A method of controlling the formation of a cell culture aggregate, the method comprising:
   forming on a substrate, at least one alkanethiolate self-assembled monolayer spot wherein the spot is conjugated to a cellular adhesive peptide consisting of SEQ ID NO: 4 using a labile covalent bond, wherein the spot is part of a self-assembled monolayer array, and wherein the self-assembled monolayer array is prepared using a method selected from the group consisting of microcontact printing, microfluidics, stamping, photochemistry, locally removing a region in a fully formed self-assembled monolayer and reforming a new self-assembled monolayer in the region;
   culturing at least one cell on the alkanethiolate self-assembled monolayer spot for a sufficient time to form a confluent monolayer of cells; and
   detaching the confluent monolayer of cells from the array spot by latent nucleophilic cleavage of the labile covalent bond between the cellular adhesive peptide and the alkanethiolate, wherein the detached confluent monolayer of cells forms the cell culture aggregate; and
   collecting the cell culture aggregate.

2. The method of claim 1, wherein the confluent monolayer is cultured for a period of from about 6 hours to about 144 hours.

3. The method of claim 1, further comprising culturing the confluent monolayer for a sufficient time to allow the confluent monolayer to invaginate.

4. The method of claim 3, wherein the confluent monolayer is cultured for a period of from about 6 hours to about 144 hours.

5. The method of claim 1, wherein the cell is selected from the group consisting of an induced pluripotent stem cell, a mesenchymal stem cell, an umbilical vein endothelial cell, a dermal fibroblast, a fibrosarcoma cell, an embryonic stem cell, an iPS IMR90-4 cell, an iPS-derived endothelial cell, and combinations thereof.

6. The method of claim 1, wherein the specified diameter of the array spot is from about 600 μm to about 6 mm.

7. The method of claim 1, wherein said aggregates comprises either a uniform size or a specified shape.

8. The method of claim 7, wherein the specified shape is selected from the group consisting of a circle, an oval, and oval cross, a star, and a hand.

* * * * *

SEQUENCE LISTING

<160> NUMBER OF SEQ ID NOS: 9

<210> SEQ ID NO 1
<211> LENGTH: 9
<212> TYPE: PRT
<213> ORGANISM: Artificial Sequence

```
<220> FEATURE:
<223> OTHER INFORMATION: Synthetic

<400> SEQUENCE: 1

Gly Trp Gly Gly Arg Gly Asp Ser Pro
1               5

<210> SEQ ID NO 2
<211> LENGTH: 9
<212> TYPE: PRT
<213> ORGANISM: Artificial Sequence
<220> FEATURE:
<223> OTHER INFORMATION: Synthetic

<400> SEQUENCE: 2

Gly Trp Gly Gly Arg Gly Glu Ser Pro
1               5

<210> SEQ ID NO 3
<211> LENGTH: 8
<212> TYPE: PRT
<213> ORGANISM: Artificial Sequence
<220> FEATURE:
<223> OTHER INFORMATION: Synthetic

<400> SEQUENCE: 3

Gly Gly Arg Gly Asp Ser Pro Lys
1               5

<210> SEQ ID NO 4
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: D-phenylalanine
<222> LOCATION: (4)..(4)

<400> SEQUENCE: 4

Arg Gly Asp Phe Cys
1               5

<210> SEQ ID NO 5
<211> LENGTH: 14
<212> TYPE: PRT
<213> ORGANISM: Artificial Sequence
<220> FEATURE:
<223> OTHER INFORMATION: Synthetic

<400> SEQUENCE: 5

Cys Gly Lys Lys Gln Arg Phe Arg His Arg Asn Arg Lys Gly
1               5                   10

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Lys Arg Thr Gly Gln Tyr Lys Leu
1               5

<210> SEQ ID NO 7
<211> LENGTH: 5
```

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-Phenylalanine

<400> SEQUENCE: 7

Arg Gly Asp Phe Lys
1               5

<210> SEQ ID NO 8
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (4)..(4)
<223> OTHER INFORMATION: D-Phenylalanine

<400> SEQUENCE: 8

Arg Ala Asp Phe Lys
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: MOD_RES
<222> LOCATION: (1)..(1)
<223> OTHER INFORMATION: ACETYLATION

<400> SEQUENCE: 9

Cys Arg Gly Asp Ser
1               5
```